US011486876B2

(12) United States Patent
Superti-Furga et al.

(10) Patent No.: US 11,486,876 B2
(45) Date of Patent: Nov. 1, 2022

(54) MONOLAYER OF PBMCS OR BONE-MARROW CELLS AND USES THEREOF

(71) Applicant: CeMM—Forschungszentrum für Molekulare Medizin GmbH, Vienna (AT)

(72) Inventors: Giulio Superti-Furga, Vienna (AT); Berend Snijder, Vienna (AT); Gregory Vladimer, Vienna (AT)

(73) Assignee: CeMM—Forschungszentrum für Molekulare Medizin GmbH, Vienna (AT)

( * ) Notice: Subject to any disclaimer, the term of this patent is extended or adjusted under 35 U.S.C. 154(b) by 37 days.

(21) Appl. No.: 15/514,045

(22) PCT Filed: Sep. 24, 2015

(86) PCT No.: PCT/EP2015/072046
§ 371 (c)(1),
(2) Date: Mar. 24, 2017

(87) PCT Pub. No.: WO2016/046346
PCT Pub. Date: Mar. 31, 2016

(65) Prior Publication Data
US 2017/0356911 A1 Dec. 14, 2017

Related U.S. Application Data

(60) Provisional application No. 62/055,390, filed on Sep. 25, 2014.

(51) Int. Cl.
*G01N 33/50* (2006.01)
*G01N 33/569* (2006.01)
(Continued)

(52) U.S. Cl.
CPC ....... *G01N 33/56966* (2013.01); *C12M 23/12* (2013.01); *C12M 23/20* (2013.01);
(Continued)

(58) Field of Classification Search
None
See application file for complete search history.

(56) References Cited

U.S. PATENT DOCUMENTS

2009/0117653 A1\* 5/2009 Kirshner .............. C12N 5/0693
435/378

OTHER PUBLICATIONS

Richman et al., "In vitro evaluation of experimental agents for anti-HIV activity", in Current Protocols in Immunology, John Wiley and Sons (2001).\*

(Continued)

*Primary Examiner* — Erin M. Bowers
(74) *Attorney, Agent, or Firm* — Parker Highlander PLLC

(57) ABSTRACT

The invention relates to peripheral blood mononuclear cell (PBMC) monolayers or bone-marrow cell monolayers and methods for its culture and corresponding uses of said monolayers. The present invention also relates, in some aspects, to screening methods comprising the PBMC monolayer or bone-marrow cell monolayer of the invention for determination of response or lack of response of a disease to a therapeutic agent and/or drug screening methods. In some aspects, the invention further relates to methods for diagnosing a disease or predisposition to a disease in a PBMC donor or bone-marrow cell donor comprising the PBMCs/bone-marrow cells cultured according to the method of the invention and/or to methods for determining whether the disease is likely to respond or is responsive to treatment with a therapeutic agent.

14 Claims, 21 Drawing Sheets

Figure 1:
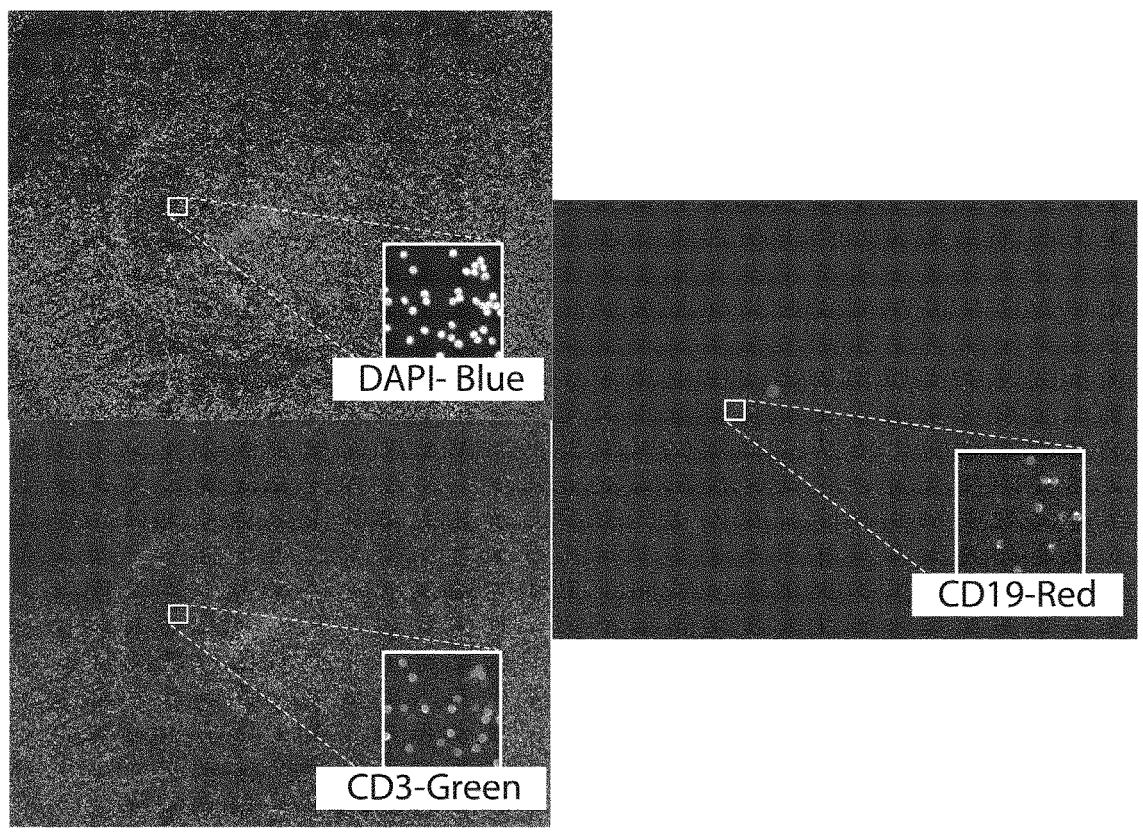

(51) Int. Cl.
- C12N 5/078 (2010.01)
- G01N 33/574 (2006.01)
- C12N 5/077 (2010.01)
- C12M 1/32 (2006.01)
- C12M 1/00 (2006.01)
- G01N 1/30 (2006.01)

(52) U.S. Cl.
CPC ......... *C12N 5/0634* (2013.01); *C12N 5/0669* (2013.01); *G01N 1/30* (2013.01); *G01N 33/5044* (2013.01); *G01N 33/56972* (2013.01); *G01N 33/574* (2013.01); *G01N 33/57407* (2013.01); *G01N 33/57426* (2013.01); *G01N 2800/50* (2013.01); *G01N 2800/52* (2013.01)

(56) References Cited

OTHER PUBLICATIONS

Pemovska et al., Cancer Discovery 3(12): 1416-1429 (2013; published online Sep. 20, 2013).*
Knapp et al., Cytometry 18: 187-198 (1994).*
Promega, "CellTiter-Glo Luminescent Cell Viability Assay", https://www.promega.com/-/media/files/resources/protocols/technical-bulletins/0/celltiter-glo-luminescent-cell-viability-assay-protocol.pdf?la=en, accessed Jul. 10, 2019.*
Pemovska et al., Cancer Discovery 3(12): 1416-1429 (2013).*
Luqman et al., Blood 112(3): 711-720 (2008).*
Beckman Coulter, Vi-CELL XR cell viability analyzer, https://www.beckman.com/cell-counters-and-analyzers/vi-cell-xr#, accessed May 26, 2021.*
Ramsay et al., Blood 120(7): 1412-1421 (2012).*
Wong et al., Haematologica 98(12): 1930-1938 (2013).*
"IHC/ICC Protocol Guide," URL:http://www.rndsystems.com/resources/images/6903.pdf, Oct. 25, 2011.
Akoume et al., "Cell-based Assay Protocol for the Prognostic Prediction of Idiopathic Scoliosis Using Cellular Dielectric Spectroscopy," *J. Vis. Exp.* 80:e50768, 2013.
Ambros et al., "Combined Immunofluorescence and FISH: New Prospects for Tumor Cell Detection/Identification," *Curr. Protocol. Cytometry*, 2004.
Blenman et al., "Cytospin: Cytospin Cell Resuspension Solution," *Sanguine Bioscience Blog*, URL:https://technical.sanguinebio.com/techniques-in-cytology-cytospin-cytospin-cell-resuspension-solution/, Aug. 20, 2013.
International Search Report issued in corresponding PCT Application No. PCT/EP2015/072046, dated Dec. 21, 2015.
Pemovska et al., "Individualized Systems Medicine Strategy to Tailor Treatments for Patients with Chemorefractory Acute Myeloid Leukemia," *Cancer Discov.*, 3(12):1416-1429, 2013.
Richman et al., "In Vitro Evaluation of Experimental Agents for Anti-HIV Activity," In: "Current Protocols in Immunology", John Wily & Sons, Inc., 12.9.6-12.9.10, 2001.
Koh, "Preparation of cells for microscopy using cytospin," *Methods in Enzymology*, 533:235-240, 2013.
Office Action issued in Singapore Application No. 11201702316S, dated Mar. 19, 2019.
Sutkowski et al., "A peripheral blood-derived monolayer supports long-term cultures of human CD4+ and CD8+ T lymphocytes," *Blood*, 85(11):3213-3222, 1995.
Basiji et al., "Cellular image analysis and imaging by flow cytometry," *Clin Lab Med.*, 27(3):653, 2007.
Office Action issued in Canadian Application No. 2,962,115, dated Oct. 21, 2021.

\* cited by examiner

Pharmacoscopy allows *personalized* drug discovery

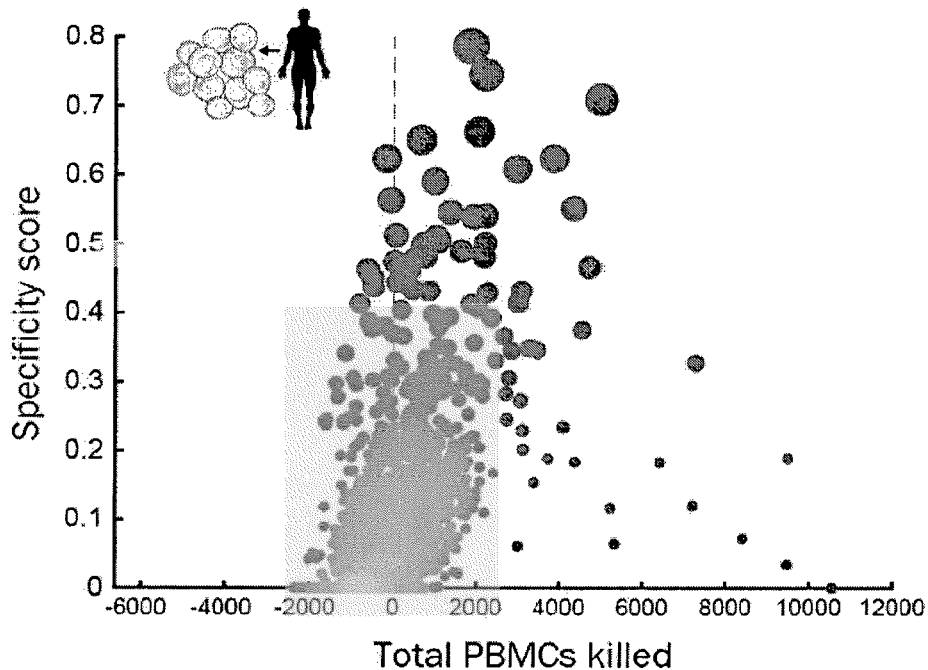

Figure 8c

Pharmacoscopy allows *personalized* drug discovery

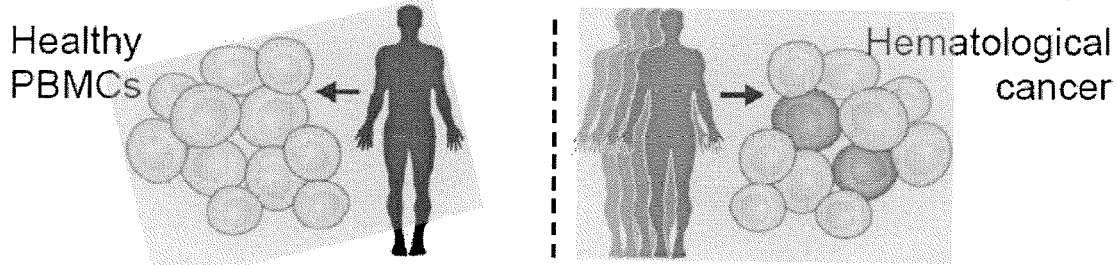

- Novel drug discovery:
  - Population specific targets
  - Sub-cellular phenotypes
  - 1X 500cc donation enables ~50,000 compound screen

- Personalized chemotherapy:
  - *Ex vivo* phenotype / biomarker tracking elucidates *in vivo* patient responses
  - Inherent controls
  - *Not a model system*

Figure 8d

Figure 12:
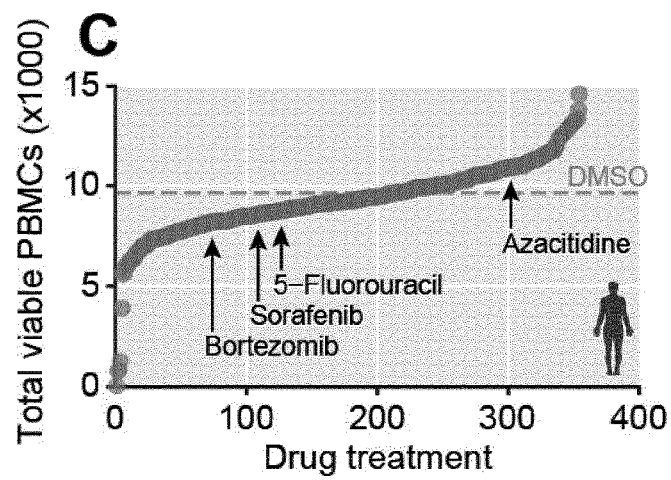
Figure 12:
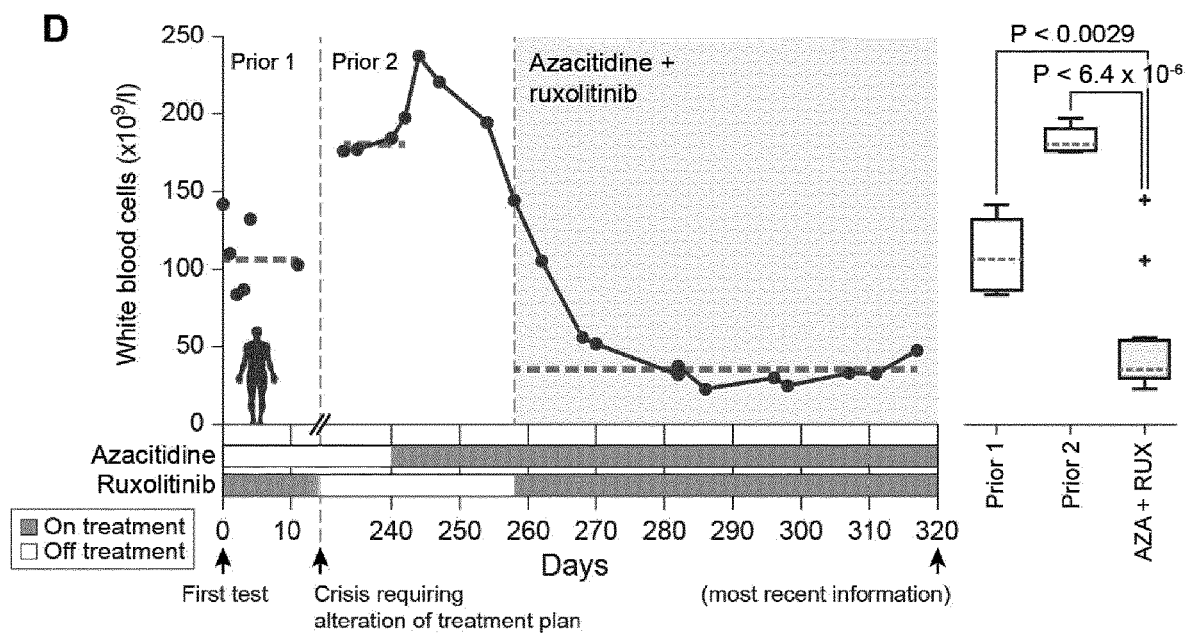

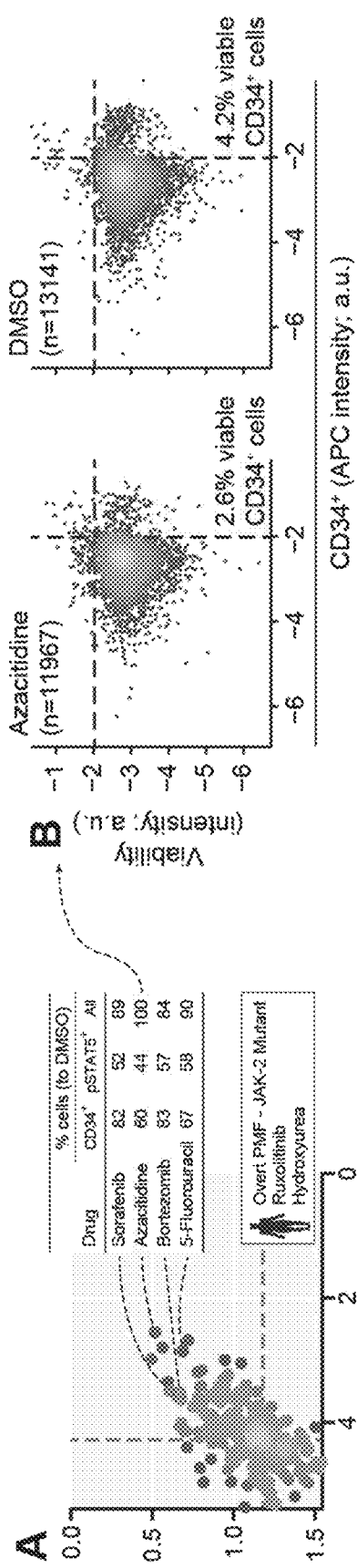
Figure 12 A and B

Viability Stain

Nuclear Stain     10x

Viability Stain

Nuclear Stain                                   20x

Arrow – example natural interactions lost upon spinning of plate 10x                    10x Zoom Arrow – Clumping
Arrow head – morphology characteristics Arrow - Clumping

MONOLAYER OF PBMCS OR BONE-MARROW CELLS AND USES THEREOF

This application is a national phase application under 35 U.S.C. § 371 of International Application No. PCT/EP2015/072046, filed Sep. 24, 2015, which claims benefit of U.S. Provisional Application No. 62/055,390, filed Sep. 25, 2014, and European Application No. 14186286.2, filed Sep. 24, 2014, the entire contents of each of which are hereby incorporated by reference.

The invention relates to peripheral blood mononuclear cell (PBMC) monolayers and bone-marrow cell monolayers and methods for corresponding cultures and corresponding uses of said monolayers. The present invention also relates, in some aspects, to screening methods comprising the PBMC monolayer or bone-marrow cell monolayer of the invention for determination of response or lack of response of a disease to a therapeutic agent and/or drug screening methods. In some aspects, the invention further relates to methods for diagnosing a disease or predisposition to a disease in a PBMC donor or bone-marrow cell donor comprising the PBMCs/bone-marrow cells cultured according to the method of the invention and/or to methods for determining whether the disease is likely to respond or is responsive to treatment with a therapeutic agent. In particular, the present invention provides for an in vitro produced peripheral blood mononuclear cell (PBMC) monolayer or bone-marrow cell monolayer, wherein natural-occurring cell-cell interactions and membrane integrity are maintained during formation of the monolayer and a PBMC monolayer or bone-marrow cell monolayer in vitro produced by a method comprising (a) isolating PBMCs from a blood sample or bone-marrow cells from bone-marrow; and (b) incubating PBMCs or bone-marrow cells at a density of about 100 cells per $mm^2$ to about 30000 cells per $mm^2$.

The understanding of cell behavior on a global scale after perturbation is significantly furthered by analysis at the single-cell level, including inter-cellular and cell-to-cell relationship resolution. The field of high-content imaging is continually providing evidence that cell-to-cell variability, and cell-microenvironment, in the detailed analysis of cell-population phenotypes is necessary for the determination of sensitive phenotypes (reviewed in Snijder et al. (2011) Nature Reviews 12, 119). Variations in cellular phenotype on a global level are largely determined by the inherent properties of developing cell populations that create specialized niche microenvironments, including cell densities, cell-cell contacts, relative location and cell-space. Moreover, at the single-cell level, the heterogeneity of cellular-responses to the same perturbation can be characterized (Slack et al. (2008) PNAS 105(49):19306-11). The complexity of cellular heterogeneity (in reference to the investigation of degree to which cancer cells react to anti-cancer drugs) reveals functional significance to the broad effect patients may have on a cellular level during chemotherapy.

However, studies which have laid the groundwork for population-characteristic analysis driven by sub-cellular and single-cell resolution have relied on genetically identical cell lines, which are not physiologically relevant to human health and disease. In this regard, methods of the prior art comprise separation/isolation of cell populations and/or other means, which destroy natural cell-cell interactions and/or membrane integrity, by, inter alia, application of gravitational forces, in particular centrifugation or spinning, or cell lysis. Accordingly, cell samples and/or methods as described by Douglas et al. (2001) Current Protocols in Immunology (May 1, 2001), Katrien Princen et al. (2002) Cytometry Part A, 51A, no. 1, pp. 35-45 or Peter Ambros et al. (2004) Current Protocols in Cytometry (Nov. 1, 2004) do not reflect physiologically relevant states and/or are unable to analyse physiologically relevant cell samples. The same holds true with regard to Cytospin® analyses, which use gravitational forces to obtain cell samples, wherein almost no natural occurring cell-cell interactions are maintained; see e.g. Ikeda et al. (2011) Diagnostic cytopathology 39(6), pp. 395-401. Moreover, the relevance of drug-discovery for human diseases in cell lines has recently been brought into question after identification of inconsistencies in published work were identified (Haibe-Kains et al. (2013) Nature 504, 389-93).

In addition, predictive chemotherapy for hematopoietic cancers, e.g. personalized diagnosis or personalized medicine, is an emerging field with continually evolving technologies. To date, such studies have depended on isolation of specific cell populations or average populations parameters, e.g. cell size, viability, activity, and depend on flow cytometry sorting of cancerous blasts based on membrane CD markers, measuring only cell death (ATP release) after drug incubation compared to random healthy donors (Pemovska et al. (2013) Cancer Discov 3, 1416-29). No study has yet used the power of high-throughput chemotherapy testing with high-content microscopy to integrate cell viability (membrane integrity), biomarker tracking, pathway activation/culmination, and the spatial relationship of cells to each other in the physiologically relevant blood milieu. Moreover, none of the techniques known in the art takes advantage of the entire patient sample (healthy and cancerous cells, i.e., for a global perspective), but rather uses flow cytometry with sorting a blast-only population which results in cell loss, and risks reducing cellular health during the sorting process. Yet, it is known that chemical compounds, for example drugs, have an effect on cell-cell interactions between cells of different subsets/subpopulations, which are, however, not maintained/analyzable by means and methods known in the art.

Therefore, there is a need for means and methods for providing systems that reflect the in vivo situation, whereby these systems can be used for PBMCs and/or bone-marrow cells to reflect the in vivo situation and/or an in vivo representation of cells, whereby the systems can be used in methods of diagnosis of disease or predisposition to disease, in drug screenings, and in the assessment of treatment results or predispositions to treatment.

The present invention thus provides an in vitro produced peripheral blood mononuclear cell (PBMC) monolayer or bone-marrow cell monolayer, wherein in said monolayers natural-occurring cell-cell interactions and/or the membrane integrity are maintained during formation of said monolayer. That is, the present invention relates to an in vitro produced PBMC monolayer or in vitro produced bone-marrow cell monolayer, said monolayer representing the/a physiologically-relevant state of the majority of cells comprised in said monolayer(s). Accordingly, the present invention relates to a peripheral blood mononuclear cell (PBMC) monolayer or bone-marrow cell monolayer, wherein natural-occurring cell-cell interactions and membrane integrity are maintained during formation of the monolayer, means and methods for the production of such monolayers and uses of such monolayers. Therefore, the present invention provides monolayers obtained or obtainable by any of the methods provided herein.

Figure 15A:
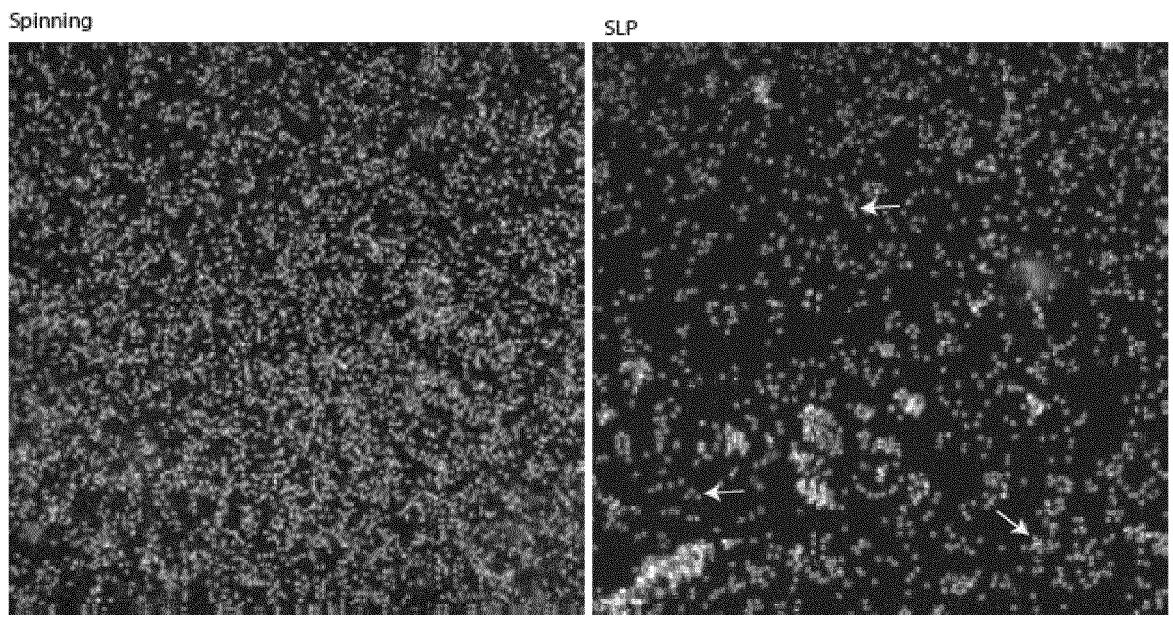

As evidenced by the appended Examples, cell layers of the prior art cannot be used to visualize/use/track/assess cell-cell interactions, which is, inter alia, due to gravitational forces applied to the sample (in particular during the formation of prior art cell layers). Such gravitational forces may be, in particular centrifugation. Also, the prior art methods employ techniques, which lead to undesired cell lysis and the like, which destroy membrane integrity and natural-occurring cell-cell interaction. In contrast, the present invention surprisingly and unexpectedly provides PBMC and bone-marrow cell monolayers, wherein cell-cell interactions and membrane integrity as found in a natural environment are maintained during the formation of the PBMC and bone-marrow cell monolayer. The maintenance of cell-cell interactions and/or membrane integrity during formation of the monolayer allows that any effect based on cell-cell interactions and/or membrane integrity can be assessed/determined/visualized using the monolayers of the present invention. As illustrated by the appended Examples, cell-cell interactions can be visualized using the PBMC or bone-marrow cell monolayer of the present invention; see e.g. FIG. 15B (upper right image) and Example 13. In contrast, methods of the prior art, in particular Douglas et al. and Katrien Princen et al. lead to cell clumping and are unable to visualize natural-occurring cell-cell interactions; see e.g. FIG. 15C and Example 13.

For example, it is known that cells, in particular cells derived from hematopoietic stem cells, in particular PBMCs or bone-marrow cells, interact with each other via, inter alia, membrane receptors and/or sugar moieties on cell surfaces. For example, T-cells and dendritic cells are known to interact subsequent to infection. However, T-cells and dendritic cells show less or only loose interaction in non-diseased subjects. Accordingly, the monolayers, in particular PBMC monolayers and/or bone-marrow cells monolayers, of the invention allow the determination whether a donor suffers from a disease/infection and/or whether a donor is responsive to treatment. Furthermore, the monolayers, in particular PBMC monolayers or bone-marrow monolayers, of the invention can be used in drug screening methods, wherein cell-cell interactions and/or membrane integrity are altered due to a drug effect.

The term "cell-cell interactions" as used herein refers to the direct interactions between cell surfaces that play a crucial role in the development and function of multicellular organisms. These interactions allow cells to communicate with each other in response to changes in their microenvironment. Such cell-cell interactions can be stable such as those made through cell junctions. These junctions are involved in the communication and organization of cells within a particular tissue. Others are transient or temporary such as those between cells of the immune system or the interactions involved in tissue inflammation. These types of intercellular interactions are distinguished from other types such as those between cells and the extracellular matrix.

Maintaining cell-cell interactions means that a cell interacting with another cell in a natural environment will also interact with said other cell or a cell of the same cell type in the monolayers provided herein. That is, the overall cell-cell interactions are maintained, while cells do not necessarily maintain interaction with the same interacting cell.

The cell-cell interactions described above are maintained during the formation of the monolayer of the invention. Generally, cell-cell interactions naturally occur in the sample comprising PBMCs or bone-marrow cells used to form the monolayer of the invention. These natural-occurring cell-cell interactions are maintained during the subsequent production steps of the in vitro produced PBMC monolayer or bone-marrow cell monolayer of the invention. The person skilled in the art can determine whether cell-cell interactions are naturally-occurring and are maintained in the PBMC monolayer and/or bone-marrow cell monolayer of the invention. In particular, the person skilled in the art can use methods well-known in the art. In particular, the cell-cell interactions are maintained during addition of detectable labels and/or dyes, in particular a viability dye. Subsequent to formation of the monolayer, cell-cell interactions may be interrupted by, e.g, fixation of the monolayer prior to imaging.

Cell-cell interactions maintained during the formation of the monolayer of the invention and maintained in the methods of the present invention include, for example, the following cell-cell interactions indicative of specific diseases and/or indicative of healthy donors.

TABLE 1

| State/Disease | diagnostic cell marker 1 | diagnostic cell marker 2 | diagnostic cell marker 3 |
| --- | --- | --- | --- |
| natural-occurring in healthy donors | CD11C (+) | CD3 (+) | |
| natural-occurring in healthy donors | CD14 (+) | CD3 (+) | |
| natural-occurring in healthy donors | CD11C (+) | CD4 (+) | |
| natural-occurring in healthy donors | CD11C (+) | CD8 (+) | |
| natural-occurring in healthy donors | CD19 (+) | CD3 (+) | |
| Acute or chronic myeloid leukemia | CD117 (+) | CD34 (+) | |
| primary myelofibrosis | CD34 (+) | pSTAT5 (+) | |
| Acute B lymphoblastic leukemia | CD19 (+) | CD34 (+) | CD10 (+) |
| T-cell acute lymphoblastic leukemia | CD3 (+) | CD10 (+) | |
| Chronic lymphocytic leukemia | CD19 (+) | CD5 (+) | |
| Multiple myeloma | CD28 (+) | CD117 (+) | CD138 (+) |

Accordingly, natural-occurring cell-cell interactions can be determined/assessed/detected using cell markers. In particular, natural-occurring cell-cell interactions can be determined/assessed/detected using markers shown in the above Table. For example, natural-occurring cell-cell interactions indicative of a healthy donor can be detected using, inter alia, cell marker pairs for CD11C and CD3, CD14 and CD3, CD11C and CD8, CD19 and CD3. Where interactions between cells positive for these markers are detected, the donor can be categorized as healthy.

Where cells comprised in the PBMC monolayer or bone-marrow cell monolayer are detected/labeled using the above provided cell markers indicative of specific diseases, the associated disease can be diagnosed in the cell donor and/or treatment of the associated disease can be assessed. Also, where cells comprised in the PBMC monolayer or bone-marrow cell monolayer of the invention are detected/labeled using markers indicative of healthy donors, the natural-occurring cell-cell interactions can be assessed/determined for such healthy donors. Further cell markers indicative of diseases are disclosed below.

As discussed above, the skilled person is aware of means and methods how to determine/assess/track/verify cell-cell interactions. In particular, the person skilled in the art can distinguish between natural-occurring cell-cell interactions and those introduced during the preparation of a cell sample. As such, the skilled person understands that cells of the same type and/or cells of different types interact in a living organism. The majority of cells comprised in the monolayers of the present invention maintain their natural-occurring cell-cell interactions. That is, the majority of cells, in particular at least 50% of the cells comprised in the monolayers of the invention, preferably 60%, 65%, 70%, 75%, 80%, 85%, 90%, 95%, or 100% of the cells comprised in the monolayers of the invention interact with the same cell or a cell of the same cell type as in vivo. Cell-cell interactions can be verified/assessed/determined using methods well-known in the art. For example, confocal microscopy can be used to assess/determine/verify whether cell-cell interactions are between cells interacting in a natural environment or between cells that do not show interaction in a natural environment. Such non-natural cell-cell interactions may be due to, inter alia, cell clumping. As evident from the appended Examples, such natural-occurring cell-cell interactions cannot be assessed/determined/verified using methods of the prior art, in particular means and methods described by Douglas et. or Katrien Princen et al.; see e.g. Example 12 and FIG. 15.

This distinguishes the monolayers of the present invention from known cell samples comprising PBMCs and/or bone-marrow cells, which show random interactions of cells and/or cell-cell interactions, which are generally not found or not found to the same extent in vivo, e.g. cell clumping. Accordingly, the PBMC monolayers and bone-marrow cell monolayers of the present invention reflect a physiologically-relevant state, as further evidenced by the ratio/number of cells present in the PBMC monolayers and bone-marrow cell monolayers of the invention, which reflect cell ratios/numbers found in vivo.

Accordingly, the present invention provides an in vitro produced physiologically-relevant PBMC monolayer and an in vitro produced physiologically-relevant bone-marrow cell monolayer. The term "in vitro produced" means that the monolayers are produced outside of a living organism, e.g. in a laboratory, i.e. outside of the normal biological context of cells comprised in the monolayer. Generally, in vitro studies allow investigation of various biological functions, while it is desirable to resemble the in vivo situation. With regard to cells comprised in the monolayers of the invention, the in vivo situation is resembled to an extent that allows various investigations and conclusions, as provided herein, which cannot be drawn from existing cell samples. As such, the in vitro resembling of an in vivo situation of PBMCs or bone-marrow cells, i.e. the provision of a physiologically-relevant state of such cells, provides various advantages over known methods, as described herein.

While natural-occurring cell-cell interactions are maintained during formation of the monolayer of the invention, the formation process may also involve that membrane integrity is maintained. This means that biological membranes as they occur in a natural environment are maintained during the process of forming the monolayer of the invention. Many of the above-described cell-cell interactions depend on intact membranes. Therefore, in the process of forming the monolayer of the invention, membrane integrity is preferably maintained to an extent that allows maintenance of cell-cell interactions as present in vivo. This may be achieved by avoiding the use of buffers that have an impact on membrane integrity, e.g. buffers interacting with biological membranes such as buffers comprising detergents. For example, buffers comprising Triton or SDS are to be avoided. The maintenance of membrane integrity during formation of the monolayer of the invention leads to formation of a monolayer comprising cells being in a physiologically-relevant state. Once the monolayer of the invention is formed, membrane integrity may be interrupted. Interruption of membrane integrity may allow accessibility of labels specific for one or more subpopulation(s) comprised in the monolayers of the invention. For example, the monolayer may be fixed prior to assessment/imaging. Means and methods used for fixation may involve interruption of membrane integrity. Accordingly, the monolayer of the invention is formed, wherein during formation the membrane integrity is maintained.

Accordingly, the present invention provides monolayers of PBMCs or bone-marrow cells that represent an in vitro produced representation of a physiologically-relevant state. The person skilled in the art is well-aware of methods how to assess whether a cell sample, as for example the monolayer of the present invention, represents a "physiologically-relevant state" of the cells comprised in said cell sample. In this regard, the term "physiologically-relevant state" or similar terms as used herein refers to a state resembling/reflecting an in vivo situation as it is found in a living organism, wherein said organism may be healthy or diseased. In particular, in a "physiologically-relevant state" cell-cell interactions and/or membrane integrity are preferably maintained as in vivo. Accordingly, the majority of cells, in particular at least 50% of the cells comprised in the monolayers of the invention, preferably 60%, 65%, 70%, 75%, 80%, 85%, 90%, 95%, or 100% of the cells comprised in the monolayers of the invention, preferably are in a state, which reflects the in vivo situation with regard to the stadium during a life cycle of cells and/or cell-cell interactions, as described above, and/or the representation of subpopulations present in vivo. As such, the skilled person is well-aware that a cell sample, in particular the monolayer of the invention, comprises cells of different subpopulations, wherein each cell of each subpopulation may be in a state of, inter alia, living, dead and/or dying. That is, in the monolayers of the present invention, the number/ratio of cells in each state, i.e. living, dead or dying, and each subpopulation preferably corresponds to the number/ratio that is found in vivo. That is, the physiologically-relevant state in which cells comprised in the monolayer of the present invention are found is preferably devoid of cells, which are found in a different state, i.e. living, dead or dying, as they are found in vivo or belonging to a different subpopulation. This requires that the preparation of the monolayer provided herein does not alter the number/ratio of cells in each state and/or in each subpopulation found in vivo.

Accordingly, in order to maintain numbers/ratios of cells of each subpopulation, it is preferred that pipetting is reduced. In this regard, samples used herein comprise adherent and non-adherent cells. Therefore, pipetting of the supernatant prior to formation of the monolayer may preferentially remove non-adherent cells, thus changing the overall representation of subpopulations comprised in the sample to be used for monolayer formation. A minimal starting volume, which avoids pipetting steps, is therefore preferred in the methods of the present invention and/or the methods used to obtain the monolayer of the present invention.

The reference sample referred-to as the in vivo sample/state/situation corresponds to a sample obtained from a donor, in particular a healthy or diseased donor, in parallel to the sample used in the methods of the present invention. For various diseases including hematologic malignancies, number/ratios of subpopulations of cells comprised in PBMCs and/or bone-marrow cells, are well-documented. Accordingly, such numbers/ratios may also be considered as reference sample representing the in vivo situation.

In order to provide a monolayer reflecting the in vivo situation, it is preferred that gravitational force applied during preparation of the monolayer, i.e. by the methods of the present invention, does not exceed 1 g. Preferably, this is achieved by avoiding the use of centrifugation and/or spinning. Accordingly, the methods of the present invention preferably do not comprise centrifugation and/or spinning subsequent to isolation of the cells. In addition, it is preferred that the monolayer of the invention is kept in solutions/buffers, which allow the maintenance of a physiologically-relevant state. As such, membrane integrity is preferably maintained in the monolayers of the invention, i.e. cells are preferably not lysed during preparation of the monolayer of the invention. In line with the above, the majority of cells comprised in the monolayers of the invention, in particular at least 50% of the cells comprised in the monolayers of the invention, preferably 60%, 65%, 70%, 75%, 80%, 85%, 90%, 95%, or 100% of the cells comprised in the monolayers of the invention, are preferably in a physiologically-relevant state, i.e. where cell-cell interactions are maintained and/or membrane integrity is maintained.

Accordingly, the present invention relates to an in vitro produced peripheral blood mononuclear cell (PBMC) monolayer or bone-marrow cell monolayer, wherein natural-occurring cell-cell interactions and membrane integrity are maintained during formation of the monolayer. This may be achieved where PBMCs or bone-marrow cells are maintained/processed/analyzed at about 1 g, i.e. 9.81 m/s$^2$ during the formation of the monolayer. In this respect, 1 g corresponds to standard gravity on the planet Earth, i.e. 9.81 m/s$^2$. This includes that during the process of formation of the monolayer of the invention, centrifugation and/or spinning are avoided, i.e. the sample is not subject to centrifugation and/or spinning. Accordingly, the present invention provides an in vitro produced peripheral blood mononuclear cell (PBMC) monolayer or bone-marrow cell monolayer, wherein natural-occurring cell-cell interactions and membrane integrity are maintained during formation of the monolayer, wherein subsequent to isolation the PBMCs or bone-marrow cells are maintained/processed/analyzed at about 1 g, i.e. 9.81 m/s$^2$.

The above does not exclude that the monolayers of the invention are processed/maintained/analyzed elsewhere than on planet Earth. For example, the monolayers of the invention may be processed/maintained/analyzed at a place where no or almost no gravitational force is present. Under such circumstances, gravitational force sufficient that cells settle can be artificially applied. Examples include space stations, reduced gravity aircrafts (zero gravity maneuver), other planets such as Mars or Venus, or natural satellites such as Earth's moon.

The "majority of cells" as used herein means that at least 50% of the cells comprised in the monolayers of the invention, preferably 60%, 65%, 70%, 75%, 80%, 85%, 90%, 95%, or 100% of the cells comprised in the monolayers of the invention are found in a physiologically-relevant state. The above percentages of cells in a physiologically-relevant state comprised in the monolayers of the invention are determined/measured/assessed using methods well-known in the art. In particular, whether a cell sample, in particular the monolayer of the present invention, comprises cells found in a physiologically-relevant state is determined by quantification of cells comprised in the monolayer. This may be done using methods well known in the art. In particular, quantification may be done through image analysis compared to the cells in peripheral blood or bone marrow of a reference individual or multiple reference individuals, e.g. one or more healthy donor(s) where the PBMC or bone-marrow cell sample is derived from a diseased donor. Quantification of cells is a standard diagnostic tool. Thresholds of cell subpopulations comprised in PBMCs and/or bone-marrow cells are well documented for healthy donors and diseased donors. Accordingly, based on differences in samples to be assessed using the means and methods of the present invention, the physiological-relevance can be determined. Documentation of cell subpopulations comprised in hematopoietic cells can be found, for example, in Hallek et al. (2008) Blood 111(12). Accordingly, quantification and further means and methods, for example determination of cell-cell interactions using microscopy, allow the determination whether a cell sample represents a physiological-relevant state.

The monolayer may provide a unique model system that can be used, inter alia, in biological, biochemical and biophysical research. Moreover, the monolayer can be used in medical diagnostic and screening methods, e.g. in automated medical diagnostic and screening methods. Certain PBMC monolayers and bone-marrow cell monolayers provided herein require minimal donor material; thus, standard amounts of donor material, e.g., as obtained for routine blood analysis protocols, may be used to test or analyze greater numbers of perturbations (e.g., individual test conditions) per donation than is possible using current methods known in the art. Additionally, certain PBMC monolayers and bone-marrow cell monolayers provided herewith can allow for the rapid assessment of results using imaging-based analysis, e.g., via assessment of microscopic images of stained samples (e.g., fluorescent staining via tagged antibodies), leading to automated processing, substantially reducing manpower requirements and processing/analysis times.

The monolayers provided in various aspects of the present invention can allow, inter alia, imaging and/or microscopic analysis of PBMC populations or bone-marrow populations. Accordingly, monolayer as used herein implies a single layer of cells found predominantly within the same focal plane of the imaging device, e.g., microscope or automated camera as is known in the art or described herein. The term single layer is used to mean that the cells within this layer form a culture that is predominantly 2-dimensional, i.e., the culture is predominantly a layer of single cells. That is, within the culture, the majority of the cells are not found resting on or above other cells, and are not found in aggregates (e.g., consisting of groups of cells that extend above the layer of single cells by comprising cells that rest on or above other cells). Thus, the PBMC monolayer within the meaning of the invention preferably comprises a horizontal layer of PBMC cells having a thickness of the height of one single PBMC. Likewise, the bone-marrow cell monolayer within the meaning of the invention preferably comprises a horizontal layer of bone-marrow cells having a thickness of the height of one single bone-marrow cell. As used herein, the term monolayer does not exclude that within the culture vessel cell aggregates or multilayer constructs (i.e., areas having cell cultures with a height of greater than one PBMC cell or one bone-marrow cell, respectively) or areas without cells may be found. Rather, the term is used to mean that the cultures of the invention will have the majority of their imageable or visible area (e.g., by microscopic methods) consisting of a single layer of cells. This is most easily accomplished as providing a single layer of cells on a cell culture surface. As is understood in the art, PBMCs isolated from blood samples, or purified bone marrow, comprise predominantly non-adherent cells, and, thus, typically do not form strong contacts with cell-culture surfaces or strong cell-to-cell contacts. Therefore, the PBMC monolayers in various aspects of the present invention are not envisioned to be necessarily equivalent to monolayers of adherent cells as understood in the art, i.e., comprising a layer of cells firmly attached, evenly spread, and covering the majority of the culture surface. Rather, in some embodiments, the PBMC monolayer of the invention may comprise cultures of high density comprising a majority of cells in direct contact with one or more other cells, but not necessarily adhered to the culture surface, or may comprise cultures of low density, wherein cells are within the monolayer but have no (direct physical) contact with any other cell in the culture. The monolayers provided in certain aspects of the present invention may also comprise cultures of intermediate density, having discrete areas wherein cells are in contact with one or more cells and other areas where the cells exhibit no contact with other cells.

Because the monolayers provided herein allow for the first time the use of information derived from physiologically-relevant PBMC samples or bone-marrow cell samples, wherein natural-occurring cell-cell interactions and membrane integrity are maintained during formation of the monolayers, said information may be used in various applications, in particular medical and/or diagnostic applications.

Therefore, the present invention relates to, inter alia, a pharmaceutical composition comprising a compound for use in the treatment of a disease, in particular a hematologic malignancy and/or a malignancy of myeloid and/or lymphoid tissue of an individual, wherein said pharmaceutical composition is selected from at least two or more test compounds, wherein each of the at least two or more test compounds is tested in an assay comprising the steps of (a) preparing the hematopoietic cell monolayer, in particular PBMC or bone-marrow cell monolayer, of the invention using hematopoietic cells, in particular PBMCs or bone-marrow cells, of said individual; (b) determining one or more biological function(s) of one or more subpopulation(s) comprised in the hematopoietic cell monolayer, in particular PBMC monolayer or bone-marrow cell monolayer; (c) adding one of the at least two or more test compounds to the hematopoietic cell monolayer, in particular PBMC monolayer or bone-marrow cell monolayer; and (d) determining/tracking/assessing/verifying changes of said one or more biological function(s) of the one or more subpopulation(s) comprised in the hematopoietic monolayer, in particular PBMC monolayer or bone-marrow cell monolayer, wherein the assay is repeated for each of the at least two or more compounds and wherein the compound having the most advantageous effect on said one or more biological function(s) of said one or more subpopulation(s) is selected for treatment of said individual.

Various biological function(s) can be determined in the above process. In particular, it can be determined whether the cells comprised in the monolayer are in a physiologically-relevant state. The physiologically-relevant state may be characterized by cell-cell interactions maintained during formation of the monolayer and/or viability of cells comprised in the monolayer and/or membrane integrity maintained during formation of the monolayer. Accordingly, it is preferred that the biological functions determined in the above process are viability and/or cell-cell interactions of cells comprised in the monolayer.

In some aspects, the invention thus relates to a pharmaceutical composition comprising a compound for use in the treatment of a disease, in particular a hematologic malignancy and/or a malignancy of myeloid and/or lymphoid tissue of an individual, wherein said pharmaceutical composition is selected from at least two or more test compounds, wherein each of the at least two or more test compounds is tested in an assay comprising the steps of (a) preparing the hematopoietic cell monolayer, in particular PBMC or bone-marrow cell monolayer, of the invention using hematopoietic cells, in particular PBMCs or bone-marrow cells, of said individual; (b) determining viability and/or cell-cell interactions of one or more subpopulation(s) comprised in the hematopoietic cell monolayer, in particular PBMC monolayer or bone-marrow cell monolayer; (c) adding one of the at least two or more test compounds to the hematopoietic cell monolayer, in particular PBMC monolayer or bone-marrow cell monolayer; and (d) determining/track/assessing/verifying changes of viability and/or cell-cell interactions of the one or more subpopulation(s) comprised in the hematopoietic monolayer, in particular PBMC monolayer or bone-marrow cell monolayer, wherein the assay is repeated for each of the at least two or more compounds and wherein the compound reducing the viability/cell-cell interactions the most is selected for treatment of said individual.

Viability and/or cell-cell interactions of cells comprised in the monolayer can be determined and/or changes of viability and/or cell-cell interactions can be determined/assessed/tracked/verified using detectable labels/markers/dyes. Such labels/markers/dyes can be specific for one or more subpopulation(s) comprised in the monolayers of the invention. Where such specific labels/markers/dyes are used, they can be selected for cell types that play a role in various diseases and/or are known to have a biological function in a disease, in particular a hematologic malignancy and/or a malignancy of myeloid and/or lymphoid tissue.

Accordingly, in particular aspects, the invention relates to a pharmaceutical composition comprising a compound for use in the treatment of acute or chronic myeloid leukemia of an individual, wherein said pharmaceutical composition is selected from at least two or more test compounds, wherein each of the at least two or more test compounds is tested in an assay comprising the steps of (a) preparing the hematopoietic cell monolayer, in particular PBMC or bone-marrow cell monolayer, of the invention using hematopoietic cells, in particular PBMCs or bone-marrow cells, of said individual; (b) determining viability and/or cell-cell interactions of CD117 and/or CD34 positive cells comprised in the hematopoietic cell monolayer, in particular PBMC monolayer or bone-marrow cell monolayer; (c) adding one of the at least two or more test compounds to the hematopoietic cell monolayer, in particular PBMC monolayer or bone-marrow cell monolayer; and (d) determining/track/assessing/verifying changes of viability and/or cell-cell interactions of CD117 and/or CD34 positive cells comprised in the hematopoietic monolayer, in particular PBMC monolayer or bone-marrow cell monolayer, wherein the assay is repeated for each of the at least two or more compounds and wherein the compound reducing the viability/cell-cell interactions the most is selected for treatment of said individual. In particular aspects, the invention relates to a pharmaceutical composition comprising a compound for use in the treatment of primary myelofibrosis of an individual, wherein said pharmaceutical composition is selected from at least two or more test compounds, wherein each of the at least two or more test compounds is tested in an assay comprising the steps of (a) preparing the hematopoietic cell monolayer, in particular PBMC or bone-marrow cell monolayer, of the invention using hematopoietic cells, in particular PBMCs or bone-marrow cells, of said individual; (b) determining viability and/or cell-cell interactions of CD34 and/or pSTAT5 positive cells comprised in the hematopoietic cell monolayer, in particular PBMC monolayer or bone-marrow cell monolayer; (c) adding one of the at least two or more test compounds to the hematopoietic cell monolayer, in particular PBMC monolayer or bone-marrow cell monolayer; and (d) determining/track/assessing/verifying changes of viability and/or cell-cell interactions of CD34 and/or pSTAT5 positive cells comprised in the hematopoietic cell monolayer, in particular PBMC monolayer or bone-marrow cell monolayer, wherein the assay is repeated for each of the at least two or more compounds and wherein the compound reducing the viability/cell-cell interactions the most is selected for treatment of said individual.

The pharmaceutical composition of the invention comprises a compound selected from at least two or more test compounds. Test compounds are not particularly limited as long as they are suitable for use as pharmaceutical. However, it is preferred that said test compounds are selected from compounds known to be effective in the treatment of a disease, in particular a hematologic malignancy and/or a malignancy of myeloid and/or lymphoid tissue. Compounds known to be effective in the treatment of such diseases comprise chemical compounds and biological compounds, such as, for example, antibodies. Examples of compounds known to be effective in the treatment of such diseases include but are not limited to Alemtuzumab, Anagrelide, Arsenic trioxide, Asparaginase, ATRA, Azacitidine, Bendamustin, Blinatumomab, Bortezomib, Bosutinib, Brentuximab vedotin, Busulfan, Ceplene, Chlorambucil, Cladribine, Clofarabine, Cyclophosphamide, Cytarabine, Dasatinib, Daunorubicin, Decitabine, Denileukin diftitox, Dexamethasone, Doxorubicin, Duvelisib, EGCG=Epigallocatechin gallate, Etoposide, Filgrastim, Fludarabine, Gemtuzumab ozogamicin, histamine dihydrochloride, Homoharringtonine, Hydroxyurea, Ibrutinib, Idarubicin, Idelalisib, Ifosfamide, Imatinib, Interferon Alfa-2a, Recombinant, Interferon Alfa-2b, Recombinant, Intravenous Immunoglobulin, L-asparaginase, Lenalidomide, Masitinib, Melphalan, Mercaptopurine, Methotrexate, Midostaurin, Mitoxantrone, MK-3475=Pembrolizumab, Nilotinib, Pegaspargase, Peginterferon alfa-2a, Plerixafor, Ponatinib, Prednisolone, Prednisone, R115777, RAD001 (Everolimus), Rituximab, Ruxolotinib, Selinexor (KPT-330), Sorafenib, Sunitinib, Thalidomide, Topotecan, Tretinoin, Vinblastine, Vincristine, Vorinostat, Zoledronate, ABL001, ABT-199=Venetoclax, ABT-263=Navitoclax, ABT-510, ABT-737, ABT-869=Linifanib, AC220=Quizartinib, AE-941=Neovastat, AG-858, AGRO100, Aminopterin, Asparaginase Erwinia chrysanthemi, AT7519, AT9283, AVN-944, Bafetinib, Bectumomab, Bestatin, beta alethine, Bexarotene, BEZ235, BI 2536, Buparlisib (BKM120), Carfilzomib, Carmustine, Ceritinib, CGC-11047, CHIR-258, CHR-2797, CMC-544=Inotuzumab ozogamicin, CMLVAX100, CNF1010, CP-4055, Crenolanib, Crizotinib, Ellagic Acid, Elsamitrucin, Epoetin Zeta, Epratuzumab, FAV-201, Favld, Flavopiridol, G4544, Galiximab, gallium maltolate, Gallium nitrate, Givinostat, GMX1777, GPI-0100, Grn1631, GTI 2040, IDM-4, Interferon alfacon-1, IPH 1101, ISS-1018, Ixabepilone, JQ1, Lestaurtinib, Mechlorethamine, MEDI4736, MGCD-0103, MLN-518=Tandutinib, motexafin gadolinium, Natural alpha interferon, Nelarabine, Obatoclax, Obinutuzumab, OSI-461, Panobinostat, PF-114, PI-88, Pivaloyloxymethyl butyrate, Pixantrone, Pomalidomide, PPI-2458, Pralatrexate, Proleukin, PU-H71, Ranolazine, Rebastinib, Samarium (153sm) lexidronam, SGN-30, Skeletal targeted radiotherapy, Tacedinaline, Tamibarotene, Temsirolimus, Tioguanine, Troxacitabine, Vindesine, VNP 40101M, Volasertib, or XL228. The enclosed Examples illustrate the advantageous effects of the herein disclosed means and methods. As can be seen in FIG. 12, the means and methods provided herein can be used to determine/assess whether treatment is effective and/or whether a treatment regimen is effective. Previous methods rely on the overall number of killed PBMCs. In contrast, the means and methods provided herein allow the evaluation based on subpopulations comprised in the PBMC monolayers or bone-marrow cell monolayers of the invention using, for example, markers specific for such subpopulations. Therefore, a treatment decision can be reached based on the effect of a drug on a particular subpopulation or subpopulation(s) comprised in the PBMC monolayer or bone-marrow cell monolayer of the invention. Subsequent to testing multiple approved drugs that are used in the treatment of hematologic malignancies, it was decided to alter the treatment regimen for a patient undergoing treatment using Ruxolitinib. In particular, it was decided to additionally use Azacitidine, which significantly reduced the number of diseased cells; see FIG. 12D. Accordingly, the means and methods provided herein have successfully be used to diagnose a patient having a disease and to assess whether said patient is responsive to treatment and whether said patient will be responsive to alternative treatment.

The viability of cells comprised in the monolayers of the invention can be determined/assessed/verified using methods well-known in the art. That is, the skilled person is well-aware of methods how to determine/assess/verify the stadium of a cell, for example whether a cell is viable, live, dead or undergoing a process changing its stadium, for example dying as in apoptosis or necrosis. Accordingly, known markers/dyes that specifically recognize/label cells being in a particular stadium can be used in the methods of the invention. That includes dyes/labels that are selective for cells with non-intact membranes or dyes/labels selective for late-stage cell death or early apoptosis. For example, fixable live/dead green can be used (ThermoFisher, catalogue number L-23101), antibodies against cytochrome C, determining DNA turnover or cell proliferation through the use of dyes. Further means and methods how to determine/assess/verify viability of cells comprised in the monolayers of the invention are disclosed below and are known to the skilled person.

Determining/tracking/assessing/verifying changes of viability and/or cell-cell interactions of the one or more subpopulation(s) comprised in the hematopoietic monolayer, in particular PBMC monolayer or bone-marrow cell monolayer, can be done using methods well-known in the art. For example, using microscopy, changes can be determined/tracked/assessed/verified by optical perception. However, for high-throughput applications, it is preferred that an automated method is used, which determines/tracks/assesses/verifies changes of viability and/or cell-cell interactions of individual subpopulations comprised in the monolayers of the present invention. Such a method comprises identifying subpopulations comprised in the monolayer, e.g. by detectable labels. It can then be determined whether labeled/detected subpopulations show cell-cell interactions, wherein cell-cell interactions may include direct contacts via plasma membranes (as described above) or indirect contacts. Accordingly, a distance parameter between labeled cells is introduced, which determines a cell to be in contact with a further cell or not. Subsequently, the fraction, i.e. ratio, of cells of a subpopulation that is in contact with a further cell is determined. The resulting number is compared to what would be expected by a random distribution function, i.e. by random cell-cell interactions as they are observed in samples showing clumping. An interaction score can then be calculated, which determines whether interaction is random or directed. Following such a protocol before and after one or more test substance(s) are added to the monolayer of the invention, allows determining/tracking/assessing/verifying changes of cell-cell interactions due to the one or more test compound(s).

Furthermore, the present invention provides a method for culturing PBMCs or bone-marrow cells comprising (a) isolating PBMCs from a blood sample or bone-marrow cells from bone-marrow; and (b) incubating PBMCs or bone-marrow cells at a density of about 100 cells per mm$^2$ to about 30000 cells per mm$^2$.

Accordingly, the present invention provides methods for culturing or incubating peripheral blood mononuclear cells (PBMCs) in the form of a monolayer comprising (a) isolating PBMCs from a blood sample and (b) incubating PBMCs at a specific density. In particular, the density is that which maintains the PBMC monolayer culture during the entire culture time of the monolayer, e.g., from introduction into the culture device until final processing prior to imaging. For example, the maximum density is such that the total number of cells (a) introduced into the culture device or (b) expected to be present in the culture device subsequent to culturing and prior to processing for imaging does not exceed that number present at maximum density for the cell PBMC monolayer as described herein. The densities of the invention are typically lower than would normally be seeded into wells for the cultivation of PBMCs as known in the art. The PBMCs of the invention may be introduced and/or cultured to have in the culture device a density of about 100 cells per mm$^2$ growth area to about 30000 cells per mm$^2$ growth area. More preferably, the PBMCs are incubated at a density of about 500 cells per mm$^2$ growth area to about 20000 cells per mm$^2$ growth area, about 1000 cells per mm$^2$ growth area to about 10000 cells per mm$^2$ growth area, about 1000 cells per mm$^2$ growth area to about 5000 cells per mm$^2$ growth area, or about 1000 cells per mm$^2$ growth area to about 3000 cells per mm$^2$ growth area. Most preferably the PBMCs are incubated at a density of about 2000 cells per mm$^2$ growth area. Accordingly, the present invention provides a method for culturing PBMCs comprising (a) isolating PBMCs from a blood sample; and (b) incubating PBMCs at a density of about 2000 cells per mm$^2$.

The present invention provides, methods for culturing or incubating primary hematopoietic cells, in particular bone-marrow cells, in the form of a monolayer comprising (a) isolating primary hematopoietic cells, in particular bone-marrow cells, from a sample and (b) incubating bone-marrow cells at a specific density. In particular, the density is that which maintains the PBMC monolayer culture during the entire culture time of the monolayer, e.g., from introduction into the culture device until final processing prior to imaging. For example, the maximum density is such that the total number of cells (a) introduced into the culture device or (b) expected to be present in the culture device subsequent to culturing and prior to processing for imaging does not exceed that number present at maximum density for the bone-marrow cell monolayer as described herein. The densities of the invention are typically lower than would normally be seeded into wells for the cultivation of bone-marrow cells as known in the art. The bone-marrow cells may be introduced and/or cultured to have in the culture device a density of about 100 cells per mm$^2$ growth area to about 30000 cells per mm$^2$ growth area. More preferably, the bone-marrow cells are incubated at a density of about 500 cells per mm$^2$ growth area to about 20000 cells per mm$^2$ growth area, about 1000 cells per mm$^2$ growth area to about 10000 cells per mm$^2$ growth area, about 1000 cells per mm$^2$ growth area to about 5000 cells per mm$^2$ growth area, or about 1000 cells per mm$^2$ growth area to about 3000 cells per mm$^2$ growth area. Most preferably the bone-marrow cells are incubated at a density of about 2000 cells per mm$^2$ growth area. Accordingly, the present invention provides a method for culturing bone-marrow cells comprising (a) isolating bone-marrow cells from bone-marrow; and (b) incubating bone-marrow cells at a density of about 2000 cells per mm$^2$.

The term "about" as used herein shall have the meaning of within 10%, more preferably within 5%, of a given value or range. In particular, in some embodiments, the PBMCs of the invention are introduced and/or cultured to have in the culture device a density of about 100, i.e. from about 90 to about 110, cells per mm$^2$ growth area to about 30000, i.e. about 27000 to about 33000, cells per mm$^2$ growth area. More preferably, the PBMCs are incubated at a density of about 500, i.e. about 450 to about 550, cells per mm$^2$ growth area to about 20000, i.e. about 18000 to about 22000, cells per mm$^2$ growth area, about 1000, i.e. about 900 to about 1100, cells per mm$^2$ growth area to about 10000, i.e. about 9000 to about 11000, cells per mm$^2$ growth area, about 1000, i.e. about 900 to about 1100, cells per mm$^2$ growth area to about 5000, i.e. about 4500 to about 5500, cells per mm$^2$ growth area, or about 1000, i.e. about 900 to about 1100, cells per mm$^2$ growth area to about 3000, i.e. about 2700 to about 3300, cells per mm$^2$ growth area. Most preferably the PBMCs are incubated at a density of about 2000, i.e. about 1800 to about 2200, cells per mm$^2$ growth area.

The primary hematopoietic cells, in particular PBMCs and/or bone-marrow cells, for use according to the methods disclosed herein may be isolated from a sample obtained from a healthy subject, e.g., not suspected to suffer from a disease or suspected to be predisposed to a disease, or may be isolated from a sample obtained from a subject known to be suffering from a disease or suspected to suffer from a disease. The diagnosis of the disease state of the subject is made by standard methods routinely performed by those skilled in the art, e.g., physicians. Accordingly, the invention provides in some embodiments a primary hematopoietic cell monolayer, in particular a PBMC monolayer or bone-marrow cell monolayer for use in a diagnostic method for determining whether a disease will respond or is responsive to a therapeutic agent. The PBMC monolayers and bone-marrow cell monolayers described herein allow the visualization of cellular response and activity (e.g., both at the macro-level (e.g., intercellular interactions), at the sub-cellular level (e.g., subcellular changes in activity), and at the global level (e.g. whole-population changes) and thus provide unique systems allowing the evaluation of PBMC response or bone-marrow response, respectively, to one or more therapeutic agents. Thus, the PBMC monoloayers or bone-marrow monolayers described herein may be, inter alia, used as generic models allowing evaluation of therapeutic response, or likelihood of therapeutic response, e.g., where the PBMCs/bone-marrow cells are isolated from samples obtained from healthy subjects. The therapeutic response of two or more PBMC monolayers or bone-marrow cell monolayer, respectively, isolated from samples obtained from two or more healthy donors may be used to develop a standard, baseline, or expected response representative of a healthy population, e.g., not suffering from or not predisposed to suffer from a disease. Similarly, the therapeutic response of two or more PBMC monolayers or bone-marrow cell monolayers, respectively, isolated from samples obtained from two or more donors suffering from the same disease and/or predisposed to suffer from the same disease (or combinations thereof) may be used to develop a predictive standard, baseline, or expected response representative of a population suffering from the disease or predisposed to suffer from the disease. Alternatively or additionally, the PBMC monolayer or bone-marrow cell monolayer described herein can be used in a diagnostic method to predict whether the donor providing the sample from which the PBMCs/bone-marrow cells were isolated is suffering from or predisposed to a disease and/or whether the PMBC donor/bone-marrow cell donor will respond or is responsive to treatment with a therapeutic agent.

Analysis of the therapeutic response of the PBMC monolayer or bone-marrow cell monolayer can be predictive of the response of the disease state in the PBMC donor or bone-marrow cell donor, respectively; in this respect the methods provided in various aspects of the invention provide advantages over current methods available in the art. For example, the PBMC monolayers described herein may be composed of normal, e.g., healthy, cells and, where isolated from a sample obtained from a donor having a disease or predisposed to a disease, disease cells, e.g., the cells may thus have an abnormal phenotype or genotype themselves or representative of a disease state (e.g., having increased or decreased concentration relative to expected concentrations in a healthy individual). Therefore, the PBMC monolayers described herein contain healthy cells or a healthy cell population that may act as a self-control in the methods provided herein. That is, the therapeutic response of the disease-state cells can be directly compared to the response of the healthy cells in the same sample, and without the need for comparison to baseline responses and/or without the need for establishing separate control cultures. The monolayers of the invention comprising healthy and, where isolated from a sample obtained from a donor having a disease or predisposed to a disease, disease cells, can also be used to determine/visualize/track cell-cell interactions between diseased cells, healthy cells or between diseased and healthy cells. Alterations of cell-cell interactions and/or viability of cells subsequent to treatment or as compared to a reference can be predictive of responsiveness to treatment or predisposition to a disease. A reference can be a second sample taken from the same donor or a sample taken from a reference donor, e.g. a healthy donor, a donor known to have or to not have a predisposition or a diseased donor.

The invention also relates to, a method for diagnosing a disease or predisposition to a disease in a PBMC donor and/or for determining whether a subject suffering from or predisposed to a disease will respond or is responsive to treatment with a therapeutic agent comprising (a) isolating PBMCs from a blood sample obtained from said subject/donor; (b) incubating said PBMCs at a density of about 100 cells per mm$^2$ growth area to about 30000 cells per mm$^2$ growth area; (c) contacting said PBMCs with said therapeutic agent; and (d) assessing the response of the PBMCs to the therapeutic agent. Preferably, the PBMCs are incubated in step (b) at a density of about 500 cells per mm$^2$ growth area to about 20000 cells per mm$^2$ growth area, more preferably about 1000 cells per mm$^2$ growth area to about 10000 cells per mm$^2$ growth area, more preferably about 1000 cells per mm$^2$ growth area to about 5000 cells per mm$^2$ growth area, more preferably about 1000 cells per mm$^2$ growth area to about 3000 cells per mm$^2$ growth area. Most preferably the PBMCs are incubated at a density of about 2000 cells per mm$^2$ growth area. The term "about" shall have the meaning of within 10%, more preferably within 5%, of a given value or range. In particular, in some embodiments the PBMCs of the invention are incubated in step (b) of the methods of the invention to have in the culture device a density of about 100, i.e. from 90 to 110, cells per mm$^2$ growth area to about 30000, i.e. 27000 to 33000, cells per mm$^2$ growth area. More preferably, the PBMCs are incubated at a density of about 500, i.e. 450 to 550, cells per mm$^2$ growth area to about 20000, i.e. 18000 to 22000, cells per mm$^2$ growth area, about 1000, i.e. 900 to 1100, cells per mm$^2$ growth area to about 10000, i.e. 9000 to 11000, cells per mm$^2$ growth area, about 1000, i.e. 900 to 1100, cells per mm$^2$ growth area to about 5000, i.e. 4500 to 5500, cells per mm$^2$ growth area, or about 1000, i.e. 900 to 1100, cells per mm$^2$ growth area to about 3000, i.e. 2700 to 3300, cells per mm$^2$ growth area. Most preferably the PBMCs are incubated at a density of about 2000, i.e. 1800 to 2200, cells per mm$^2$ growth area. Subject to the assessment in step (d), the therapeutic regimen of the subject can be altered. For example, a therapeutic regimen can be implemented or the therapeutic regimen can be increased where response is positive; alternatively a proposed therapeutic regimen can be rejected or a currently implemented regimen can be halted where the assessment demonstrates no or lack of effective response.

The invention also relates to, a method for diagnosing a disease or predisposition to a disease in a bone-marrow cell donor and/or for determining whether a subject suffering from or predisposed to a disease will respond or is responsive to treatment with a therapeutic agent comprising (a) isolating bone-marrow cells from said subject/donor; (b) incubating said bone-marrow cells at a density of about 100 cells per mm$^2$ growth area to about 30000 cells per mm$^2$ growth area; (c) contacting said bone-marrow cells with said therapeutic agent; and (d) assessing the response of the bone-marrow cells to the therapeutic agent. Preferably, the bone-marrow cells are incubated in step (b) at a density of about 500 cells per mm$^2$ growth area to about 20000 cells per mm$^2$ growth area, more preferably about 1000 cells per mm$^2$ growth area to about 10000 cells per mm$^2$ growth area, more preferably about 1000 cells per mm$^2$ growth area to about 5000 cells per mm$^2$ growth area, more preferably about 1000 cells per mm$^2$ growth area to about 3000 cells per mm$^2$ growth area. Most preferably the bone-marrow cells are incubated at a density of about 2000 cells per mm$^2$ growth area. The term "about" shall have the meaning of within 10%, more preferably within 5%, of a given value or range. In particular, in some embodiments the bone-marrow cells of the invention are incubated in step (b) of the methods of the invention to have in the culture device a density of about 100, i.e. from 90 to 110, cells per mm$^2$ growth area to about 30000, i.e. 27000 to 33000, cells per mm$^2$ growth area. More preferably, the bone-marrow cells are incubated at a density of about 500, i.e. 450 to 550, cells per mm$^2$ growth area to about 20000, i.e. 18000 to 22000, cells per mm$^2$ growth area, about 1000, i.e. 900 to 1100, cells per mm$^2$ growth area to about 10000, i.e. 9000 to 11000, cells per mm$^2$ growth area, about 1000, i.e. 900 to 1100, cells per mm$^2$ growth area to about 5000, i.e. 4500 to 5500, cells per mm$^2$ growth area, or about 1000, i.e. 900 to 1100, cells per mm$^2$ growth area to about 3000, i.e. 2700 to 3300, cells per mm$^2$ growth area. Most preferably the bone-marrow cells are incubated at a density of about 2000, i.e. 1800 to 2200, cells per mm$^2$ growth area. Subject to the assessment in step (d), the therapeutic regimen of the subject can be altered. For example, a therapeutic regimen can be implemented or the therapeutic regimen can be increased where response is positive; alternatively a proposed therapeutic regimen can be rejected or a currently implemented regimen can be halted where the assessment demonstrates no or lack of effective response.

The present invention thus provides, methods using physiologically relevant, multi-population, primary hematopoietic samples in imaging studies to determine in a high-throughput manner: 1) the effects of chemotherapy on biomarkers at a global level based on single-cell analysis, 2) the ability for this technique to provide predictive chemotherapy ex vivo in patient samples, and 3) for the integration of many patient data sets over time to determine patterns in treatment assessments. As the skilled person is aware, primary hematopoietic samples as used in the methods of the invention comprise, inter alia, PBMCs and bone-marrow cells. Accordingly, the monolayer of primary hematopoietic cells as provided herein may comprise PBMCs and/or bone-marrow cells. That is, while the means and methods provided herein are described for PBMCs, the skilled person understands that identical means and methods are provided for bone-marrow cells. Accordingly, provided herein are methods for culturing bone-marrow cells, methods for determining whether a bone-marrow cell donor suffers from a disease or is predisposed to suffer from a disease, methods for diagnosing a disease or predisposition to a disease in a bone-marrow donor and methods for determining whether a subject suffering from or predisposed to a disease will respond or is responsive to treatment with a therapeutic agent comprising the use of bone-marrow cells. Furthermore, methods for drug screening and other methods provided herein for PBMCs are also disclosed for other hematopoietic cells, e.g. bone-marrow cells.

In this regard, bone marrow is the flexible tissue in the interior of bones. In humans, red blood cells are produced by cores of bone marrow in the heads of long bones in a process known as hematopoiesis. Bone marrow transplants can be conducted to treat severe diseases of the bone marrow, including certain forms of cancer such as leukemia. Additionally, bone marrow stem cells have been successfully transformed into functional neural cells and can also be used to treat illnesses such as inflammatory bowel disease. Accordingly, bone-marrow cells represent a valuable target in the treatment of various diseases, for example cancerous diseases or inflammatory diseases such as inflammatory bowel disease. As such, the methods provided herein using bone-marrow samples obtained from a donor are highly useful in the assessment/determination whether a donor suffers from such a disease or is predisposed to suffer from a disease. In addition, the methods provided herein using bone-marrow cells provide various advantages in high-throughput drug screening and the like.

Currently, due to the dogma of requiring adherent cells (macrophages, HeLa, etc.) to form a stainable and imageable monolayer, research groups have been unable to implement image-based single cell screening techniques in primary patient samples for high-throughput determination of chemotherapy-induced molecular (biomarker) changes and cancerous blast viability assessments, in particular where the disease state is represented or reflected in non-adherent cells, e.g., in blood-based diseases or conditions such as lymphomas and leukemias. To solve this problem, the inventors provide novel means and methods as well as a novel methodology and image-analysis pipeline, referenced herein as "pharmacoscopy", which allows the visualization of adherent and non-adherent cells in a single image, typically requiring only $1/10^{th}$ of the material needed per perturbation as compared to methods known in the art, and maximizing throughput and speed. Pharmacoscopy can provide the same information gathered by known methods, e.g., flow cytometry, but provides additional advantageous information such as measurement of subcellular phenotypes (protein localization/co-localization) and cellular microenvironment/neighbor relationship. Moreover, in certain embodiments, the described methods require fewer cells and therefore less patient material, less liquid volume, and nearly no human intervention; pharmacoscopy thereby greatly increases the number of molecular perturbations which can be tested in parallel and yields more detailed assessments. Moreover, without the need to sort cancerous cells from the inherent healthy populations, pharmacoscopy can track drug mediated biomarker changes while controlling, in parallel, the off-target drug effects. These important controls are done by tracking the viability of the healthy cells from the same donor, present in the same well, and in the same imaging field, to the viability and biomarker analysis of the targeted-cell populations.

Using pharmacoscopy, the analysis of drug-induced subcellular and single-cell biomarker changes, within patient blood samples, can predict clinical therapy outcomes tailored to individual patients. The standardization, perfection, and availability of this technology to basic research as well as medical professionals and clinics is an advantage for, inter alia, personalized medicine, predictive pharmacology as well as drug screening and therapeutic evaluation.

Accordingly, and in contrast to the prior art, "pharmacoscopy" as provided herein can be employed in a variety of applications, e.g. personalized medicine, drug screening programs, general drug screening, personalized drug screening, assessment of drug response, evaluation of treatment, verification of treatment efficacy, prediction of treatment response, population (drug) responses and the like. The means and methods provided herein, in particular "pharmacoscopy" based on PBMC monolayer technology, allow also therefore drug screenings and drug discoveries as well as personalized (i.e., subject/patient/individual related) drug discoveries or drug screenings. For example, in general drug discoveries and/or drug screenings as provided herein, in particular "pharmacoscopy", PBMCs of healthy versus diseased patients may be used and compared. Also, pooled PBMC samples may be employed as starting material for the inventive monolayers in the means and methods provided herein. In personalized drug discovery, preferably, individual PBMC samples of subjects/individuals/patients are employed as starting material for the inventive PBMC monolayers to be employed in accordance with the invention. Yet, also pooled PBMC samples may be of use and value in this context.

Current leukemia and lymphoma drug discovery standards involve the use of cancer cell lines that are far from physiologically relevant, as key signaling pathways through leukocyte population subsets do not exist in such model systems. The use of cell lines stems from the difficulty of scaling-up and optimizing screening systems using PBMCs, especially when depending on imaging for high-content data gathering. In contrast, the methods provided herein can allow, in various embodiments, the large-scale screening of improved numbers of perturbation. For example, using the methods of the invention large numbers of perturbations can be efficiently and quickly investigated using the large numbers of PBMC monolayers that may be derived from a single sample obtained from a patient. Typically, the effect of at least 1000, at least 4000, at least 8000, at least 12000, at least 16000, at least 20000, at least 24000, at least 50000, at least 75000, or up to 90000 compounds or more can be investigated in the multiple PBMC monolayers obtained from such a single sample. In certain embodiments, the monolayers provided herein can be imaged and analyzed using multiple channels simultaneously of high content data. The number of channels of data available is dependent only on the particular imaging software and available staining methodologies, which field rapidly advances. Currently available methodologies allow the simultaneous imaging, processing and analysis of at least two channels, and more typically, 4, 5 or 8 channels of high-content data.

The disclosed methods overcome the dogma that PBMCs and/or bone marrow cells (or other non-adherent cells) cannot be used in such methods. The invention provides, in some aspects, methods and devices allowing the formation of stainable and imageable monolayers of PBMCs or bone marrow cells. In this regard, the inventors surprisingly found that incubating a specific density of PBMCs or bone-marrow cells (i.e. per growth area) leads to the formation of a stainable and imageable monolayer of PBMCs or bone-marrow cells, respectively.

Peripheral blood mononuclear cells (PBMCs) are blood cells having a round nucleus (as opposed to a lobed nucleus). PBMCs comprise lymphocytes (B-cells, T-cells (CD4 or CD8 positive), and NK cells), monocytes (dendritic cell and macrophage precursor), macrophages, and dendritic cells. These blood cells are a critical component in the immune system to fight infection and adapt to intruders. In context of some embodiments of the present invention, it is preferred to use ficoll density gradient purified PBMCs, preferably human PBMCs, for creation of the PBMC monolayer of the invention or the cell-culture device comprising the PBMC monolayer or for use in the methods provided in some aspects of the present invention.

PBMCs cells for use according to the methods described herein can be isolated from whole blood using any suitable method known in the art or described herein. For example, the protocol described by Panda et al. may be used (Panda, S. and Ravindran, B. (2013). Isolation of Human PBMCs. Bio-protocol 3(3): e323). Preferably, density gradient centrifugation is used for isolation. Such density gradient centrifugation separates whole blood into components separated by layers, e.g., a top layer of plasma, followed by a layer of PBMCs and a bottom fraction of polymorphonuclear cells (such as neutrophils and eosinophils) and erythrocytes. The polymorphonuclear cells can be further isolated by lysing the red blood cells, i.e. non-nucleated cells. Common density gradients useful for such centrifugation include, but are not limited to, Ficoll (a hydrophilic polysaccharide, e.g., Ficoll®-Paque (GE Healthcare, Upsalla, Sweden) and SepMate™ (StemCell Technologies, Inc., Köln, Germany).

Bone-marrow cells for use according to the methods described herein can be isolated from bone marrow using any suitable method known in the art. In particular, magnetic beads can be used to separate bone-marrow cells from other components of such samples. For example, MACS cell separation reagents may be used (Miltenyi Biotec, Bergisch Gladbach, Germany).

As is known in the art, such isolated cultures may contain a small percentage of one or more populations of another cell type, e.g., non-nulceated cells such as red blood cells. The PBMCs may be further isolated and/or purified from such other cell populations as is known in the art and/or as described herein; for example, methods of lysing red blood cells is commonly use to remove such cells from the isolated PBMCs. However, the methods of the invention are not reliant on further purification methods, and the isolated PBMCs isolated herein may be directly used. Accordingly, the methods disclosed herein may or may not comprise lysing of red blood cells from within the sample of isolated PBMCs. However, where present, it is believed that the presence of non-nucleated cells, e.g., red blood cells, being generally smaller than PBMCs, settle on the culture surface below and between the PBMCs, and potentially interfere with the formation of a monolayer suitable for imaging. Therefore it is preferred that the concentration of non-nucleated cells, e.g., red blood cells, relative to PMBCs is between about 500 to 1, more preferably about 250 to 1, most preferably about 100 to 1, with the preferential concentration as low as possible. That is, it is most preferred that the isolated PBMC sample according to the methods disclosed herein contains less than about 100 non-nucleated cells, e.g. red blood cells, per PBMC.

In some embodiments of the methods of the invention, PBMCs are incubated subsequently to isolation at a density of about 100 cells per $mm^2$ growth area to about 30000 cells per $mm^2$ growth area. Preferably, the PBMCs are incubated at a density of about 500 cells per $mm^2$ growth area to about 20000 cells per $mm^2$ growth area, about 1000 cells per $mm^2$ growth area to about 10000 cells per $mm^2$ growth area, about 1000 cells per $mm^2$ growth area to about 5000 cells per $mm^2$ growth area, or about 1000 cells per $mm^2$ growth area to about 3000 cells per $mm^2$ growth area. Most preferably the PBMCs are incubated at a density of about 2000 cells per $mm^2$ growth area. The term "about" shall have the meaning of within 10%, more preferably within 5%, of a given value or range. Accordingly, the PBMCs of the invention are, in some embodiments, incubated using methods of the invention to have in the culture device a density of about 100, i.e. from 90 to 110, cells per $mm^2$ growth area to about 30000, i.e. 27000 to 33000, cells per $mm^2$ growth area. More preferably, the PBMCs are incubated at a density of about 500, i.e. 450 to 550, cells per $mm^2$ growth area to about 20000, i.e. 18000 to 22000, cells per $mm^2$ growth area, about 1000, i.e. 900 to 1100, cells per $mm^2$ growth area to about 10000, i.e. 9000 to 11000, cells per $mm^2$ growth area, about 1000, i.e. 900 to 1100, cells per $mm^2$ growth area to about 5000, i.e. 4500 to 5500, cells per $mm^2$ growth area, or about 1000, i.e. 900 to 1100, cells per $mm^2$ growth area to about 3000, i.e. 2700 to 3300, cells per $mm^2$ growth area. Most preferably the PBMCs are incubated at a density of about 2000, i.e. 1800 to 2200, cells per $mm^2$ growth area.

The number of PBMCs can be determined using standard methods known in the art. In particular, the number of PBMCs can be determined by cell counting using a hemocytometer or the method described by Chan et al. (Chan et al. (2013) J. Immunol. Methods 388 (1-2), 25-32). The number of bone-marrow cells can also be determined using methods well known in the art. In particular, bone-marrow cells can be determined using cell counting.

Incubation is carried out in a culture medium. A person skilled in the art is well aware of suitable methods to maintain viability of PBMCs or bone-marrow cells. However, the culture medium to be used in the methods of the invention is not particularly limited. In this regard, medium stands for liquids with nutrients and substances necessary for cultivation of cells. Liquid culture media for culturing eucaryotic cells are known to the person skilled in the art (e.g., DMEM, RPMI 1640, etc). Suitable media may be selected depending on the type of cells to be cultured. For example, PBMCs or bone-marrow cells may be cultivated in RPMI 1640 10% FCS. Any suitable media may be chosen, however, media components should be selected that are known to not artificially influence PBMC response and/or bone-marrow cell response. Supplements describe substances to be added to culture media in order to induce or modify cell function (e.g. cytokines, growth and differentiation factors, mitogens, serum). Supplements are known to the person of skill in the art. One example of a serum commonly used with eukaryotic cells is fetal calf serum. The culture media may further be supplemented with antibiotics, such as penicillin, streptomycin, ciprofloxacin etc. In one embodiment, test substances and/or stimulatory agents may be added to living cell material in each individual unit separately. Test substances may be pharmaceutical drugs or drug components. Stimulators may comprise any of the substances which support maintenance, growth or differentiation of cells. In a particular embodiment, stimulators are substances which act on immune cells, e.g. by activation of immune cells. Stimulators for activation of immune cells are known from the prior art. Such agents may be polypeptides, peptides or antibodies and other stimulators. For example, OKT-3, interferon-alpha, interferon-beta and interferon-gamma, oligoCPGs, mitogens (e.g. PWM, PHA, LPS), etc. Test substances and stimulators may be injected into the cell culture medium. Preferably, PBMCs are cultured in RPMI supplemented with FBS/FCS at 10% (preferably but not necessarily having low endotoxin ratings to minimize activation). PBMC cultures may furthermore comprise human serum from the PBMC donor.

The term "growth area" as used within the meaning of the invention refers to the surface within a culture device upon which cells rest. The "density" as used within the meaning of the invention is the quantity of cells per unit area of the surface within the device upon which the cells rest. The culture device may be produced of any material compatible with cell culture, in particular, non-cytotoxic cell culture tested material. Examples for the material are plastic materials, e.g., thermoplastic or duroplastic materials. Examples of suitable plastics are polyethylene, polypropylene, polysulfone, polycarbonate, polyetherethylketone (PEEK) or polytetrafluorethylene (PTFE). In particular, the device is suitable for the culture and/or maintenance of PBMCs. Typical culture devices known in the art and of use in the invention include culture flasks, dishes, plates, and multi-well plates. Of particular use are multi-well plates, which provide the ability to separately maintain multiple cultures, e.g., for multiple perturbations, with minimal material requirements, e.g., minimal media requirements. Preferred culture devices include 96 well plates, 384 well plates and 1536 well plates. As known in the art in connection with imaging analysis of cultures, in particular, fluorescence imaging, it is particularly preferred to use black wall plates specifically designed for imaging that reduce background fluorescence/background optical interference with minimal light scatter and reduced crosstalk. The culture device may be sterilized.

The device is in particular of use in automated imaging systems and analysis. Thus, it is preferred that the device/culture device is suitable for use in such systems. In a non-limiting example, the culture device may be translucent. Culture dishes and plates of use for imaging, e.g., fluorescent imaging, are well known in the art and are commercially available. A non-limiting example of a commercially available culture plate for use in the practice of the invention is Corning® 384-well, tissue-culture treated black lid, clear bottom plates (Corning Inc., Massachusetts, USA) or Corning® 384 Well Flat Clear Bottom Black Polystyrene TC-Treated Microplates (Product #3712).

Accordingly, the invention provides a device as defined in the immediate above paragraph or at any other section of this description comprising a PBMC monolayer or a bone-marrow cell monolayer. The device is of particular use for the diagnostic methods described herein. Accordingly, provided is the use of the device provided herein in the methods of the present invention. The device of the invention or the device used in the methods of the present invention may comprise flat-bottom wells. Furthermore, the device may comprise coated wells, e.g. wells coated with poly-lysin.

Apart from the growth area of the device, e.g., culture device, culture dish or well, the choice of the device is not particularly limited. However, the device is preferably a culturing device known in the art to be suitable for culturing PBMCs or bone-marrow cells. Because the invention described herein resides, in some aspects, in the provision of a PBMC monolayer, the device must allow the development and maintenance of such a monolayer. The device used to culture bone-marrow cells must allow the development and maintenance of bone-marrow cells and, in particular, allow the formation of the bone-marrow cell monolayer of the invention. Accordingly, round bottom culture devices or v bottom culture devices, which allow and/or promote multi-layer cell cultures, cell pellets and/or cell aggregates are not preferred. Most preferred are flat bottom culture devices, e.g., flat bottom wells in a multi-well plate, which allow and promote a monolayer formation. The culturing device must also be suitable to allow culturing of PBMCs while maintaining a monoloyer. This means that media within the culture device must be able to be removed and/or replaced without or with only minimal disruption of the cell monolayer. Therefore, it is preferred to use culturing devices that allow a 3 to 15 mm high layer of media or solution above the monolayer surface. By maintaining such a minimal layer of media above the cells, the media can be removed or replaced without disruption of the monolayer. To minimize disruption of the monolayer, unnecessary disturbances, e.g., vortexes, within the medium should be avoided. As explained above, such disturbances can be avoided by maintaining a minimal distance between the monolayer and medium surface so that vortexing and/or disturbances that develop at the surface on medium removal/replacement do not penetrate to the lowest medium layers at the monolayer surface. Robotic or other automated aspirators, e.g., pipetting systems, for removing and replacing medium are also of use in the practice of the invention, e.g., to, minimize medium disturbances. Rectangular culture devices, e.g., rectangular wells, are also preferred to minimize such disrupting effects, e.g. vortexes. The culture device comprises a plurality of culture units comprising each a culture chamber. There are no particular limitations as to the arrangement of culture units, and culture chamber may be in a miniaturized format provided that the requirements for reduction of medium disruptions as explained herein are maintained. For example, as recognized in the art, at the small volumes used in multi-well plates, e.g., 384 well plates, liquid disturbances may result from changes in surface tension forces, e.g. changes in the meniscus. These changes may be the result of, e.g., changes in medium-level due to evaporation, which changes may result from unexpected causes. Thus, evaporation from the cell culture device should be avoided or minimized. Therefore, the culture chamber may be reversibly closed on the top by a lid. The lid may be a cover covering several culture chambers. Alternatively, individual culture chambers may be individually closed, e.g., by cover slides or by a polymer film.

The culture chamber may be translucent for allowing microscopic inspection of cells present in the culture chamber. The culture chamber may have a grooved or a flat bottom side. The latter is particularly suited for allowing microscopic inspection of cells present in the culture chamber and is thus preferred. As known in the art in connection with imaging analysis of cultures, in particular, fluorescence imaging, it is also particularly preferred to use black wall plates specifically designed for imaging that reduce background fluorescence/background optical interference with minimal light scatter and reduced crosstalk.

The culture device (e.g., including but not limited to a culture chamber, flask, dish, plate, multi-well plate) may or may not be coated and/or treated so as to promote cell adhesion. As known in the art, cell and/or tissue culture devices may be treated so that one or more surfaces of the device promote cell adhesion; similarly, as is also known in the art, the culture device may alternately or additionally be coated with molecules or compounds that promote cell adhesion to one or more surfaces of the device. However, the methods of the invention are not reliant on the coating or treatment of the culture device. Thus, the invention encompasses use of cell culture devices which are not treated or coated to promote cell adhesion. The invention also encompasses a cell culture device which is not treated or coated so as to promote cell adhesion comprising a PBMC monolayer. In some embodiments, a PBMC monolayer may be cultured on a device that is not treated or coated so as to promote cell adhesion (as used herein, and throughout this disclosure, the term "cultured" in reference to the PBMC monolayer does not imply any necessary minimal time; PBMCs isolated from a sample, placed in a cell culture device and imaged are considered to be cultured on or in the device regardless of the length of time the cells have been on or in the device).

Nevertheless, the invention does not exclude the use of culture devices that have been treated and/or coated to promote cell adhesion on one or more surfaces. In this regard, the invention also encompasses use of cell culture devices which are treated or coated to promote cell adhesion. The invention further encompasses a cell culture device which is or has been treated or coated so as to promote cell adhesion comprising a PBMC monolayer. The invention further may be directed to a PBMC monolayer cultured on a device that is or has been treated or coated so as to promote cell adhesion. Treatments or coating agents that promote cell adhesion are well known in the art. Non-limiting examples of known adhesion agents include, but are not limited to, polylysine, fibronectin or gelatin. Furthermore, the culture device (e.g., including but not limited to a culture chamber, flask, dish, plate, multi-well plate) may be suitable for use in a sandwich-ELISA method, wherein e.g. PBMCs are adhered to the culture chamber surface by adhesion molecules attached to the culture chamber surface.

It is preferred to use a culturing plate. Culturing plates preferably used in the methods of the invention have a bottom area for growth ("growth area") of about 0.32 cm$^2$ or less. Typical culturing plates are thus plates having 96-wells or more.

It is particularly preferred to use well plates with a growth area of about 5.6 mm$^2$ to about 10 mm$^2$ per well. Thus, any multi-well plate offering a growth surface between these values is also encompassed by the methods of the invention. As disclosed further above, the number of PBMCs per growth area is preferably within the range of about 100 to about 30000 PBMCs per mm$^2$ of growth area, preferably, the PBMCs are incubated at a density of about 500 cells per mm$^2$ growth area to about 20000 cells per mm$^2$ growth area, about 1000 cells per mm$^2$ growth area to about 10000 cells per mm$^2$ growth area, about 1000 cells per mm$^2$ growth area to about 5000 cells per mm$^2$ growth area, or about 1000 cells per mm$^2$ growth area to about 3000 cells per mm$^2$ growth area. Most preferably the PBMCs are incubated at a density of about 2000 cells per mm$^2$ growth area. The term "about" shall have the meaning of within 10%, more preferably within 5%, of a given value or range. Accordingly, the PBMCs of the invention are incubated to have in the culture device a density of about 100, i.e. from 90 to 110, cells per mm$^2$ growth area to about 30000, i.e. 27000 to 33000, cells per mm$^2$ growth area. More preferably, the PBMCs are incubated at a density of about 500, i.e. 450 to 550, cells per mm$^2$ growth area to about 20000, i.e. 18000 to 22000, cells per mm$^2$ growth area, about 1000, i.e. 900 to 1100, cells per mm$^2$ growth area to about 10000, i.e. 9000 to 11000, cells per mm$^2$ growth area, about 1000, i.e. 900 to 1100, cells per mm$^2$ growth area to about 5000, i.e. 4500 to 5500, cells per mm$^2$ growth area, or about 1000, i.e. 900 to 1100, cells per mm$^2$ growth area to about 3000, i.e. 2700 to 3300, cells per mm$^2$ growth area. Most preferably the PBMCs are incubated at a density of about 2000, i.e. 1800 to 2200, cells per mm$^2$ growth area.

Therefore, for example, in a cell with 10 mm$^2$ growth area, i.e. a typical 384 well-plate, the number of PBMCs per well is preferably in the range of about 1000 to about 300000 PBMCs, more preferably of about 5000 to about 200000 PBMCs, more preferably of about 10000 to about 100000 PBMCs, even more preferably of about 10000 to about 50000 PBMCs and most preferably is about 20000 PBMCs per well. The term "about" shall have the meaning of within 10%, more preferably within 5%, of a given value or range. Accordingly, the number of PBMCs per well is preferably in the range of 1000, i.e. 900 to 1100, to 300000, i.e. 270000 to 330000, more preferably in the range of 5000, i.e. 4500 to 5500, to 200000, i.e. 180000 to 220000, more preferably in the range of 10000, i.e. 9000 to 11000, PBMCs to 100000, i.e. 90000 to 110000, PBMCs, most preferably in the range of 20000, i.e. 18000 to 22000, PBMCs.

The concentration of the PBMCs in solution prior to inoculation or seeding of the wells is not critical so long as the concentration allows the correct number of cells to be introduced into the well (i.e., at a growth surface density as described herein) while maintaining the minimal amount of liquid/medium overlay as also described herein (i.e., an overlay of between 3 to 15 mm above the monolayer surface). Suitable concentrations of PBMC solutions for inoculation include, but are not limited to, solutions containing between about 20 and about 6000 PBMCs per µl growth medium. It is preferred that the concentration of PBMCs is about 3000 PBMCs per µl growth medium, more preferably 1500 PBMCs per µl, more preferably 1000 PBMCs per µl. A concentration of about 400 PBMCs per µl growth medium is most preferred.

"Incubation" of the PBMCs within the meaning of the present invention is done by methods well-known in the art. For example, the method described by Panda et al. may be used (Panda, S. and Ravindran, B. (2013). *In vitro Culture of Human PBMCs. Bio-protocol* 3(3): e322). The culture conditions are defined by culture media, supplements, matrices, technically supported micro-environment and gas supply. Individual culture units may provide comparable conditions. The culture conditions may be chosen according to the type of cells. For example, cells may be incubated at 37° C., 5% $CO_2$ and 20% oxygen. The cultured cells may be provided with gas through a gas permeable membrane that seals at least one side of the culture chamber.

Preferably, PBMCs are incubated at 37° C. in a $CO_2$ incubator with 5% $CO_2$. It is preferred to use RPMI as culture medium. The duration of the incubation step of the methods of the invention is not particularly limited. However, as recognized in the art, isolated PBMCs represent a fragile cell population that are difficult to maintain over the long term; culturing times of over 36 hours are likely to result in the beginning cell death. Accordingly, where incubation times of over 36 hours are to be used, the health of the culture should be monitored to ensure that the monolayers remain viable. Typically, cultures are cultured for between 1 and 24 hours (e.g., overnight) which ensures that PBMC monolayers remain viable. However, formation of an imageable PBMC monolayer, which may or may not be stained according to methods known in the art and/or described herein (comprising both adherent and non-adherent subpopulations of PBMCs) is typically accomplished after short incubation, e.g., less than 1 hour. Where the PBMC monolayers are used in methods of the invention comprising the assessment of response to a therapeutic agent, longer incubation periods may be required to allow the agent to exert its activity and/or for an observable effect to be achieved (however, the cells must remain viable during this incubation, and, as explained herein, these longer incubation periods typically are at most 24 hours). Furthermore, the PBMC monolayer comprises both, healthy and diseased cells which can subsequently be used for further analysis.

In order to increase stability of the PBMC monolayer or bone-marrow cell monolayer subsequent to culture for further analysis, the practice of the invention may comprise a step of fixing the PBMCs or bone-marrow cells where the monolayers are stained and/or subsequently imaged. Fixing can be done by means and methods well-known to a person skilled in the art. For example, the PBMC monolayer can be fixed on the bottom area of the culturing device using formaldehyde or other known fixatives. Fixing is normally performed immediately prior to the addition of the means for visualizing the cells, cell components, and/or cellular proteins. If desired, a detergent can be added for cell permeabilization. An exemplary detergent is Triton X-114 for permeabilization. Because the invention, in part, relies on a PBMC monolayer, fixation and/or permeabilization must be implemented so as not to destroy the monolayer. In this respect, the practices described for removing and/or replacing medium can also be implemented for use of fixatives and/or permeabilizers. As the skilled person appreciates, subsequent to fixation, the monolayer will be more robust, i.e., resistant to disruption, e.g., from liquid forces. Accordingly, the present invention provides a method for culturing PBMCs or bone-marrow cells comprising (a) isolating PBMCs from a blood sample or bone-marrow cells from bone-marrow; (b) incubating PBMCs or bone-marrow cells at a density of about 100 cells per $mm^2$ to about 30000 cells per $mm^2$; and (c) fixing said PBMCs or bone-marrow cells.

The methods of the invention may further comprise a step of adding a dye prior to fixation, e.g. a viability dye. This may be done in order to verify that the cells in the PBMC monolayer or bone-marrow cell monolayer are viable. Adding a dye, e.g. a viability dye, may be done by e.g. partially removing the supernatant and adding a dye, e.g. a viability dye, known to be suitable for visualizing the viability of PBMCs or bone-marrow cells. In particular, a viability dye may be added which can distinguish between live and dead PBMCs or bone-marrow cells to determine the viability of cells prior to the fixation and/or permeabilization required for the optional intracellular antibody staining or prior to elimination of biohazardous materials using formaldehyde fixation. Viability stain is based on the dynamic incorporation of the dye as a labeling agent into the cell membrane or cell organelles, or conversion of a dye precursor by cell enzymes or by detecting intermediates of the respiratory chain, or by intercalation in DNA or RNA. A person skilled in the art is well aware that dyes suitable for visualizing fixed PBMCs or bone-marrow cells may also be used. Suitable dyes and their application protocols are known to the skilled person and documented, for example, in the Molecular Probes Handbook, A Guide to Fluorescent Probes and Labeling Technologies. As a non-limiting example, the viability dye may be added in a 1:1000 mix dissolved in isotonic solution, e.g. PBS. In this regard, invitrogen live/dead fixable 488 dye is particularly useful. Accordingly, the present invention provides a method for culturing PBMCs or bone-marrow cells comprising (a) isolating PBMCs from a blood sample or bone-marrow cells from bone-marrow; (b) incubating PBMCs or bone-marrow cells at a density of about 100 cells per $mm^2$ to about 30000 cells per $mm^2$; and (c) adding a viability dye to said PBMCs or bone-marrow cells.

The monolayers of the invention may be imaged according to any methods known in the art and/or described herein. The particular imaging method is not critical and may be decided according to the knowledge of the person of skill in the art. The imaging may or may not require the use of a dye or stain, may comprise imaging of both stained and non-stained components and/or may comprise imaging under conditions wherein the stain is or is not visible (e.g., imaging in bright-field (wherein a fluorescent stain would not be visible) and under uv-lighting (wherein a fluorescent stain would be visible), or combinations thereof. Imaging under bright-field conditions is well known and routine used in the art, and may be performed according to standard methods and/or as described herein. Additionally or alternatively, any other label-free imaging may be used in accordance with the invention. Such label-free methods are known and include, e.g., PhaseFocus imaging (Phase Focus Ltd, Sheffield, UK).

The practice of the invention may also comprise the addition of a detectable label to the PBMC monolayers (either in connection with label-free methods or independently), which label may be detected using microscopic methods. The detectable labels may label discrete cellular structures, components or proteins as known in the art. The label may also be attached to antibodies to specifically label and allow the detection of the antibody antigen. In a preferred embodiment, the detectable label allows visualization of the label under visible or ultra-violet light. Thus the detectable label may be fluorescent. A multitude of visual labels are known in the art and are suitable for the invention. The labels may be detectable without further action, or may only become detectable after performance of a secondary step, e.g., addition of a substrate, exposure to enzymatic reactions, or exposure to specific light wavelengths.

PBMC subpopulations (target cells) or bone-marrow cell subpopulations may be identified by detectable labels via expression of one or more markers on the surface of the target cell or inside of the cell. Alternatively or additionally, subpopulations of the PBMC cells may be defined by the lack of expression of one or more markers on the surface of the target cell or inside the target cell. It may be desirable to test for expression or lack of expression of one or more markers (e.g., two markers, three markers, four markers, etc.) to provide further assurance that a cell expressing or not expressing a marker is in fact a target cell, e.g., a member of desired subclass of PBMC cell. For example, a "cocktail" of antibodies to different markers may be each coupled (whether directly or indirectly) to the same label or to different labels. As an example, a cocktail of antibodies to different markers may each contain a binding motif that binds the same label (e.g., each may contain an Fc of the same species that is recognized by the same secondary antibody, or each may be biotinylated and specifically bound by the same avidin-coupled label). Optionally, two or more different antibodies or cocktails of antibodies may be utilized. Preferably the cells are stained using at least two labels that can be distinguished from one another, thereby permitting identification of cells that express at least two different markers of the target cell types. Cells may also be stained using at least three, four, five, or more different labels that can be distinguished from one another, thereby permitting detection of cells that express greater numbers of markers of the target cell type. Optionally, a cell may be identified as a cell of the target type if it expresses a preselected number of markers or certain preselected combinations of markers or a cell may be identified as a cell of the target type if it does not express a preselected marker. Additionally, it is not necessary that the marker(s) of the target cell type be unique to the target cells, as long as they permit distinction of the target cells from other cells in the population. Major PBMC cell populations are represented by CD11C for dendritic cells, CD14 for macrophages, CD3 (CD4 or CD8 with CD3) for T-cells and CD19 for B-cells. While the foregoing markers overlap on subsets of these major classes of PBMCs, staining with these markers for identifying subpopulations of PBMCs is widely accepted in the field. Further markers suitable for use in methods of the present disclosure may be found in the CD marker handbook (Becton, Dickinson and Co. 2010, CA, USA). Major cell subpopulations comprised in bone-marrow cells are neutrophilic metamyelocytes, neutrophilic myelocytes, segmented neutrophils, normoblasts and lymphocytes.

It is preferred to use antibodies conjugated to detectable labels in the practice of the invention. Such antibodies allow the targeting of discrete cellular structures and, thus, cocktails of such antibodies (each bearing a different label) may be used to simultaneously visualize multiple targets/cellular structures/cellular components. Again because the invention relies on a PBMC monolayer, care must be taken during staining to avoid monolayer disruption. As the skilled person appreciates, this is particularly problematic with the use of antibody-based labels, as their use normally requires one or more wash-steps to eliminate unbound label that would interfere with accurate visualization, i.e., would result in non-specific staining and/or assay "noise". Accordingly, the invention encompasses methods for the staining of PBMC monolayers with a detectable label, in particular, an antibody-based label, which minimizes or eliminates washing requirements subsequent to staining. The methods of the invention may comprise adding the detectable label(s) at concentrations that avoid generation of noise signal in the absence of washing, which can be determined by methods well known in the art and/or described herein. Thus, the invention encompasses the use of labeled antibodies at concentrations above or below that recommended by the antibody manufacturers.

Accordingly, the present invention provides a method for culturing PBMCs or bone-marrow cells comprising (a) isolating PBMCs from a blood sample or bone-marrow cells from bone-marrow; (b) incubating PBMCs or bone-marrow cells at a density of about 100 cells per mm$^2$ to about 30000 cells per mm$^2$; (c) fixing said PBMCs or bone-marrow cells, and (d) adding a detectable label to the fixed PBMCs/bone-marrow cells. Preferably, the detectable label used in step (d) is an antibody.

For some exemplary cell types, cells may only be considered positive for a given marker if that marker exhibits a characteristic localization or pattern within the cell. For instance, a cell may be considered "positive" if a cytoskeletal marker is present in the cytoskeleton and "negative" if there is some diffuse cytoplasmic staining. In such a case, cells may be cultured under suitable conditions (e.g., as adherent cultures) to establish the characteristic localization or pattern within the cell. Suitable culture conditions and time for cytoskeleton assembly (or other processes to establish subcellular organization) that may be necessary for robust detection of a given marker are readily determined by those of ordinary skill in the art. Additionally, markers may readily be chosen which decrease or eliminate the need for adherent culture as a precondition to robust staining.

Dyes useful in labeling proteins are known in the art. In general, a dye is a molecule, compound, or substance that can provide an optically detectable signal, such as a colorimetric, luminescent, bioluminescent, chemiluminescent, phosphorescent, or fluorescent signal. In a preferred embodiment of the invention, the dye is a fluorescent dye. Non-limiting examples of dyes, some of which are commercially available, include CF dyes (Biotium, Inc.), Alexa Fluor dyes (Invitrogen), DyLight dyes (Thermo Fisher), Cy dyes (GE Healthscience), IRDyes (Li-Cor Biosciences, Inc.), and HiLyte dyes (Anaspec, Inc.). In some embodiments, the excitation and/or emission wavelengths of the dye are between 350 nm to 900 nm, or between 400 nm to 700 nm, or between 450-650 nm.

For example, staining may comprise using multiple detectable labels, e.g. antibodies, self-antibodies or patient serum. A stain may be observable under visible light and under ultraviolet light. A stain may comprise an antibody directly or indirectly coupled to a colored reagent or an enzyme capable of producing a colored reagent. When antibodies are used as a component of a stain, a marker can be directly or indirectly coupled to the antibody. Examples of indirect coupling include avidin/biotin coupling, coupling via a secondary antibody, and combinations thereof. For example, cells may be stained with a primary antibody that binds a target-specific antigen, and a secondary antibody that binds the primary antibody or a molecule coupled to the primary antibody can be coupled to a detectable marker. Use of indirect coupling can improve signal to noise ratio, for example by reducing background binding and/or providing signal amplification.

The stain may also comprise a primary or secondary antibody directly or indirectly coupled (as explained above) to a fluorescent label. The fluorescent label may be selected from the group consisting of: Alexa Fluor 350, Alexa Fluor 405, Alexa Fluor 430, Alexa Fluor 488, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750 and Alexa Fluor 790, fluoroscein isothiocyanate (FITC), Texas Red, SYBR Green, DyLight Fluors, green fluorescent protein (GFP), TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, TET (6-carboxy-2',4,7, 7'-tetrachlorofluorescein), HEX (6-carboxy-2',4,4',5',7,7'-hexachlorofluorescein), Joe (6-carboxy-4',5'-dichloro-2',7'-dimethoxyfluorescein) 5-carboxy-2',4',5',7'-tetrachlorofluorescein, 5-carboxyfluorescein, 5-carboxy rhodamine, Tamra (tetramethylrhodamine), 6-carboxyrhodamine, Rox (carboxy-X-rhodamine), R6G (Rhodamine 6G), phthalocyanines, azomethines, cyanines (e.g. Cy3, Cy3.5, Cy5), xanthines, succinyifluoresceins, N,N-diethyl-4-(5'-azobenzotriazolyl)-phenylamine, aminoacridine, and quantum dots.

Further exemplary embodiments of the present method utilize antibodies directly or indirectly coupled to a fluorescent molecule, such as ethidium bromide, SYBR Green, fluorescein isothiocyanate (FITC), DyLight Fluors, green fluorescent protein (GFP), TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, TET (6-carboxy-2',4,7,7'-tetrachlorofluorescein), HEX (6-carboxy-2',4,4',5',7,7'-hexachlorofluorescein), Joe (6-carboxy-4',5'-dichloro-2',7'-dimethoxyfluorescein) 5-carboxy-2',4',5',7'-tetrachlorofluorescein, 5-carboxyfluorescein, 5-carboxy rhodamine, Tamra (tetramethylrhodamine), 6-carboxyrhodamine, Rox (carboxy-X-rhodamine), R6G (Rhodamine 6G), phthalocyanines, azomethines, cyanines (e.g. Cy3, Cy3.5, Cy5), xanthines, succinyifluoresceins, N,N-diethyl-4-(5'-azobenzotriazolyl)-phenylamine and aminoacridine. Other exemplary fluorescent molecules include quantum dots, which are described in the patent literature [see, for example, U.S. Pat. Nos. 6,207,299, 6,322,901, 6,576,291, 6,649,138 (surface modification methods in which mixed hydrophobic/hydrophilic polymer transfer agents are bound to the surface of the quantum dots), U.S. Pat. Nos. 6,682, 596, 6,815,064 (for alloyed or mixed shells), each of which patents is incorporated by reference herein)], and in the technical literature [such as "Alternative Routes toward High Quality CdSe Nanocrystals," (Qu et al., Nano Lett., 1(6):333-337 (2001)]. Quantum dots having various surface chemistries and fluorescence characteristics are commercially available from Invitrogen Corporation, Eugene, Oreg., Evident Technologies (Troy, N.Y.), and Quantum Dot Corporation (Hayward, Calif.), amongst others. Quantum dot" also includes alloyed quantum dots, such as ZnSSe, ZnSeTe, ZnSTe, CdSSe, CdSeTe, ScSTe, HgSSe, HgSeTe, HgSTe, ZnCdS, ZnCdSe, ZnCdTe, ZnHgS, ZnHgSe, ZnHgTe, CdHgS, CdHgSe, CdHgTe, ZnCdSSe, ZnHgSSe, ZnCdSeTe, ZnHgSeTe, CdHgSSe, CdHgSeTe, InGaAs, GaAlAs, and InGaN. Alloyed quantum dots and methods for making the same are disclosed, for example, in US Application Publication No. 2005/0012182 and PCT Publication WO 2005/001889.

Subsequent to labeling the PBMC monolayer or bone-marrow cell monolayer of the invention, the method may further comprise detecting the signal of the detectable label. Depending on the kind of signal emitted by the detectable label, the detection method may be appropriately adapted. It is preferred to use a detection method suitable for detecting fluorescent light emitting labels. The detection method may also be automated according to standard methods known in the art. For example, various computational methods exist that enable a person skilled in the art to analyze and interpret the microscopy images of PBMCs or bone-marrow cells obtained by pharmacoscopy or to establish automated protocols for their analysis. For primary image analysis, including the correction for illumination bias in microscopy images, the identification of individual cells from microscopy images and the measurement of marker intensities and textures as well as nuclear and cellular size and shape parameters, the opensource software CellProfiler (e.g. version 2.1.1) can be used. Identification of marker-positive cells (such as CD34+ progenitor cells or viability dye positive cells) can be performed by machine learning using the opensource software CellProfiler Analyst (e.g. version 2.0) and double- or triple-positive cells can be identified by a sequential gating strategy. Plate-overviews for further analysis and hit selection can be created using CellProfiler Analyst as well.

The cell HTS package in Bioconductor (e.g. version 2.14), or Pipeline Pilot (e.g. version 9.0; Accelrys), can both be used for the data analysis subsequent to the primary image analysis, including plate-effect normalization, control-based normalization, and hit selection.

Commercial automated microscopy systems may also be used in the practice of the invention, e.g., PerkinElmer Operetta automated microscope (PerkinElmer Technologies GmbH & Co. KG, Walluf, Germany), which systems may include corresponding image analysis software, e.g., PerkinElmer's Harmony software (e.g. version 3.1.1). Such automated and/or commercial systems can be used to perform primary image analysis, positive cell selection and hit selection from microscopic images according to the methods of the invention.

The invention furthermore provides, a PBMC monolayer for use in determining whether the PBMC donor suffers from a disease or is predisposed to suffer from a disease. It is one surprising advantage of the disclosed PBMC monolayer and methods using the same that both healthy and diseased PBMCs are comprised in the monolayer. "Diseased PBMCs" within the meaning of the invention relate to PBMCs being affected by a disease and thus distinguishable from healthy PBMCs. In particular, in some embodiments, a diseased PBMC will show differential expression of marker molecules that enable their specific detection using the methods of the present invention. For example, a diseased PBMC may show expression of known cancer markers, in particular markers for lymphoma or leukemia, which enable their detection and discrimination from healthy PBMCs.

The invention furthermore provides a bone-marrow cell monolayer for use in determining whether the bone-marrow cell donor suffers from a disease or is predisposed to suffer from a disease.

In some embodiments, in addition to healthy and diseased PBMCs or healthy and diseased bone-marrow cells, both adherent and non-adherent cells are present in the monolayers of the invention. Therefore, the methods of the invention may provide unique advantages over methods known in the art, by allowing to obtain a total overview of the current status with regard to the presence or absence of subpopulations of PBMCs or bone-marrow cells and/or the distribution of different subpopulations in the blood of the PBMC donor or the bone-marrow cell donor. In contrast, methods known in the art rely on prior isolation of subpopulations thereby neglecting the information contained in cell-cell interactions between different subpopulations. The PBMC monolayer of the invention and as, e.g., produced by the methods of the invention, can thus be used in some embodiments for determining whether the PBMC donor suffers from a disease or has a predisposition for a disease by adding a detectable label to the PBMC monolayer which is specific for a cell type indicative for the presence of a disease or by determining altered ratios among the various subpopulations of the PBMC cells, which ratios are indicative of the disease or predisposition for the disease. Accordingly, the present invention also provide, in some aspects, for a method for diagnosing a disease or predisposition to a disease in a PBMC donor comprising the PBMCs cultured according to any of the methods of the invention. The PBMC monolayer of the invention and the methods of the invention may thus also be used for following the course of a disease during treatment of a disease or in the absence of treatment.

The bone-marrow cell monolayer of the invention and as, e.g., produced by the methods of the invention, can thus be used in some embodiments for determining whether the bone-marrow cell donor suffers from a disease or has a predisposition for a disease by adding a detectable label to the bone-marrow cell monolayer which is specific for a cell type indicative for the presence of a disease or by determining altered ratios among the various subpopulations of the bone-marrow cells, which ratios are indicative of the disease or predisposition for the disease. Accordingly, the present invention also provide, in some aspects, for a method for diagnosing a disease or predisposition to a disease in a bone-marrow cell donor comprising the bone-marrow cells cultured according to any of the methods of the invention. The bone-marrow cell monolayer of the invention and the methods of the invention may thus also be used for following the course of a disease during treatment of a disease or in the absence of treatment.

The method includes isolating PBMCs or bone-marrow cells from a subject previously or currently treated for an immune mediated disease, stimulating the PBMCs or bone-marrow cells, identifying subpopulations of PBMCs or bone-marrow cells, comparing data from the PBMC sub-populations or bone-marrow cell subpopulations to a subject response to the therapeutic and selecting a signature marker profile related to a positive response to the therapeutic, thereby monitoring the course of therapy.

Immune mediated diseases can be divided into several categories including immunodeficiency diseases, autoimmune diseases and hypersensitivity diseases. Immunodeficiency diseases occur when part of the immune system is not functioning properly. Autoimmune diseases are the result of the immune system attacking the body instead of pathogens. Hypersensitivity diseases occur when the immune system over reacts and results in damage to the body.

The disease to be diagnosed using the PBMC monolayer or the bone-marrow cell monolayer of the invention or the methods of the invention is not particularly limited as long as it can be diagnosed using PBMCs or bone-marrow cells, respectively, i.e. a subject having the disease to be diagnosed shows an altered cellular pattern of PBMCs or bone-marrow cells that can be associated with the disease, e.g., ratios of PBMC sub-populations or bone-marrow cell subpopulations that are altered from those expected in a healthy donor. For example, diseases that can be diagnosed using the monolayers of the invention and/or the methods of the invention include but are not limited to hematologic malignancies and/or a malignancy of myeloid and/or lymphoid tissue. Diseases that are in particular diagnosable and/or predictable by the PBMC monolayer or bone-marrow cell monolayer of the invention and the methods of the invention include, but are not limited to, myeloproliferative disorders (or general blood cancers), inflammatory disorders, latent virus infections, cellular growth disorders, cellular chemotaxis disorders, metabolic disorders, autoimmune disorders (e.g., staining with self ligand or patient serum for clonal antibodies or self antigen recognition). Moreover, the PBMC monolayer and methods of the invention can be used to diagnose leukemia (chronic and acute), lymphoma (mature B-cell, mature T- and NK cell, Hodgkin's lymphoma), HIV, gout, shock and the like.

The present invention furthermore provides for methods for determining whether a subject suffering from or predisposed to a disease will respond or is responsive to treatment with a therapeutic agent. According to the present invention, the method may comprise the steps of (a) isolating PBMCs from a blood sample obtained from said subject; (b) incubating said PBMCs at a density of about 100 cells per $mm^2$ to about 30000 cells per $mm^2$; (c) contacting said PBMCs with said therapeutic agent; and (d) assessing the response of the PBMCs to the therapeutic agent. Preferably, the PBMCs are incubated in step (b) at a density of about 500 cells per $mm^2$ growth area to about 20000 cells per $mm^2$ growth area, about 1000 cells per $mm^2$ growth area to about 10000 cells per $mm^2$ growth area, about 1000 cells per $mm^2$ growth area to about 5000 cells per $mm^2$ growth area, or about 1000 cells per $mm^2$ growth area to about 3000 cells per $mm^2$ growth area. Most preferably the PBMCs are incubated at a density of about 2000 cells per $mm^2$ growth area. The term "about" shall have the meaning of within 10%, more preferably within 5%, of a given value or range. Accordingly, in some embodiments, the PBMCs of the invention are incubated in methods of the invention to have in the culture device a density of about 100, i.e. from 90 to 110, cells per $mm^2$ growth area to about 30000, i.e. 27000 to 33000, cells per $mm^2$ growth area. More preferably, the PBMCs are incubated at a density of about 500, i.e. 450 to 550, cells per $mm^2$ growth area to about 20000, i.e. 18000 to 22000, cells per $mm^2$ growth area, about 1000, i.e. 900 to 1100, cells per $mm^2$ growth area to about 10000, i.e. 9000 to 11000, cells per $mm^2$ growth area, about 1000, i.e. 900 to 1100, cells per $mm^2$ growth area to about 5000, i.e. 4500 to 5500, cells per $mm^2$ growth area, or about 1000, i.e. 900 to 1100, cells per $mm^2$ growth area to about 3000, i.e. 2700 to 3300, cells per $mm^2$ growth area. Most preferably the PBMCs are incubated at a density of about 2000, i.e. 1800 to 2200, cells per $mm^2$ growth area.

"Treatment" or "treating" refers to both therapeutic treatment and prophylactic or preventative measures, wherein the object is to prevent, ameliorate or slow down (lessen) the targeted pathologic condition or disorder, or one or more symptom associated therewith. Similarly, "responsive to" or "responds" and analogous terms refer to indications that the targeted pathological condition, or one or more symptom associated thereof, is prevented, ameliorated or lessened. The terms are also used herein to denote delaying the onset of, inhibiting (e.g. reducing or arresting the growth of), alleviating the effects of, or prolonging the life of a patient suffering from a disease, in particular a myeloproliferative disease, or indications that such markers have been accomplished. Those in need of treatment include those diagnosed with the disorder, those suspected of having the disorder, those predisposed to have the disorder as well as those in whom the disorder is to be prevented. Hence, the mammal to be treated herein may have been diagnosed as having the disorder or may be predisposed or susceptible to the disorder.

"Response" or "responsive" refers to a PBMC or a subject showing at least one altered characteristic subsequent to treatment. The altered characteristic of the subject may be amelioration or slowing down of the targeted pathologic condition or disorder.

As used herein, the terms "prevent", "preventing" and "prevention" refer to the prevention of the occurrence and/or recurrence or onset of one or more symptoms of a cancer disease in a subject resulting from the administration of a prophylactic or therapeutic agent.

The means and methods provided herein are described for primary hematopoietic cells. As the skilled person understands, primary hematopoietic cells comprise, inter alia, PBMCs and bone-marrow cells. Accordingly, the means and methods provided herein, which are described for PBMCs, are also disclosed for bone-marrow cells.

In this regard, the present invention can offer, in various embodiments, multiple advantages over methods of the prior art. In particular, blood samples are preferably treated shortly after isolation, which has several advantages: drug specificity and toxicity to, e.g., cancer cells is directly compared to that of the healthy cells from the patient, and complex aspects of drug responses can be measured that arise from the cell-cell interactions present in human blood. This ex-vivo analysis is a strong predictor of the clinical response of the patient, especially in complex genetic backgrounds, improving long-term therapeutic benefits. For example, drug responses of myeloproliferative neoplasms (MPN) patients to single and combinatorial treatments of current and promising anti-cancer agents can be assessed. Furthermore, simultaneously measuring MPN-specific biomarkers, such as the expression and localization of pSTAT5, and the viability of CD34+ progenitors in the periphery is assessable by the methods of the invention. In addition, it is possible for future patients to have their drug responses characterized at several stages during the course of a disease. Accordingly, the present invention also provides, in some aspects, a PMBC monolayer for use in a diagnostic method for determining whether a subject suffering from or predisposed to a disease will respond or is responsive to treatment with a therapeutic agent.

"Therapeutic agents" within the meaning of the invention are molecules including, without limitation, polypeptides, peptides, glycoproteins, nucleic acids, synthetic and natural drugs, peptoides, polyenes, macrocytes, glycosides, terpenes, terpenoids, aliphatic and aromatic compounds, and their derivatives. In a preferred embodiment, the therapeutic agent is a chemical compound such as a synthetic and natural drug. In another preferred embodiment, the therapeutic agent effects amelioration and/or cure of a disease, disorder, pathology, and/or the symptoms associated therewith. The polymers may encapsulate one or more therapeutic agents.

Suitable therapeutic agents include, without limitation, those presented in Goodman and Oilman's The Pharmacological Basis of Therapeutics (e.g., 9th Ed.) or The Merck Index (e.g., 12th Ed.). Genera of therapeutic agents include, without limitation, drugs that influence inflammatory responses, drugs that affect the composition of body fluids, drugs affecting electrolyte metabolism, chemotherapeutic agents (e.g., for hyperproliferative diseases, particularly cancer, for parasitic infections, and for microbial diseases), antineoplastic agents, immunosuppressive agents, drugs affecting the blood and blood-forming organs, hormones and hormone antagonists, vitamins and nutrients, vaccines, oligonucleotides and gene therapies. It will be understood that compositions comprising combinations, e.g. mixtures or blends of two or more active agents, such as two drugs, are also encompassed by the invention.

In one embodiment the therapeutic agent may be a drug or prodrug, antibody or vaccine. The method of the invention may be used to assess whether administration of a therapeutic agent to a patient triggers a response to the therapeutic agent, or a component of a delivery vehicle, excipient, carrier etc. administered with the therapeutic agent.

The precise nature of the therapeutic agent is not limiting to the invention. In non-limiting embodiments the method of the invention may be used to assess response to synthetic small molecules, naturally occurring substances, naturally occurring or synthetically produced biological agents, or any combination of two or more of the foregoing, optionally in combination with excipients, carriers or delivery vehicles.

The term "diagnosis" (along with grammatical variations thereof such as "diagnosing" or "diagnostic") refers to the identification of a molecular or pathological state, disease or condition, such as the identification of cancer, or refers to the identification of a cancer patient who may benefit from a particular treatment regimen.

The term "prognosis" (and grammatical variations thereof such as "prognosing" or "prognostic") refers to the prediction of the likelihood of benefit from a treatment such as a cancer therapy.

The term "prediction" or "predicting" is used herein to refer to the likelihood that a patient will respond either favorably or unfavorably to a particular therapeutic agent. In one embodiment, prediction or predicting relates to the extent of those responses. In one embodiment, the prediction or predicting relates to whether and/or the probability that a patient will survive or improve following treatment, for example treatment with a particular therapeutic agent, and for a certain period of time without disease progression.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

The general methods and techniques described herein may be performed according to conventional methods well known in the art and as described in various general and more specific references that are cited and discussed throughout the present specification unless otherwise indicated. See, e.g., Sambrook et al., *Molecular Cloning: A Laboratory Manual*, 2d ed., Cold Spring Harbor Laboratory Press, Cold Spring Harbor, N.Y. (1989) and Ausubel et al., *Current Protocols in Molecular Biology*, Greene Publishing Associates (1992), and Harlow and *Lane Antibodies: A Laboratory Manual*, Cold Spring Harbor Laboratory Press, Cold Spring Harbor, N.Y. (1990).

While aspects of the invention are illustrated and described in detail in the drawings and foregoing description, such illustration and description are to be considered illustrative or exemplary and not restrictive. It will be understood that changes and modifications may be made by those of ordinary skill within the scope and spirit of the following claims. In particular, the present invention covers further embodiments with any combination of features from different embodiments described above and below.

The invention also covers all further features shown in the figures individually, although they may not have been described in the previous or following description. Also, single alternatives of the embodiments described in the figures and the description and single alternatives of features thereof can be disclaimed from the subject matter of the other aspect of the invention.

Furthermore, in the claims the word "comprising" does not exclude other elements or steps, and the indefinite article "a" or "an" does not exclude a plurality. A single unit may fulfill the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

The patent or application file contains at least one drawing executed in color. Copies of this patent or patent application publication with color drawing(s) will be provided by the Office upon request and payment of the necessary fee.

The present invention is also illustrated in some aspects by the following figures.

FIG. 1: Example of three color, 10×, image of the PBMC monolayer from a 384 well plate, split into three channels.

Figure 2:
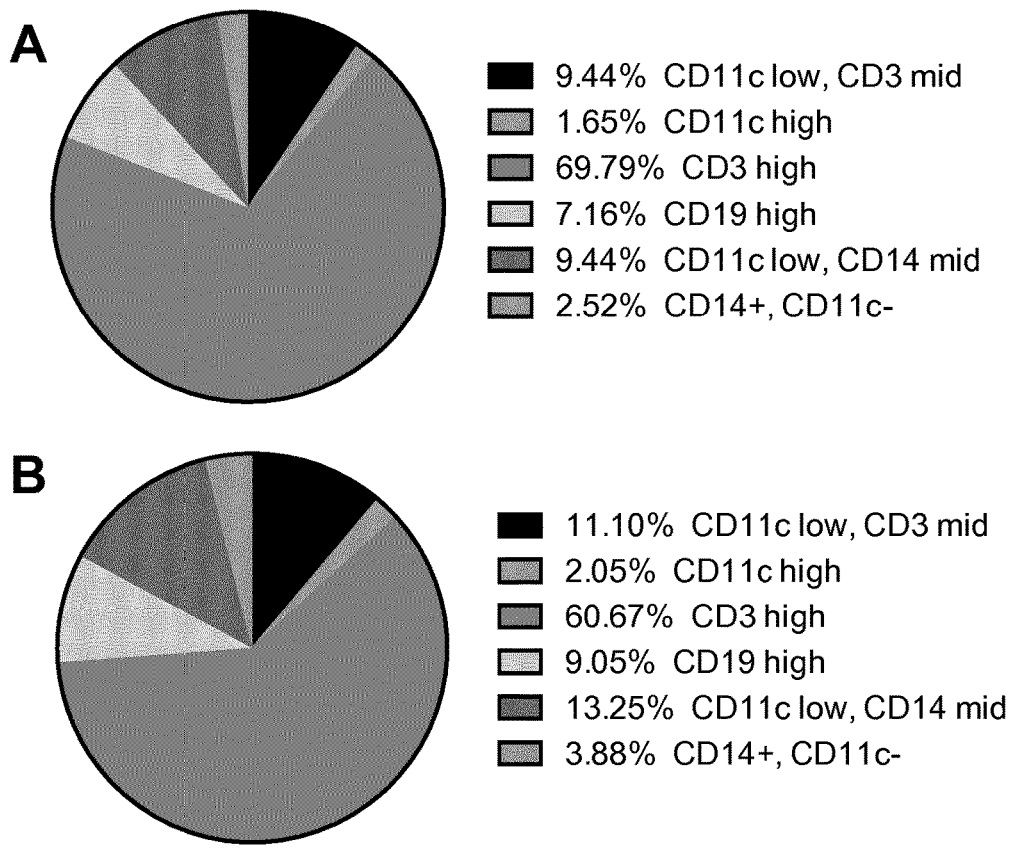

FIG. 2: Population tracking of PBMCs from a donor as analyzed by (A) flow cytometry, or (B) image cytometry.

Figure 3:
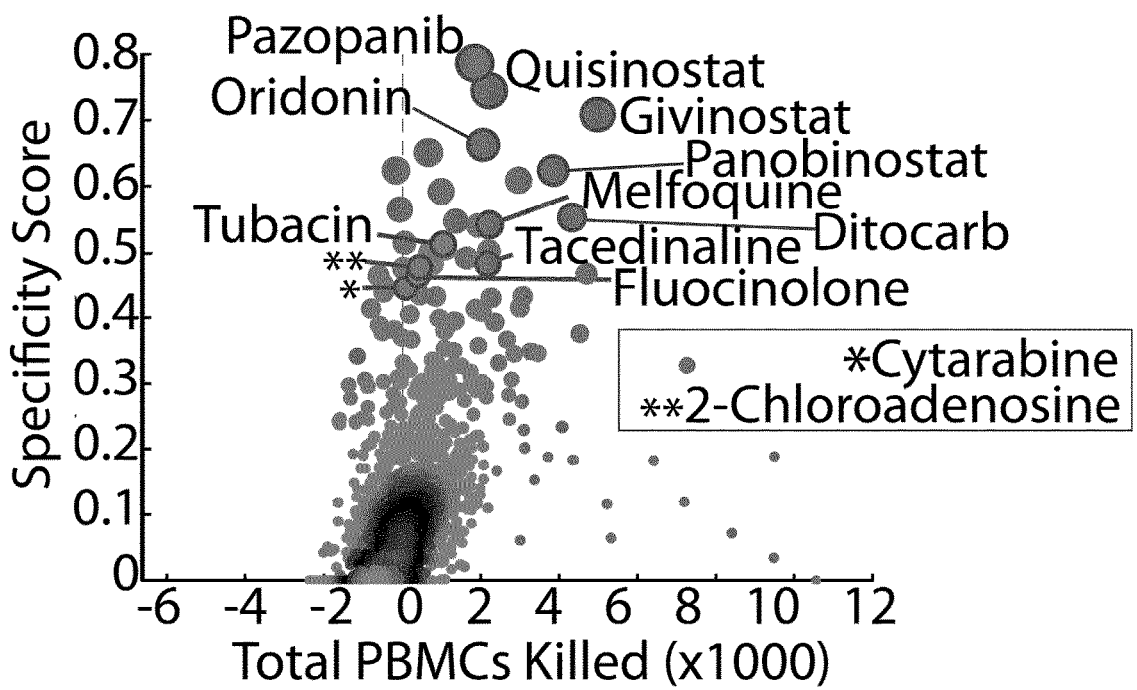

FIG. 3: Results of large-scale viability screen in PBMCs; compounds sorted on cell number reduced and "specificity score." Compounds highlighted are key anti-cancer candidate treatments.

Figure 4:
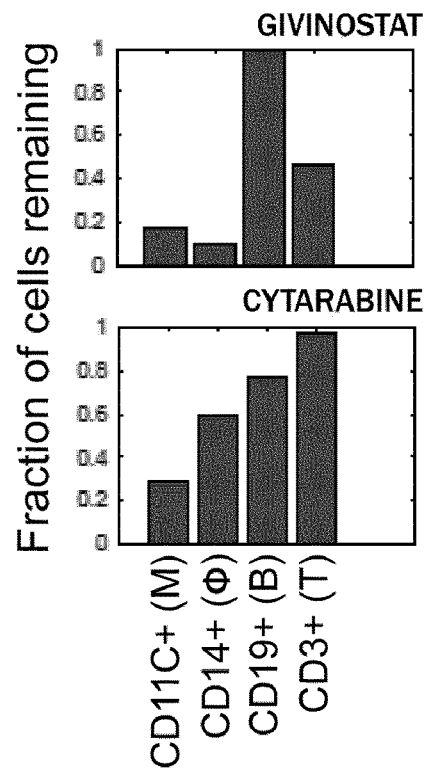

FIG. 4: Bar graphs showing drug-induced cell-population specific cytotoxicity of two different anti-cancer drugs FIG. 5: Heat map of top-hit HDACi and their population specificity.

Figure 6:
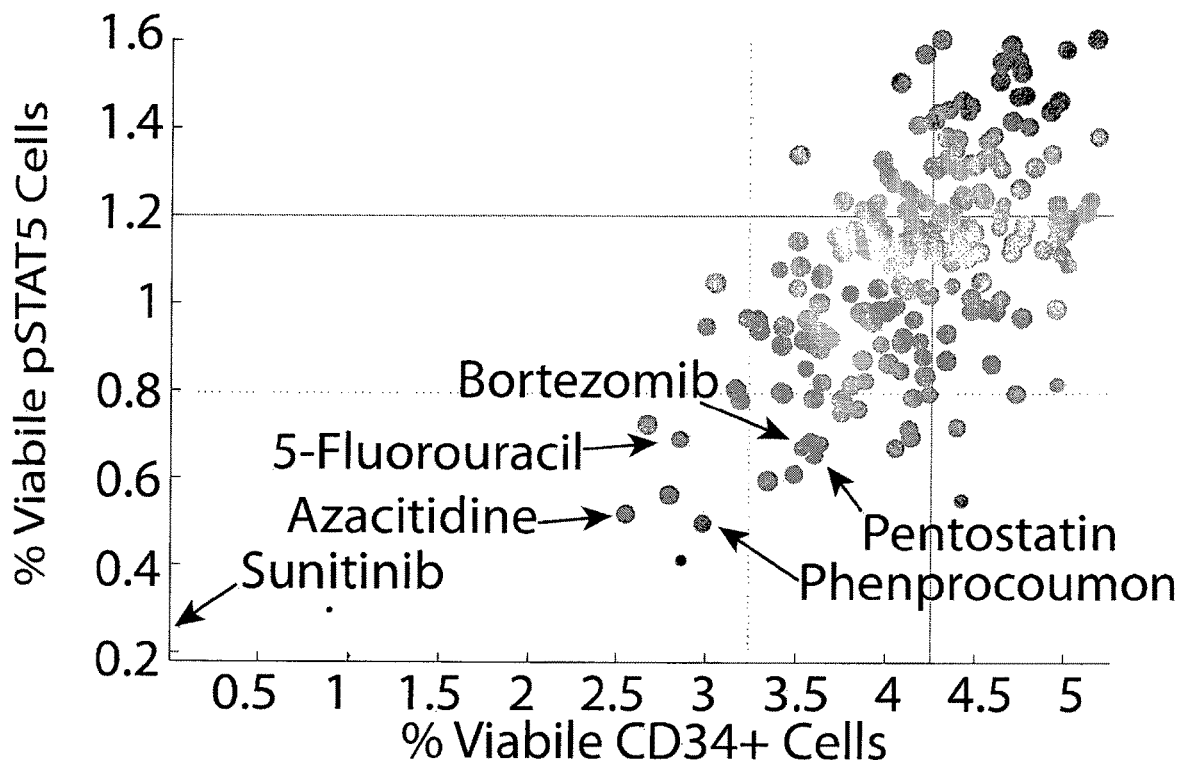

FIG. 6: Results of large-scale personalized chemotherapy screen in PBMCs from a patient suffering from a myeloproliferative disorder. Compounds plotted against percentage viable positive cells expressing two MPN specific biomarkers. Compounds highlighted are key anti-cancer treatments.

Figure 7:
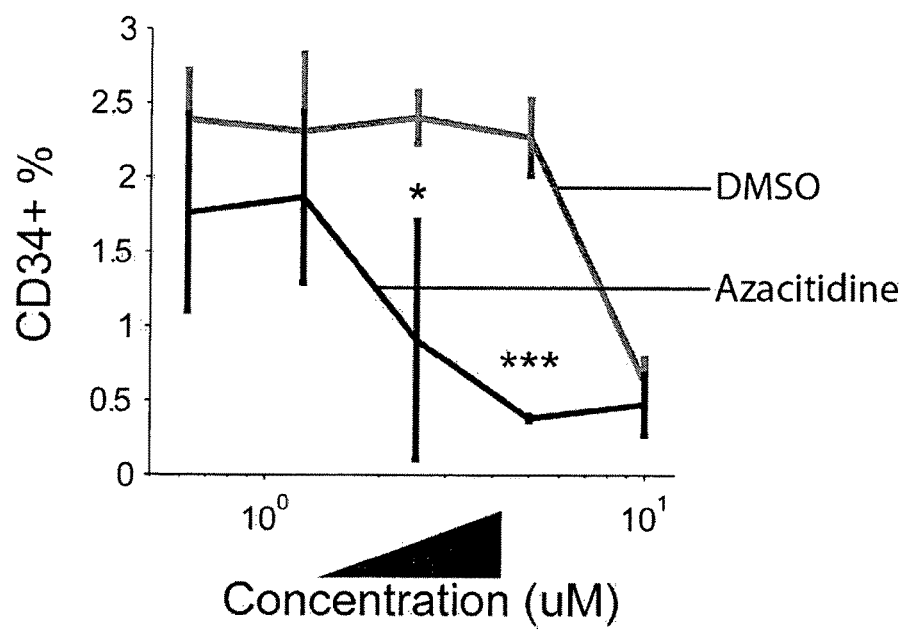
Figure 8A:
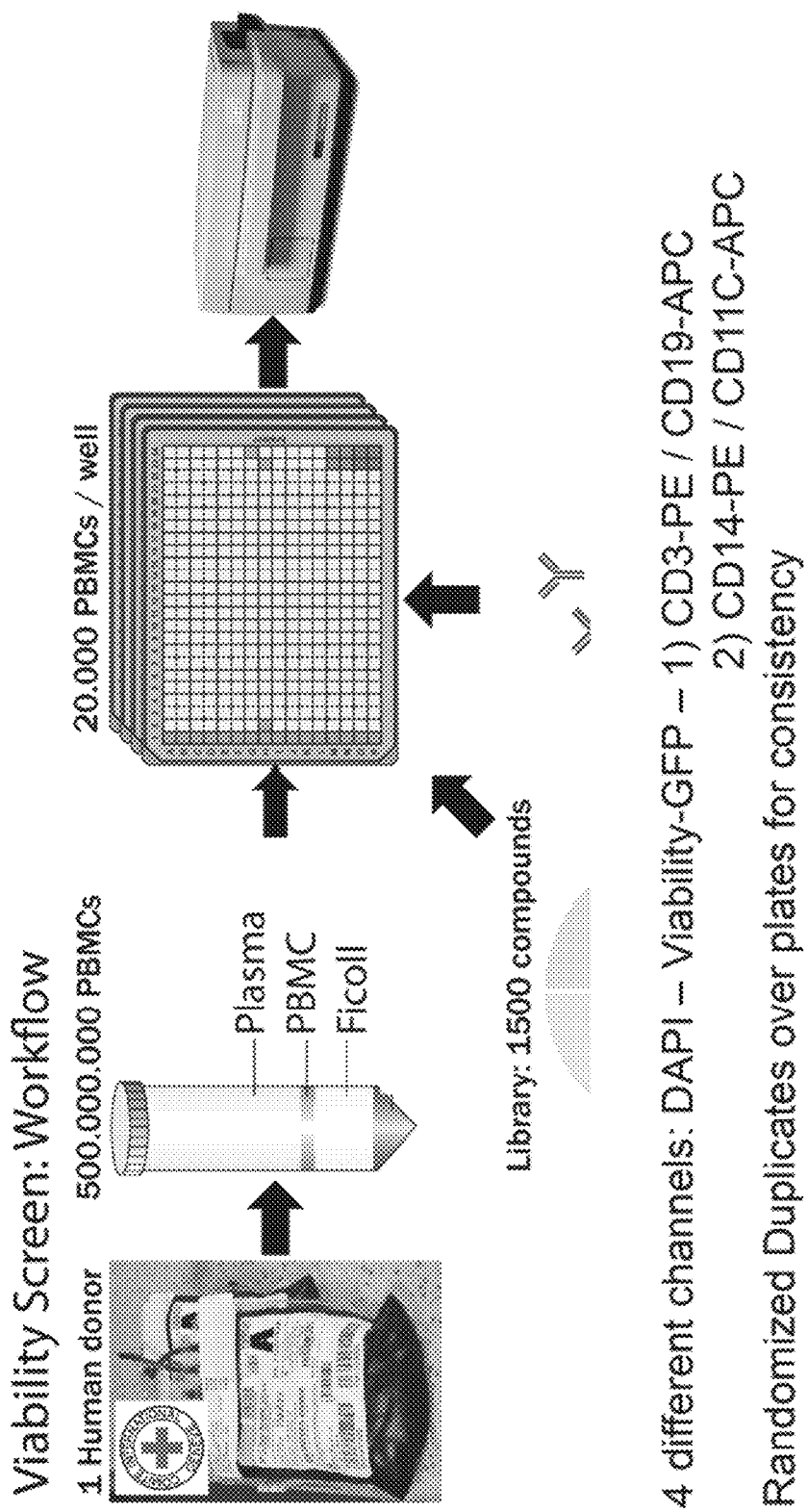
Figure 8B:
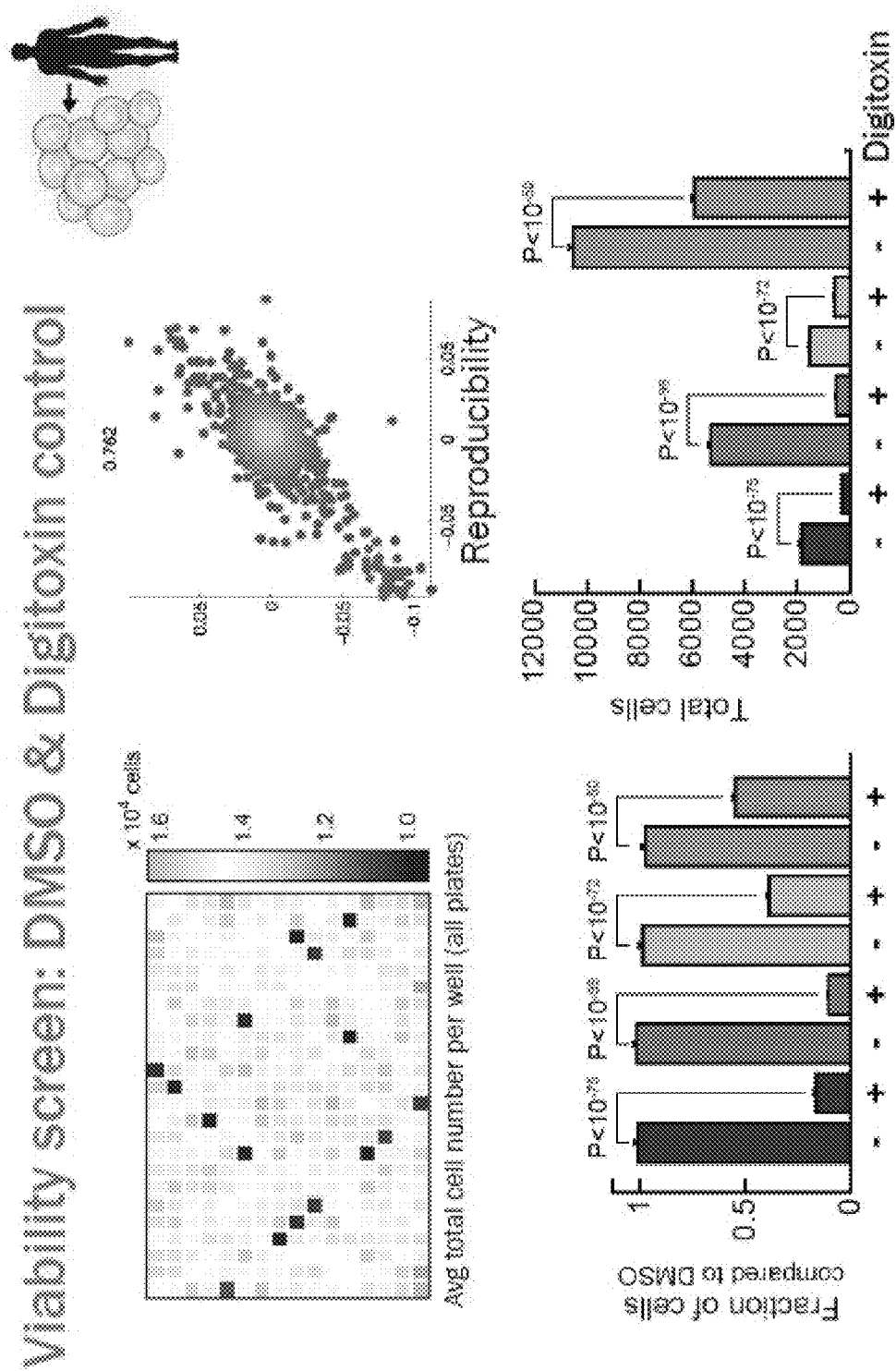
Figure 8E:
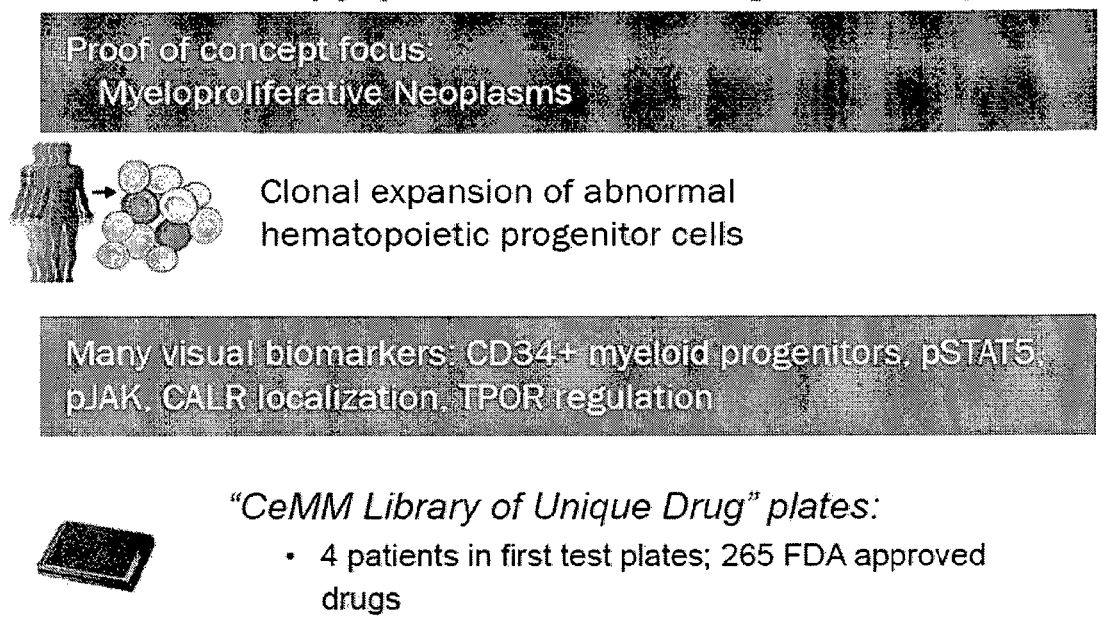
Figure 8F:
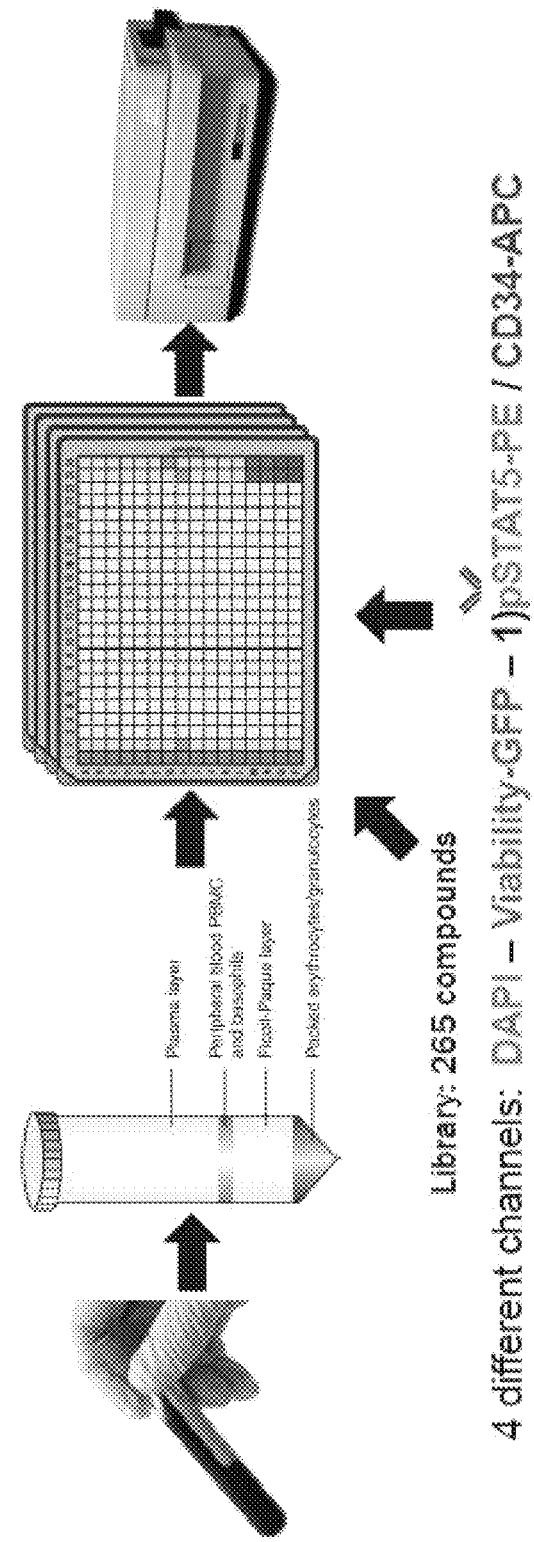

FIG. 7: Titration curve of top-hit novel anti-MPN drug in clinical trial now for combination therapy with a JAK inhibitor, which this patient is currently on. Titration curve of drug, lower, is compared directly to that of DMSO on a single cell level controlled with healthy cells that do not express CD34.

FIG. 8: Illustration and flow-charts of embodiments and specific embodiments like exemplified staining (anti CD3/CD19; CD14/CD11; pSTAT5/CD34) and corresponding results for exemplified personalized drug discovery in schematic fashion.

Figure 9:
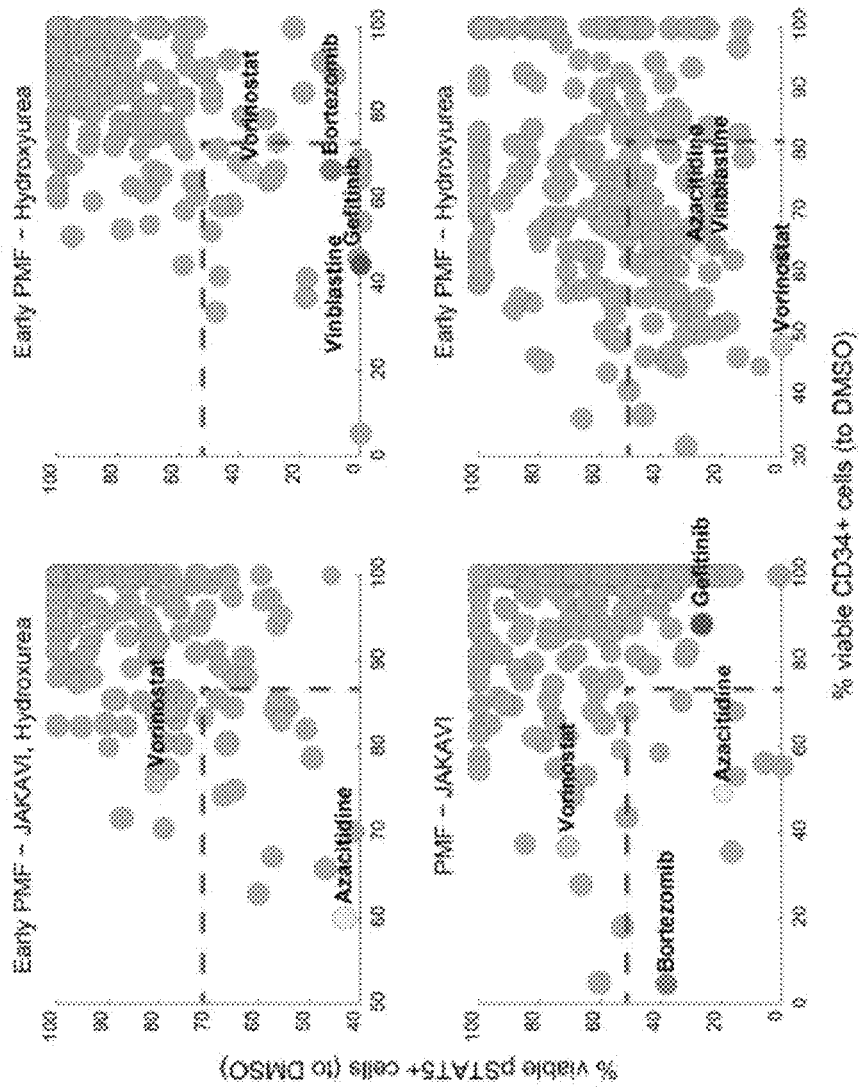

FIG. 9: Pharmacoscopy results of four patients. These four patients suffer from early primary myelofibrosis (PMF) or primary myelofibrosis that have been screened through 265 unique FDA approved compounds. Highlighted compounds for each patient reduce the percentage of viable cells expressing trackable biomarkers (either CD34 or pSTAT5, indicative of PMF) relative to DMSO control compounds. Highlighted are known anti-cancer drugs, known in the art as suitably for the treatment of blood cancer.

Figure 10:
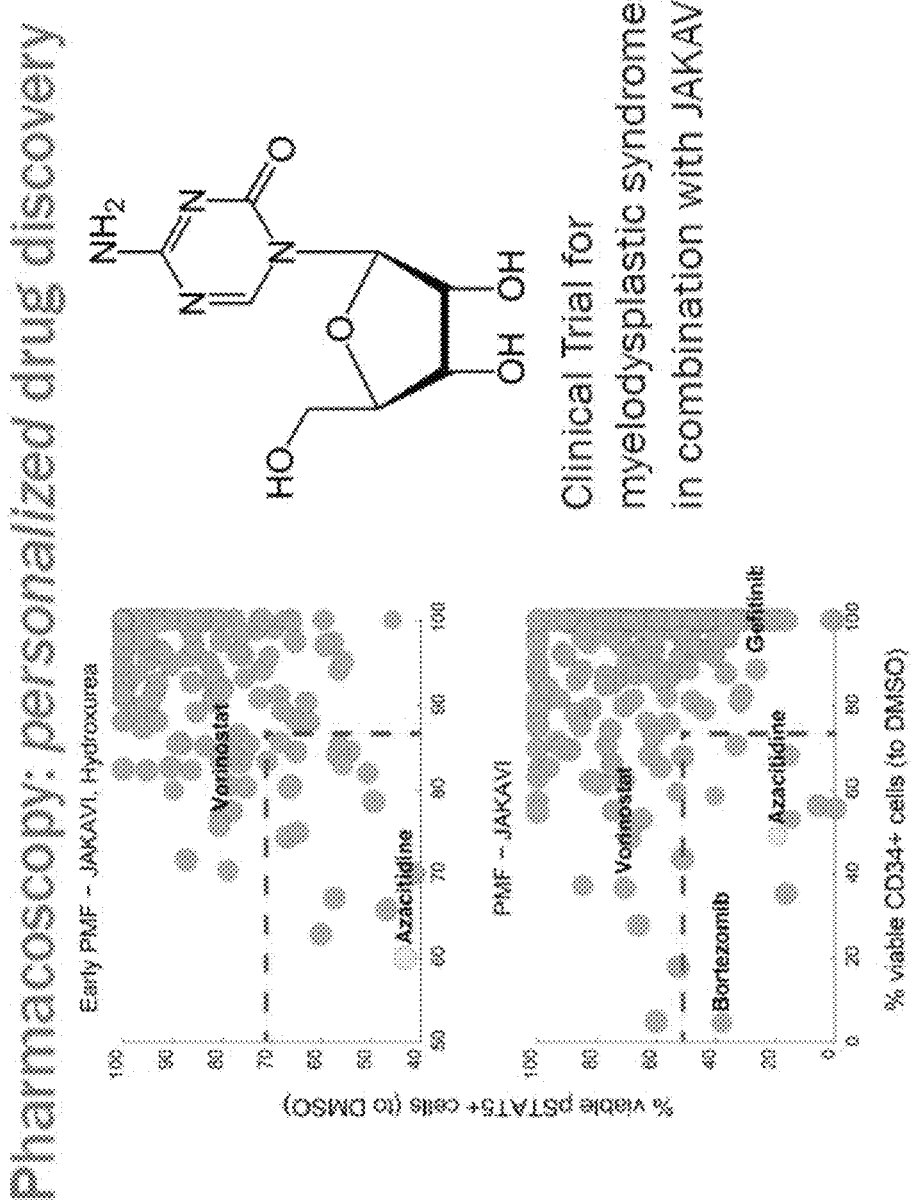

FIG. 10: Results for two patients with early PMF or PMF, both treated with the JAK inhibitor Ruxolitinib at the time of Pharmacoscopy. Top drug or highly enriched drug is Azacitidine, which is in clinical trials for the treatment of myloproliferative diseases in combination with Ruxolitinib. Furthermore, the Pharmacoscopy overseeing physician has used Azacitidine to treat two primary myelofibrosis (PMF)-patients, already on Ruxolitinib (tradename: Jakavi), who are responding well. In conclusion, these data as presented in FIG. 10, confirm the successful use of aspects of methods of the present invention based on PBMC monoloyer technology/Pharmacoscopy. Valuable data and information can be generated and technical as well as medical advantages can be obtained and provided. In particular, these data confirm results as obtained in parallel in laborious clinical trials and as obtained from existing patient response (control) data. Optical/Imageable/stainable PBMC monolayer technology as provided herein confirms the successful use of a predicted combinatorial treatment as currently used in clinical trials. Accordingly, in some embodiments, optical/imageable/stainable PBMC monolayer technology of the present invention can be highly predictive in drug screenings and/or personalized treatment protocol methods, as exemplified herein for PMF treatment with Azacitidine and Ruxolitinib.

Figure 11:
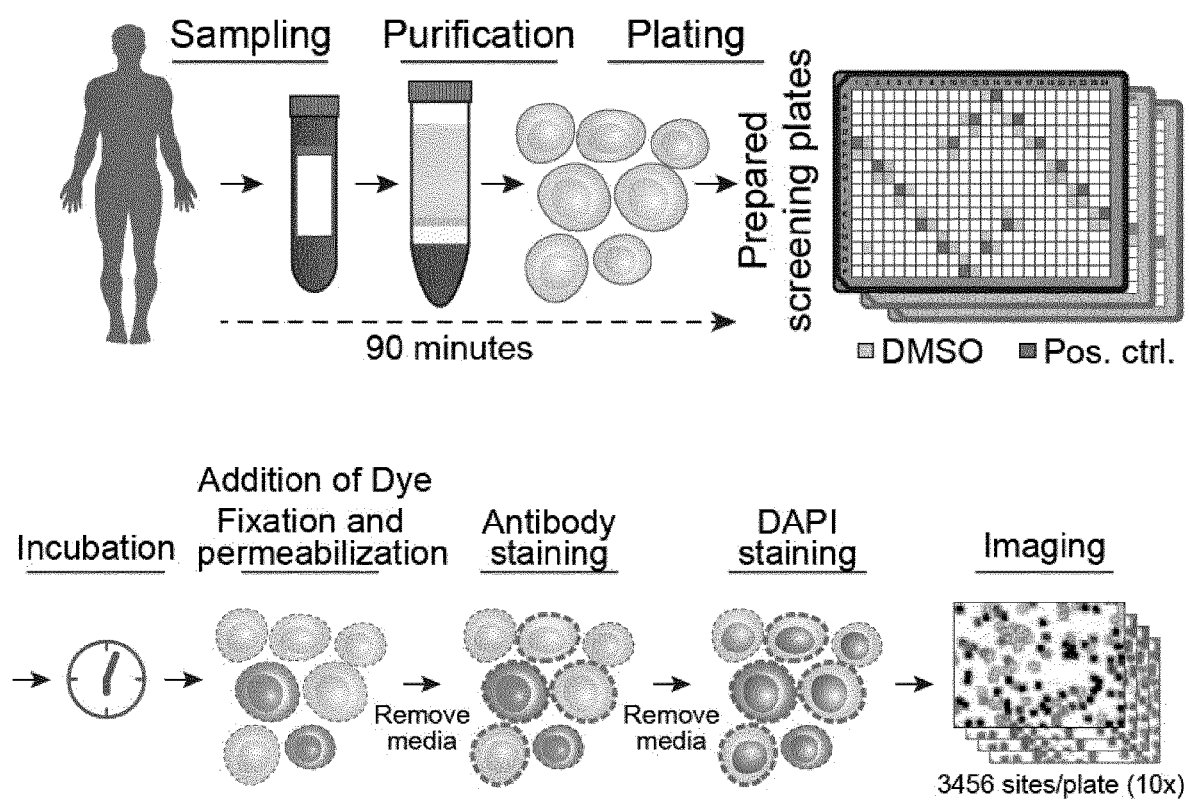

FIG. 11: General workflow for methods provided herein ("pharmacoscopy"). The herein provided method is such that fresh blood or bone marrow is taken from an individual and the mononuclear cells from the sample purified over a gradient, or, frozen samples are collected from previous purification. The cells are diluted to the proper density in cell culture medium and plated in 384-well plates containing drugs. The cells are incubated at 37° C. with 5% CO2 for an indicated amount of time. Viability dye is then added, if needed, and the cells are then fixed and permeabilized. Antibodies conjugated to fluorescent markers are then added, along with DAPI for nuclear detection. The plates are imaged on an automated microscope.

FIG. 12: Patient data. (A) Viability of $CD34^+$ or $pSTAT5^+$ cells from a patient with primary myelofibrosis after incubation with 265 FDA-approved diverse compounds. Gray dashed lines represent population averages; highlighted compounds have known anti-cancer properties. (B) Viability of all CD34+ cells after treatment with (C) Azacitidine or (D) DMSO; bottom right hand corner of plots are viable hematopoietic progenitor cells remaining after treatment. (C) Total viable PBMCs only after treatment with each drug screened for in (B), showing that, without the use of pharmacoscopy, the top hit is not the same. independent of single-cell analysis. (D) the patient from (A) on combination treatment identified by pharmacoscopy (left) or initial standard treatment (right).

Figure 13:
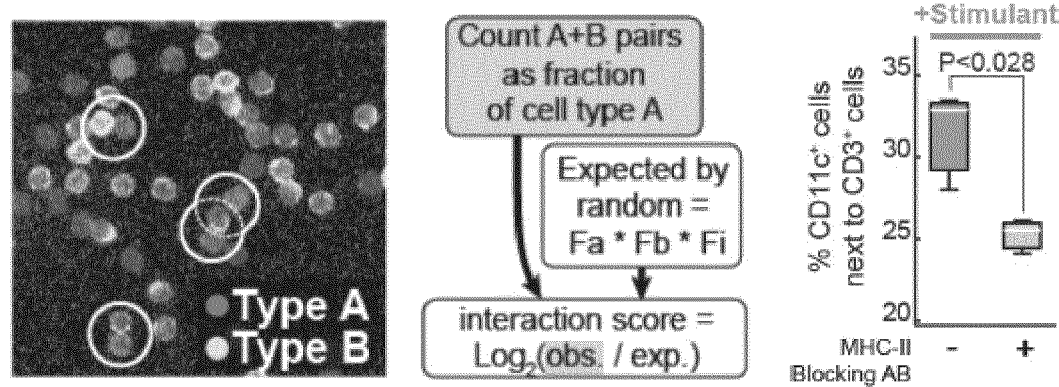
Figure 14A:
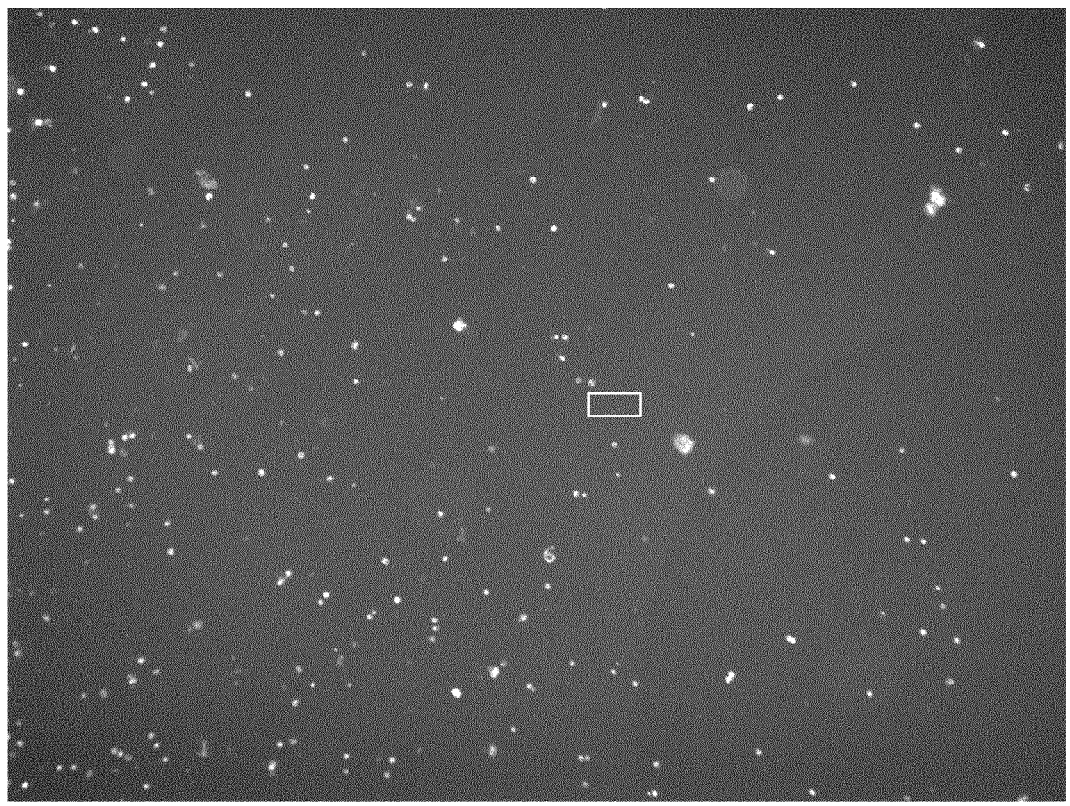
Figure 14A:
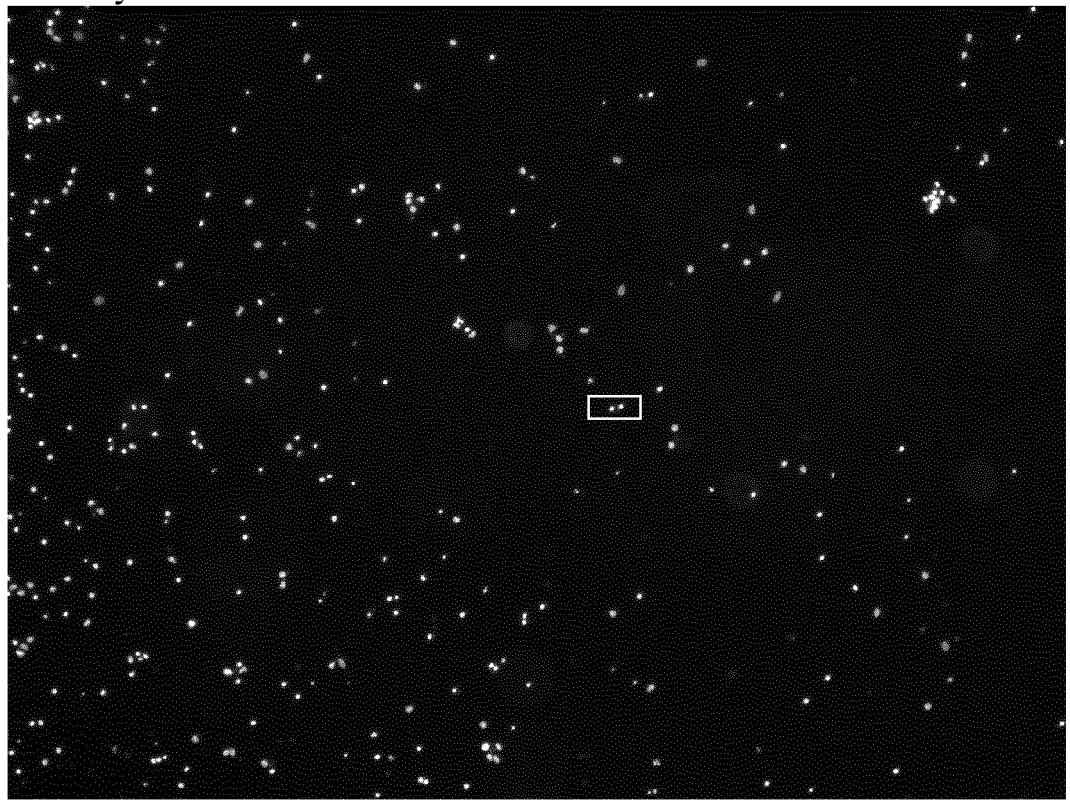
Figure 14B:
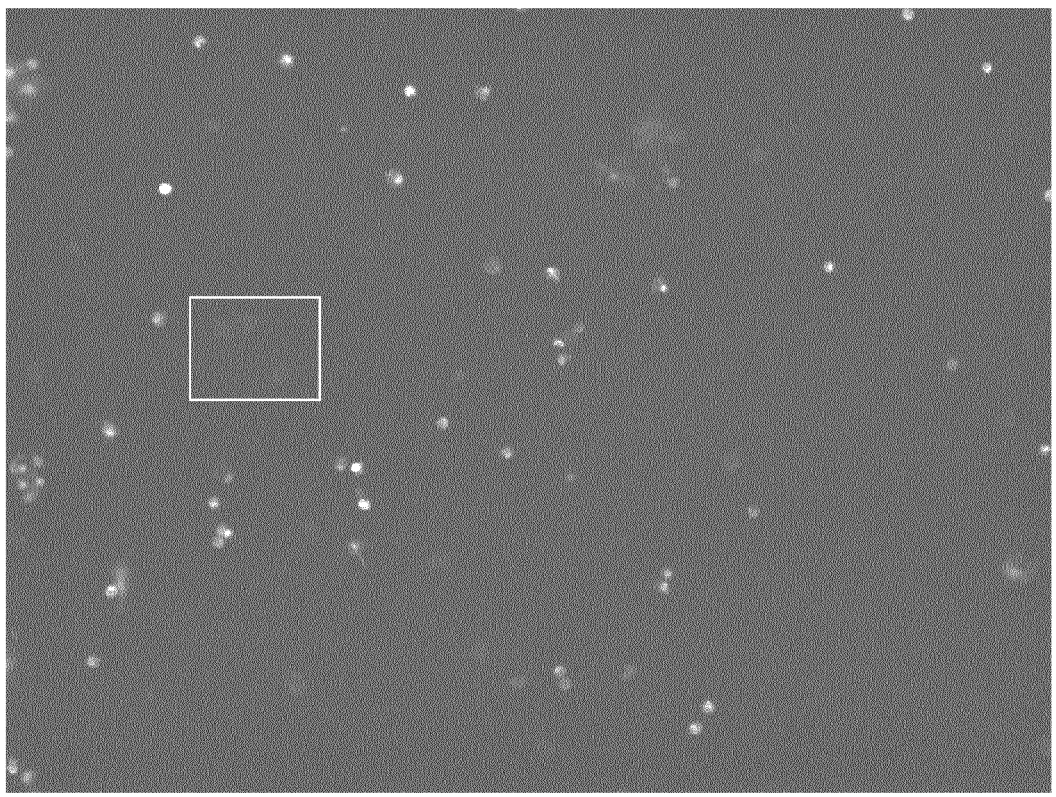
Figure 14B:
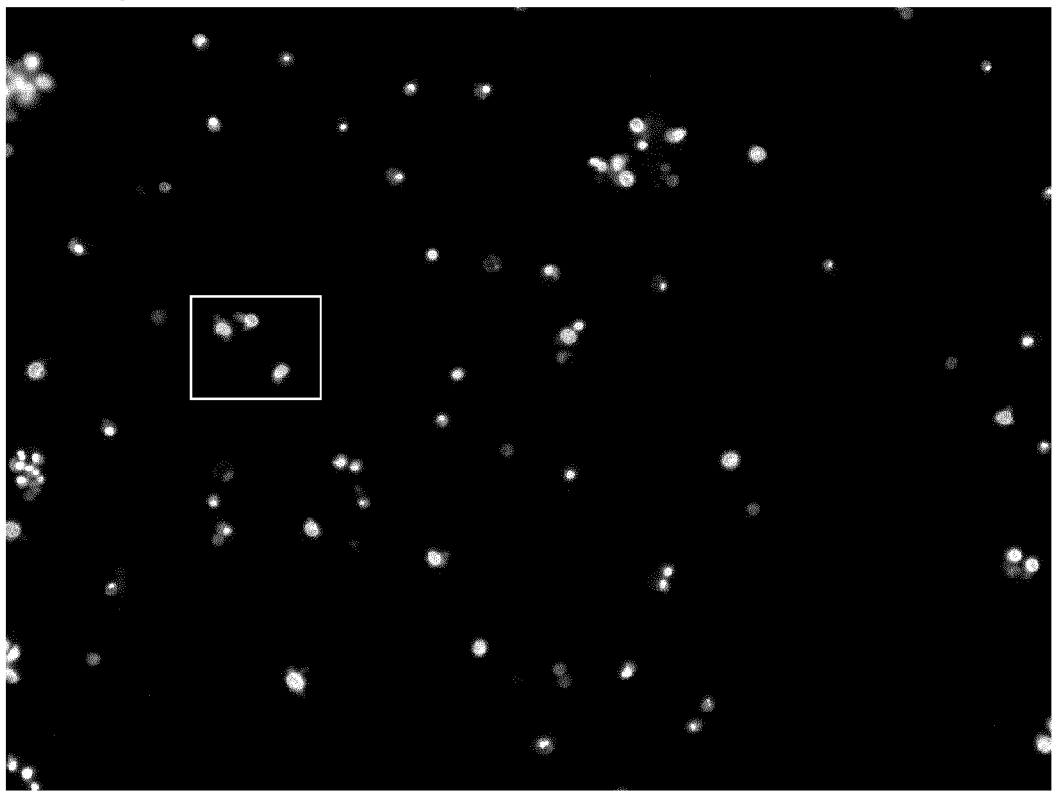

FIG. 13: Computational method. (Left) example image with types of neighboring cells in circles. (middle) creation of an interaction score to judge cell-cell contacts and cell neighbors. (right) example of interaction score usage after PBMC activation with VSV either alone or with a blocking antibody against MHC-II. MHC-II blocks the relationship between CD11C and CD3 positive cells.

FIG. 14: Images of bone-marrow cell monolayers. Human bone marrow nuclear staining and viability status staining at 10 (FIG. 14A) and 20× magnification (FIG. 14B). The box in the images denotes examples of live cells within the monolayer as produced by this method.

FIG. 15: Images of cell samples prepared using methods of the prior art. Figure A resents (left) the monolayer when additional centrifugational forces are added to the monolayer: the loss of natural occurring cell-cell interactions as the adhesion and relationship to other cells are forced. On the right is the method presented here in which the cells are only under the natural force of gravity as distributed by the meniscus. B represents the method here (SLP) versus the method in Douglas et al. where 1e6 cells are added to each well, this is 50× higher then what is recommended by the protocol presented herein. The arrows point to clumping in the over packed well which are non-existent in the SLP as they are not over packed, and the arrow heads point to morphological characteristics displayed by the cells which are not present in the overacted well and thus cannot be tracked using any method but the one presented here. (C) Represents the protocol in Katrien Princen et al. as compared with the method of the invention where a low-spin is applied to the plate and 5e5 cell/well are used. The spinning, even at a lower cell density, creates clumping within the well that does not occur in our method, further, cell-cell relationships cannot be measured due to the additional external force.

Figure 16:
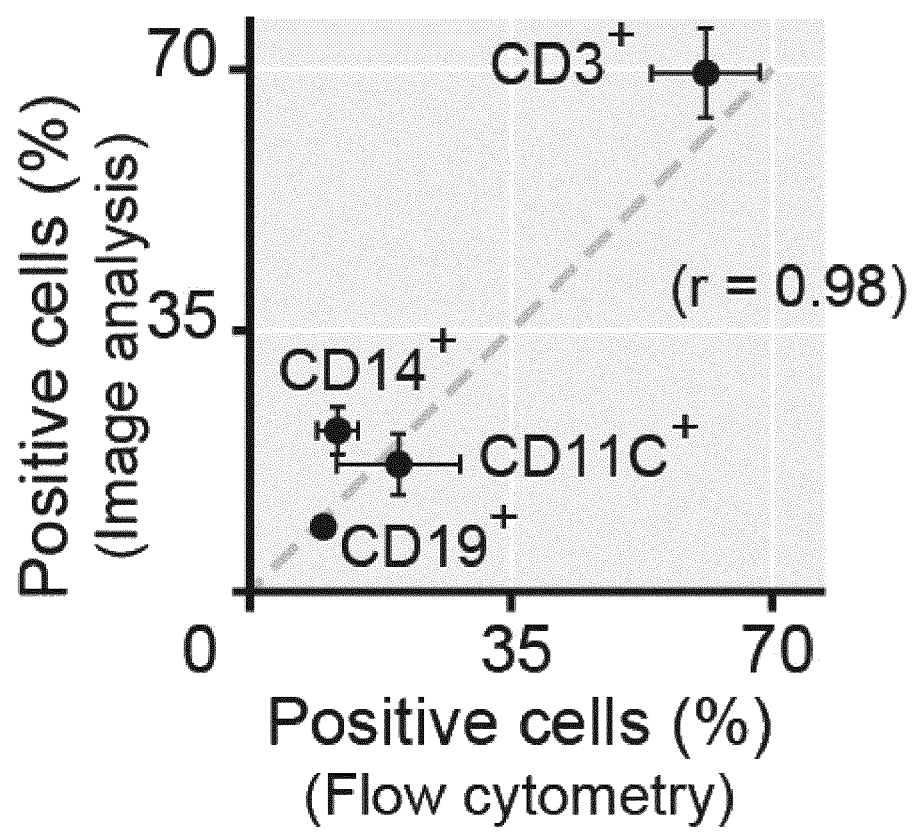

FIG. 16: Comparison of populations using previous method (flow cytometry) and the method provided herein in each well. Cells within the monolayer follow the same physiologically relevant pattern as measured by flow cytometry and image analysis of the monolayer. These numbers are standard for adult humans and are commonly used for diagnostic purposes.

Figure 17:
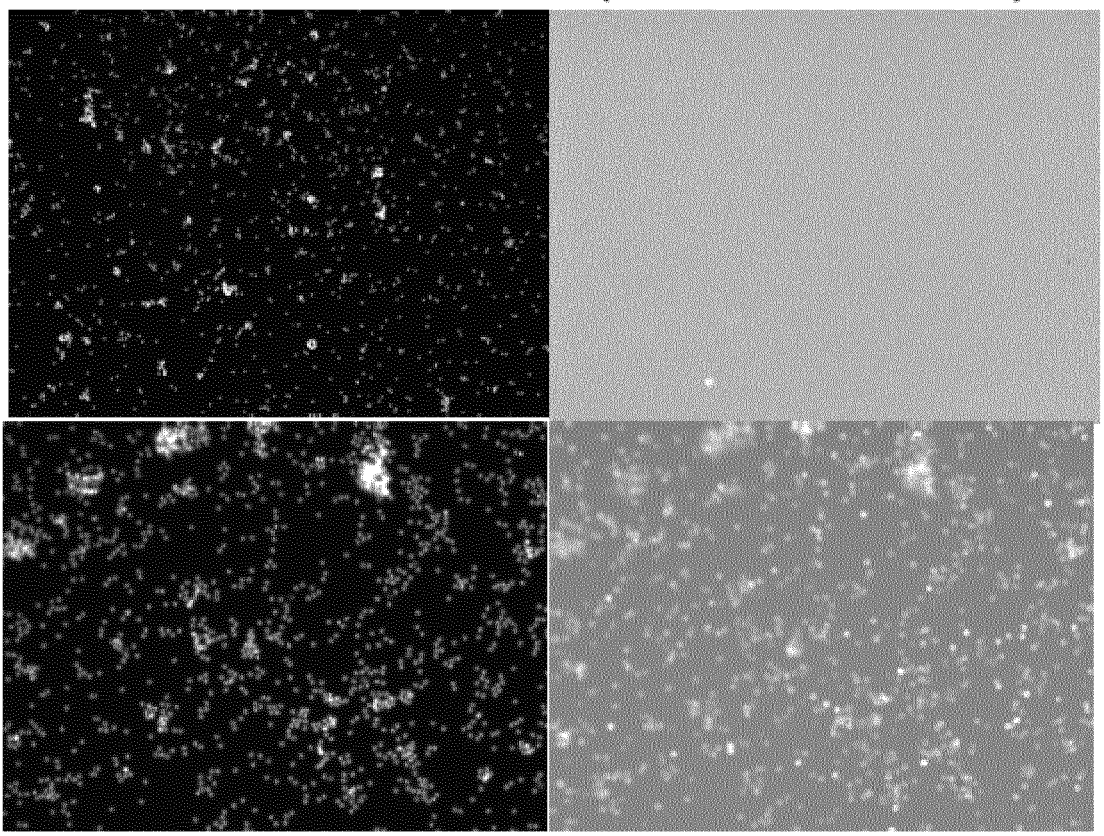

FIG. 17: Overpacking well creates a non-physiolgically relevant monolayer. Cells plated as described in Douglas et al. (2e6/well) increases the number of adherent cells, thus blocking the placement of non-adherent cell (here: t-cells). Upon removal of the media, non-adherent cells are removed from the well and have not sit, thus leaving the well with a disproportional number of cells (top row, no present T-cells where usually T-cells make up >75% of the monolayer and also are present as 75% of the PBMC population within healthy adult peripheral blood.) On the bottom, the SLP method is used which retains proportional T-cell numbers.

Aspects of the present invention are additionally described by way of the following illustrative non-limiting examples that provide a better understanding of embodiments of the present invention and of its many advantages. The following examples are included to demonstrate preferred embodiments of the invention. It should be appreciated by those of skill in the art that the techniques disclosed in the examples which follow represent techniques used in the present invention to function well in the practice of the invention, and thus can be considered to constitute preferred modes for its practice. However, those of skill in the art should appreciate, in light of the present disclosure, that many changes can be made in the specific embodiments which are disclosed and still obtain a like or similar result without departing from the spirit and scope of the invention.

Unless otherwise indicated, established methods of recombinant gene technology were used as described, for example, in Sambrook, Russell "Molecular Cloning, A Laboratory Manual", Cold Spring Harbor Laboratory, N.Y. (2001) which is incorporated herein by reference in its entirety.

A number of documents including patent applications, manufacturer's manuals and scientific publications are cited herein. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

EXAMPLE 1

Experiment:

To establish a culture protocol of PBMCs from healthy donors or patients which results in a stainable monolayer (single imageable field/imaging plane) for imaging in 384 well plates.

Method:

PBMCs were cultured as per protocol invented for pharmacoscopy. In a first step, blood is collected from (a) healthy proband(s) or patient(s). Typically, the volume is between 9 to 500 ml and the blood is stored in an appropriate container containing EDTA or heparin. The blood sample is then mixed at a 1:1 ration with PBS buffer. 30 ml of the blood/PBS mixture are layered over a 15 ml lymphoprep density gradient in 50 ml tubes for purification. The tubes are spun at 2000 rpm for 30 min at room temperature without break (no breaking of the centrifuge). The buffy coat above the density gradient and below the plasma is removed and placed into another 50 ml tube. Usually, the removed volume varies between 10 to 15 ml. The tube is then filled with PBS to 50 ml final volume and again spun at 2000 rpm for 5 min with centrifuge break. The supernatant is removed and the pellet suspended in RPMI with 20 ml 10% FCS and appropriate antibiotics. The pellet should have no more than a 5 mm thick band of RBCs. The cells are then counted to $4 \times 10^5$/ml and 50 µl are plated at a density of 20000 cells/well in corning 384-well imaging plates with black walls. The cells are left at room temperature for 10 to 15 min to settle and are then placed in a 37° C.+5% $CO_2$ incubator. The plates are then incubated for given time, ideally not more than overnight. If a viability dye is added, 30 µl of the supernatant are removed carefully by hand or with robotics and 30 µl of a 1:1000 mix in PBS of Invitrogen live/dead fixable 488 dye is added for 30 min at room temperature. Viability dye is removed as initial supernatant with automated pipet or robot. Disturbance of the monolayer should be avoided at this step. If no viability dye is added or immediately after it has been added, 30 µl of 2% formaldehyde with 0.1% triton x-114 is added and the plates are incubated at room temperature for 15 min. The supernatant is removed (all of it) by flicking. Because the monolayer is already fixed at this stage, this will not disrupt the monolayer. For staining, 30 µl of antibody staining are added. Tested cocktails are a dilution of 1:300 of GFP, PE or APC labeled antibodies used for flow cytometry. The dilution allows avoidance of washing steps. The plates are incubated for 1 hour at room temperature. The antibody is removed by flicking as above and a 1:100 dilution of DAPI in PBS in 50 µl is added. The plates are stored at 4° C. until imaging. Imaging is done at room temperature using an automated confocal microscope (PerkenElmer Operetta) with 4 non-overlapping channels and the data is exported for analysis.

Results:

After culturing PBMCs utilizing our novel protocol, adherent and non-adherent PBMCs formed a monolayer that could be imaged in a single plane of view, utilizing an automated confocal microscope, allowing for automated drug screening minimized into 384-well plates. Microscopy confirmed that 20.000 cells (±5%) could be imaged using the newly developed method, termed Pharmacoscopy.

EXAMPLE 2

Experiment:

Using the protocol developed in experiment 1, major antigens present on large populations of PBMCs were stained using fluorochrome-labeled antibodies (CD11C-APC, CD14-PE, CD19-APC, and CD3-PE), viability dye to determine membrane stability, and DNA binding dye to counter stain the nucleus (DAPI.) This experiment determined if important major populations of PBMC; many of which are non-adherent under normal culture conditions, could be imaged with this method.

Method:

PBMCs were cultured, fixed and stained as to the protocol outlined. 384-well plates were imaged using automated confocal microscope imaging in 4-separate channels. Staining combinations were: CD11C/CD14, CD3/CD19, CD11C/CD3, CD14/CD19—all with viability markers and nuclear staining.

Results:

Major populations of cells, including non-adherent cells (CD19+ B-cells and CD3+ T-cells), along with the viability marker and nuclear staining was imaged using automated confocal microscope. The specific visualization of the non-adherent populations was important to determine if this method could track populations that normally do not form single imageable monolayers, which were not, to the knowledge of the inventors, imageable prior to the development of the present invention. Images of CD19+ and CD3+ stained cells are shown FIG. 1.

EXAMPLE 3

Experiment:
Flow cytometry is a lower-throughput, widely used, method of determining PBMC populations. To resolve if the populations visualized and calculated by pharmacoscopy were equal to that of flow cytometry, we compared the two technologies.

Methods:
PBMCs were cultured, fixed and stained with the pharmacoscopy protocol described in Example 1. 384-well plates were imaged using automated confocal microscope imaging in 4-separate channels. Staining combinations were: CD11C/CD14, CD3/CD19, CD11C/CD3, CD14/CD19, and all single stains (CD11C, CD14, CD3, CD19.) The same donor cells were also stained for flow cytometry using standard techniques. Flow cytometry allows for quantification of populations, and is the current standard technology for analysis of non-adherent cells.

Results:
As shown in FIG. 2, the populations percentages of all stains were comparable whether analyzed by flow cytometry (top) or by pharmacoscopy (bottom.)

EXAMPLE 4

Experiment:
It was next established that the means and methods provided herein, also named "Pharmacoscopy", could detect spatial relationships of cells, could detect the activation states of each population by staining for pro-inflammatory pathway activation with intracellular resolution, and could detect modifications in cell and nuclear size/shape/texture, over a large selection of anti-inflammatory drugs (100) at various time points. We stimulated healthy donor cells with a GFP expressing virus and tracked NF-kB activation with an antibody specific to phospho-p65 and tracked both cell type, viability, and the staining and subcellular localization of phospho-p65 (which, upon phosphorylation, is activated and translocated to the nucleus, resulting in a strong inflammatory response.)

Method:
PBMCs were cultured, fixed and stained with the pharmacoscopy protocol. 384-well plates were imaged using automated confocal microscope imaging in 4-separate channels. Staining combinations were: CD11C/phospho-p65, CD14/phospho-p65, CD3/phospho-p65, CD19/phospho-p65, a virus expression GFP, and nuclear markers. The cells were left naive or stimulated with VSV at a multiplicity of infection of 10 for 30 minutes, 1 hour, 6 hours, and 12 hours.

Results:
Cells treated with virus had significantly more "clumping" then cultures not treated signifying 1) a higher activation state, and 2) that pharmacoscopy analysis can determine special interactions over cultures (measuring the distance between cells and cell types depending on stimuli.) Moreover, this also strongly indicates the cultures are able to migrate on the monolayer before fixation, and that the fixation step of Pharmacoscopy is the final moment of movement. Furthermore, pharmacoscopy can track changes in a specific population; changes such as cell size, nuclear morphology and texture over a time course with stimulation or drug treatment allowing for yet another parallel source of information to be confirmed through the images of the novel monolayer of PBMCs.

Conclusion of Experiments 1-4:
The creation of a protocol for the culturing, fixation, staining and imaging of mainly non-adherent PBMCs into an imageable monolayer represents a fundamental breakthrough of our ability to perform high-throughput and high-content drug screening directly in a physiologically relevant system. Pharmacoscopy allows for the systematic deciphering of numerous parallel lines of previously unreachable data. Data lines such as 1) detecting multiple populations of non-adherent and adherent cells in the same culture without the need for spinning, enzyme digestion chelation, or cell scraping, 2) nuclear morphology, 3) cell-cell relationships in high-throughput images, 4) recapitulation and visualization of pathway activation over relevant cell types, 5) subcellular protein localization and/or protein/protein co-localization and more. Furthermore, pharmacoscopy uses standard automation systems and needs only limited donor material (nearly $1/10^{th}$ less than competing methods).

Using the means and methods provided herein, automated screening for pharmaceuticals, like anti-cancer compounds, is possible. In addition, the means and methods provided herein can be used in diagnosis, like in the assessment of treatment options and the like or predictive chemotherapy, and/or in the tracking of various biomarkers. The means and methods provided herein also allow the high-throughput analysis of hundreds of compounds simultaneously. Furthermore, the means and methods provided herein allow diagnosing a disease or predisposition to a disease in a PBMC donor/bone-marrow cell donor comprising the monolayer of the invention or PBMCs/bone-marrow cells cultured according to the methods of the invention. In addition, the means and methods provided herein can be used to determine whether a subject suffering from or predisposed to a disease will respond or is responsive to treatment with a therapeutic agent.

EXAMPLE 5

Experiment:
The herein provided means and methods, in particular the monolayer of the invention and/or a monolayer formed by the methods of the invention was used to discover anti-cancer drugs, specifically targeting hematopoietic diseases, in physiologically-relevant system. Prior art cell lines are far from relevant as interactions of various cell types which are present in vivo are not accounted for. PBMC screening, using the means and methods provided herein, in particular using high-content analysis using the means and methods provided herein, allows for a much more detailed description of events. Furthermore, many chemotherapy options are cytotoxic to the point of leaving a patient with no functioning immune system; our screening method would determine population specific effects of drugs.

A selection of 1500 small compounds were spotted in duplicate over 384-well plates and combinations of PBMC subsets, as in experiment 2, were stained along with viability (membrane integrity) and nuclear stain (DAPI.) It was aimed at determining the global picture of PMBC viability changes. Therefore, it was focused on each individual population to decipher specific targeting. This screen was performed over 3000 wells on more than ten 384-well plates, automatically while determining adherent and non-adherent populations, at the single cell level.

Method:

PBMCs were cultured, fixed and stained using the methods of the present invention, in particular as described in the above Examples. 1500 compounds selected at random from our compound library were spotted in 5 nl in 384 well plates. Cells were incubated at 37 C with 5% CO2 for 36 hours. After 36 hours, the viability maker was added as the pharmacoscopy protocol. 384-well plates were imaged using automated confocal microscope imaging in 4-separate channels. Staining combinations were: CD11C/CD14 and CD3/CD19. Each staining combination was also stained with the viability marker and DAPI.

Results:

This screen yielded a major data set that was broken into three visualizations: 1) a measurement of global cell viability change, which was normalized to the ability of the drug to specifically target a single stained population (FIG. 3). FIG. 3 shows all 1500 compounds, each represented by a dot, comparing the total number of PBMCs killed to the "specificity" of the ability for the compound to target one or more specific cell type(s) present in the staining. The selected top hit compounds, outlined in black with names, represent a significant enrichment of drugs prescribed for hematological cancers. 2) From the determination of population specific cytotoxicity, possible drug repurposing can be and were determined (drugs that are given for one cancer but may be better suited to, or also used to target, other populations.) Two examples of drug repurposing or targeting is shown in FIG. 4. Whereas givinostat (FIG. 4, top) is in clinical trials for the treatment of relapsing leukemias and myelomas, based on the provided results, it may not be effective for B-cell derived cancers such as B-cell chronic lymphoblastic leukemia (B-CLL.) Furthermore, cytarabine (FIG. 4, bottom) an FDA approved drug, may work as a broad-spectrum anticancer, however, it could be more effective against myeloid derived, rather then lymphoid, cancers from its ability to better target macrophages and dendritic cells, and B-cells to a lesser extent.

Figure 5:
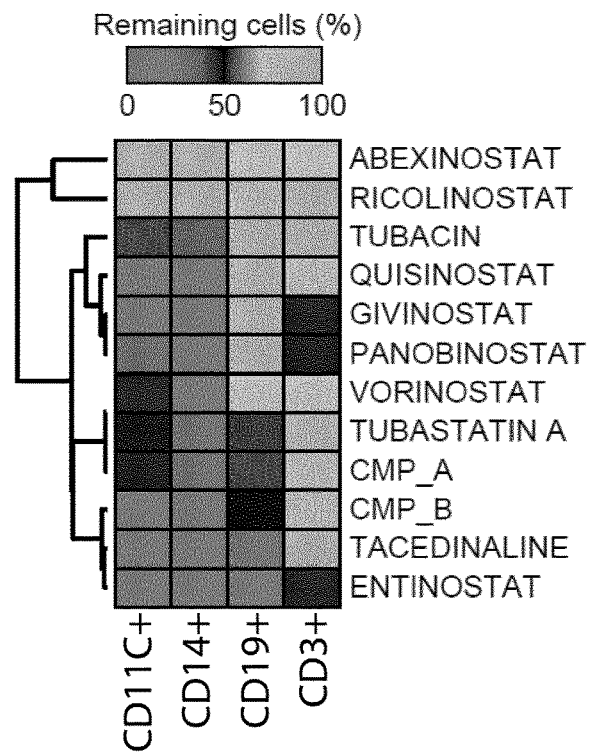

While this initial large-scale concept screen was performed on healthy donor blood, it can still elucidate both novel anticancer compounds, and also specify target cells. FIG. 5, for instance, outlines HDAC inhibitors that were recovered from the viability screen (i.e.: had high specificity scores) and the leukocyte sub-populations affected after 36 hours of incubation, Included in this list are also two recently synthesized HDAC inhibitors with unknown targets, labeled "CMP_A" and "CMP_B." Using their pattern of cell-specific killing in this particular screen, along with our in house chemo-proteomics, molecular targets and mechanisms for novel drugs such as these can be determined directly in the affected cell population.

Conclusion:

Studies which have laid the groundwork for population-characteristic analysis driven by sub-cellular and single-cell resolution have relied on genetically identical cell lines, which are not physiologically relevant to human health and disease. Moreover, the relevance of drug-discovery for human diseases in cell lines has recently been brought into question after inconsistencies in published work were identified (Haibe-Kains et al., 2013.) Here, we have described a system for the detection of selection of compounds that specifically targets various subpopulation of PBMCs even using a healthy donor, which opens the door to the ability to begin screening even more libraries for even more specific population-targeting drugs. Accordingly, the means and methods provided herein can be used in drug screenings and/or methods for determining whether a donor suffers from a disease and/or whether a donor will be/is responsive to treatment using compounds known in the art and/or compounds discovered using the methods of the present invention.

EXAMPLE 6

Experiment:

Based on the formation of the methodology as outlined in experiments 1-4, i.e. using the monolayers of the present invention, and also the results of our novel compound screen in experiment 5, predictive chemotherapy was implemented by tracking detailed biomarkers at the single-cell and global levels over 350 drugs using the means and methods of the present invention. Specifically, the best chemotherapy options in patients suffering from myeloproliferative neoplasms were tracked based on the viability of CD34+ myloid progenitor cells and cells containing the phosphorylation of STAT5; both of these stains are known as general biomarkers for multiple types of MPN including early primary myelofibrosis and polycythemia vera.

Method:

PBMCs were cultured, fixed and stained as to protocol outlined in the above examples. 384-well plates were imaged using automated confocal microscope in 4-separate channels. We stained CD34-APC, pSTAT5-PE, GFP viability maker, and a DNA binding nuclear stain. Patient material was cultured on drugs for 18 hours before the addition of the viability marker. These images contained both clonal blasts (almost all CD34+ cells that are present in the peripheral blood) activated cells (pSTAT5+ cells) as well as inherently healthy cells from the same donor. Uniquely, pharmacoscopy was able to, at a single-cell level, control for drug effects on patient cancer by allowing directly controlled comparisons with the healthy cell populations in the same images.

Results:

The viability of cells that were either specifically stained for CD34 or pSTAT5 was determined. Out of the approximately 350 compounds screened at random, the top hit compounds, which decreased the viability of cells expressing the biomarkers (FIG. 6, highlighted) are regularly given for cancer, and some specifically for MPN or other myelomas. One drug, specially, Azacitidine, is currently demonstrating success in clinical trial for the treatment of early PMF in combination with JAK inhibitors, with which this patient is already being treated. Furthermore, upon titration of Azacitidine in the same patient, while tracking the viability of CD34+ cells compared to healthy cells and compared to DMSO, concentration dependent effects were seen (FIG. 7). The results of this experiment are also illustrated in FIG. 12.

Conclusion:

The single cell analysis using the PBMC monolayer of the invention in patients suffering from blood cancers yielded strong top hit chemotherapy choices which leads to better and more targeted treatments. While sequencing and proteomics offer predictive personalized medicine, the means and methods provided herein offer directly measured phenotype tracking ex vivo, which has been demonstrated to relate directly to in vivo drug response.

EXAMPLE 7

Experiment:

PBMCs have been prepared using methods of the prior art and the method of the present invention. In particular, the method described by Douglas et al. (2001) Current Protocols in Immunology (published on May 1, 2001) and the method described by Katrien Princen et al. (2002) Cytometry Part A vol. 51A, no. 1, pp 35-45 have been followed. That is, PBMC monolayers were prepared by plating cells at the density noted in step 15 pg 12.9.8 of Douglas et al., which is outside the maximum range necessary for creation of the PBMC/bone marrow monolayer as claimed. A second layer was formed using the protocol described by Katrien Princen et al., wherein a step of "low speed" (i.e. 500 RPM) spin with low acceleration and no break is applied.

Results:

Prepared layers of PBMCs were analyzed by microscopy. Images of cell monolayers comparing the methods provided herein to methods in Douglas et al. and Katrien Pricen et al., respectively, are shown in FIG. 15.

Using a technique that applies more gravitational force, like centrifuge gravity, on the cells then is applied in the methods of the invention, e.g. as described in Example 1 (normal gravitational forces and meniscus forces, if any) disrupts the plating procedure and creates a monolayer that is built-up upon itself and not imageable fully—further, the act of centrifugation disrupts the cell-cell contacts that naturally form using the protocol outlined for Example 1. Once force is applied, or the cells are so dense that they cannot freely move around then the relationship of cells to each other cannot be measured, or their measurement has no consequence on the relevance in a person. As comparison, PBMC monolayers were prepared as described in Example 1. In the methods of the invention, the cells sit with no additional forces then what are present in the well, such that all the cell-cell interactions, placements, and neighborhoods are physiologically relevant (as they appear in the human system), and thus how they are altered in the presence of drugs. In contrast, the methods of Douglas et al. and Katrien Pricen et al. use gravitational force or cell lysis, respectively, which alters natural occurring cell-cell interactions and/or membrane integrity.

EXAMPLE 8

Bone marrow was collected via a bone marrow aspiration/bone marrow puncture from a patient and the cells purified over a ficol destiny gradient as described above following manufacture directions. The cells were plated as to the protocol in this application in 384-well black plastic imaging plates (corning) containing nothing. The cells were plated at 20.000 cell/well in 50 ul of RPMI supplemented with 5% FCS 0.1% Pen/strep. The cells were incubated overnight and a viability dye was added (fixable live/dead green, Invitrogen following manufacture directions). The cells were fixed and permeabilized in PBS containing 2% formaldehyde with 0.1% Tween-x114 for 10 minute at room temperature. The solution was then replaced with PBS containing DAPI at manufacture recommended concentration. The plates were imaged at 10× on an Operetta (PE) automated confocal microscope in two channels using band-pass filter light separation (DAPI, GFP). The cells in the monolayer were stained using DAPI (a DNA binding agent) to analyze cell number and existence, and fixable live/dead green dye from Invitrogen to determine viability in the monolayer. As shown in FIG. 14, monolayers of human bone marrow cells as prepared by methods of the present invention comprise viable cells in a physiologically relevant state.

EXAMPLE 9

PBMCs from peripheral blood of a patient diagnosed with primary myelofibrosis were purified over a ficol destiny gradient as described above following manufacture directions. The cells were plated as to the protocol in this application in 384-well black plastic imaging plates (corning) containing 350 FDA approved drugs in DMSO at 10 uM. The cells were plated at 20.000 cell/well in 50 ul of RPMI supplemented with 5% FCS 0.1% Pen/strep. The cells were incubated overnight and a viability dye was added (fixable live/dead green, Invitrogen following manufacture directions). The cells were fixed and permeabilized in PBS containing 2% formaldehyde with 0.1% Tween-x114 for 10 minute at room temperature. The solution was then replaced with PBS containing antibody against CD34 and pSTAT5 (BD biosciences) for 1 hour. The solution was then replaced with PBS containing DAPI at manufacture recommended concentration. The plates were imaged at 10× on an Operetta (PE) automated confocal microscope in four channels using band-pass filter light separation (DAPI, GFP, PE, APC). Using an image analysis pipeline, the sensitivity of the cancer cells (CD34 and pSTAT5 positive) to each drug was compared to the sensitivity on the healthy cells (NOT CD34 and pSTAT5 positive). All results were normalized to the control, DMSO alone. FIG. 12A shows the results as each dot is a drug, the highlighted drugs target the specific cells within the monolayer which are "diagnostic marker" positive (i.e. labeled with specific antibodies). These results are compared to the effect of healthy cells (i.e. marker negative) within the monolayer. The data for one drug was extracted in FIG. 12B and highlights the per/cell phenotype of single drug treatment (right) vs control (left) from a treated monolayer (specific CD34 cell depletion). Using the same method as described above, but only counting cell number, FIG. 12C determines drug effect as to "prior art" of only counting general cell death after incubation with drugs (thus, no comparison to what is sick or what is healthy.) If only cell death/cell number is determined, then the most important drug (highlighted in 12A, 12B left, and 12D) does not appear (outside of the dotted line threshold). FIG. 12D is clinical data obtained using blood-based standardized hospital protocols and in-hospital lab techniques from the patient after treatment with the compound which appears in FIGS. 12A and 12B.

EXAMPLE 10

PBMCs from peripheral blood of a healthy human donor were purified over a ficol destiny gradient as described above following manufacture directions. The cells were plated as to the protocol in this application in 384-well black plastic imaging plates (corning) containing 1500 FDA approved drugs in DMSO at 10 uM, duplicated over an entire screen. The cells were plated at 20.000 cell/well in 50 ul of RPMI supplemented with 5% FCS 0.1% Pen/strep. The cells were incubated for three hours and then a virus was added. Vesicular stomatitis virus (VSV) acts as an immune stimulant and expresses GFP in the cells upon infection, and was added at a CFU of 10. After an overnight incubation the cells were fixed and permeabilized in PBS containing 2% formaldehyde with 0.1% Tween-x114 for 10 minute at room temperature. The solution was then replaced with PBS containing antibody against CD11C, CD14, CD3 and/or CD19 (BD biosciences) for 1 hour. The solution was then replaced with PBS containing DAPI at manufacture recommended concentration. The plates were imaged at 10× on an Operetta (PE) automated confocal microscope in four channels using band-pass filter light separation (DAPI, GFP, PE, APC). Using an image analysis pipeline the neighbor relationship of each cell to the other cells was determined. This was determined in each well, and the effect of the drugs on this cell-cell relationship was measured compared to the control, DMSO. The results are plotted here as clustered drug-annotation results from a large-scale drug screen where the cell-to-cell interactions or "nearest neighbor" cells were determined in a high-throughput fashion. The darker boxes represent relationships that either are gained or lost compared to the control well (DMSO). Thus, drugs are tracked and drug screening libraries are organized based on their ability to increase or distrust these interactions using the method outlined in Example 1.

EXAMPLE 11

Sampling of either peripheral blood or bone marrow were taken from an individual and the mononuclear cells purified over a density gradient, ficol, following manufacture protocols. The cells were then placed into 384-well black/clear bottom multi-well imaging plates (corning) with each well containing either positive or negative controls or drugs. The cells were incubated and then a dye added to determine viability of all cells. The dye used can change depending on the stage of viability or other property is to be determined, or, the dye can be replaced for an antibody after the next step. The cell layer was then fixed and permeabilized using 2% formaldehyde with 0.1% triton-X114 in PBS. Monolayers were then stained with antibodies directed to diagnostic antigens used in hematopoietic cancers or against other antigens of interest. The cells were then stained with DAPI for nuclear visualization all following the protocols above. The plates were imaged at 10× on an Operetta (PE) automated confocal microscope in four channels using band-pass filter light separation (DAPI, GFP, PE, APC). Using an image analysis pipeline the viability of the cell in this case can be tracked as 1) they become viability positive, or 2) they are no longer there in the image compared to DMSO (control).

The markers (dye+fluorescent antibody or just fluorescent antibodies) must not over lap channels, and if they do, the channels must be compensated for using standard excitation/emission compensation techniques. A general layout for non-overlapping channels is DAPI, GFP, PE, and APC. Others can be used.

Accordingly, using the means and methods of the present invention, cells positive for multiple biomarkers and/or multiple cells positive for different biomarkers can be assessed.

EXAMPLE 12

FIG. 13 represents an outline of how cell interactions are determined using an "interaction score", and then the interaction score is applied to an example. The left figure was obtained by collecting PBMCs from peripheral blood of a healthy human donor were purified over a ficol destiny gradient as described above following manufacture directions. The cells were plated as to the protocol in this application in 384-well black plastic imaging plates (corning). The cells were plated at 20.000 cell/well in 50 ul of RPM' supplemented with 5% FCS 0.1% Pen/strep. The cells were incubated for three hours and then a virus was added. After an overnight incubation the cells were fixed and permeabilized in PBS containing 2% formaldehyde with 0.1% Tween-x114 for 10 minute at room temperature. The solution was then replaced with PBS containing antibody against CD11C, CD14, CD3 or CD19 (BD biosciences) for 1 hour. The solution was then replaced with PBS containing DAPI at manufacture recommended concentration. The plates were imaged at 10× on an Operetta (PE) automated confocal microscope in four channels using band-pass filter light separation (DAPI, GFP, PE, APC). The circles provides an example of cellular interactions either together or in triplicate. In two examples, the cells are touching, and in one example two cells tracked are one cell apart. The middle panel describes the calculation of the "interaction score" that we developed to track the cellular relationships to each other that occurring in the monolayers as created by the protocol in example 1 only.

Interactions that are relevant given a specific scenario can be tracked using the methods of the invention. For this, PBMCs from peripheral blood of a healthy human donor were purified over a ficol destiny gradient as described above following manufacture directions. The cells were plated as to the protocol in this application in 384-well black plastic imaging plates (corning) containing nothing or an antibody against human MHC-II (Purified NA/LE Mouse Anti-Human HLA-DR, Clone G46-6, BD biosciences). The cells were plated at 20.000 cell/well in 50 ul of RPM, supplemented with 5% FCS 0.1% Pen/strep. The cells were incubated for three hours and then a virus was added. Vesicular stomatitis virus (VSV) acts as an immune stimulant and expresses GFP in the cells upon infection, and was added at a CFU of 10. After an overnight incubation the cells were fixed and permeabilized in PBS containing 2% formaldehyde with 0.1% Tween-x114 for 10 minute at room temperature. The solution was then replaced with PBS containing antibody against CD11C, and, CD3 (BD biosciences) for 1 hour. The solution was then replaced with PBS containing DAPI at manufacture recommended concentration. The plates were imaged at 10× on an Operetta (PE) automated confocal microscope in four channels using band-pass filter light separation (DAPI, GFP, PE, APC). Using an image analysis pipeline, the cell-cell contacts of CD3-CD11C cells were determined.

For instance, during a virus infection (denoted as "+stimulant) virus peptides are presented by dendritic cells via the receptor MHCII to T-cells (Boes et al. (2002) Nature 418, 983-8). This interaction can be tracked using the methods of the invention (−), and it can be proved that this interaction is real in the means and methods of the present invention by including an antibody against MHCII which blocks the receptor binding (+) (Peiser et al. (2007) Allergy 62(7)). This experiment is simple proof that physiologically relevant cell interactions can be determined through the methods of the invention, and used for novel drug screening.

Tracking of changes is done using an in-house built software. Cell-cell interactions are measured by analyzing the interaction frequency between two cell types on the 2D plane as measured from the images, over all cells present in the well. An "interaction" could be direct cell-cell contact (i.e. are two neighboring cells touching each other with their plasma membranes), or where the two cells are within a certain maximal distance from each other, etc.

In FIG. 13 (left) each cell is stained by the nuclear stain DAPI, and cell type A is stained by one marker set (CD11c for instance) and cell type B is stained by another marker (CD3 for instance). To measure the interaction affinity between these two cell types, first the fraction of As is calculated that are in touch with (i.e. are within a certain maximal distance between their weighted centroids of their nuclei areas) cells of type B as a function of all A+ cells. This is called the observed ("obs") fraction of cells of type A interacting with cells of type B (box in FIG. 13).

*Obs=# A+cells that neighbor B+cells/# all A+cells*

Then, this number is normalized ("obs") to what fraction of As interacting with Bs would be expected by random. The biggest determinant of how many interactions can be expected by random is the total number of cells per well, or the number of cells per area. It is empirically found that this determines the total fraction of interacting cells (between any cell type, which we term "Fi").

*Fi=# cells with at least one neighbor/# all cells*

Therefore, the fraction of cells of type A interacting with cells of type B (i.e. "E") is given by the chance that they meet randomly, which is calculated as "the fraction of type A cells out of all cells" ("Fa")*"the fraction of type B cells out of all cells" ("Fb")*"the total fraction of interacting cells out of all cells" ("Fi"). Note

*Fa=# A+cells/# all cells*

*Fb=# B+cells/# all cells*

The expected fraction of A+ cells out of all A+ cells one would observe to interact with B+ cells assuming random data is therefore

*E=Fa*Fb*Fi.*

Finally, the interaction score is calculated as the log 2-transformed fold-change of "obs"/"E", such that negative interaction scores indicate an interaction frequency lower than one would expect by random (indicative of repulsion or strongly competing interactions affinities to other cell types), whereas a positive interaction score indicates an interaction frequency higher than one would expect by random (indicative of affinity between cells).

Note that an interaction can occur less than one would expect by random, but that deviations (increases or decreases) from that negative interaction score still indicate changes in cellular affinity.

Note that cellular interactions can be measured in various ways, as discussed above. For instance by seeing if the plasma membranes of cells touch, or approximated by measuring if the nuclei of two cells are sufficiently close to each other. The approximation based on nuclear distance is used as these particular images happen to not have a faithful plasma membrane staining for all cells.

EXAMPLE 13

Figure 15B:
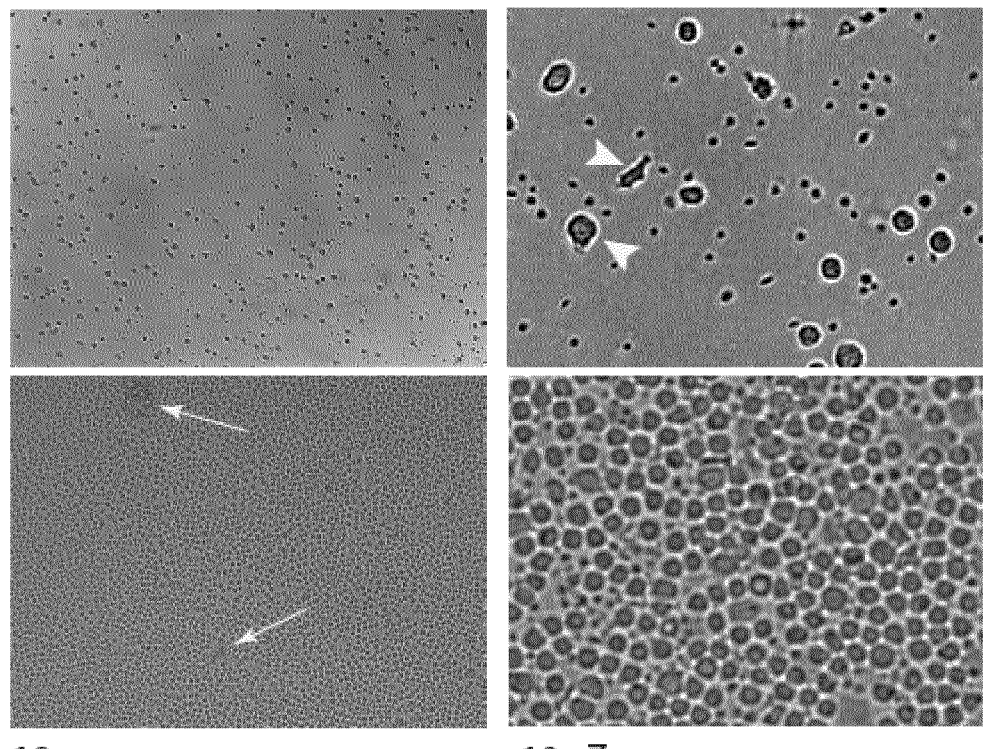
Figure 15C:
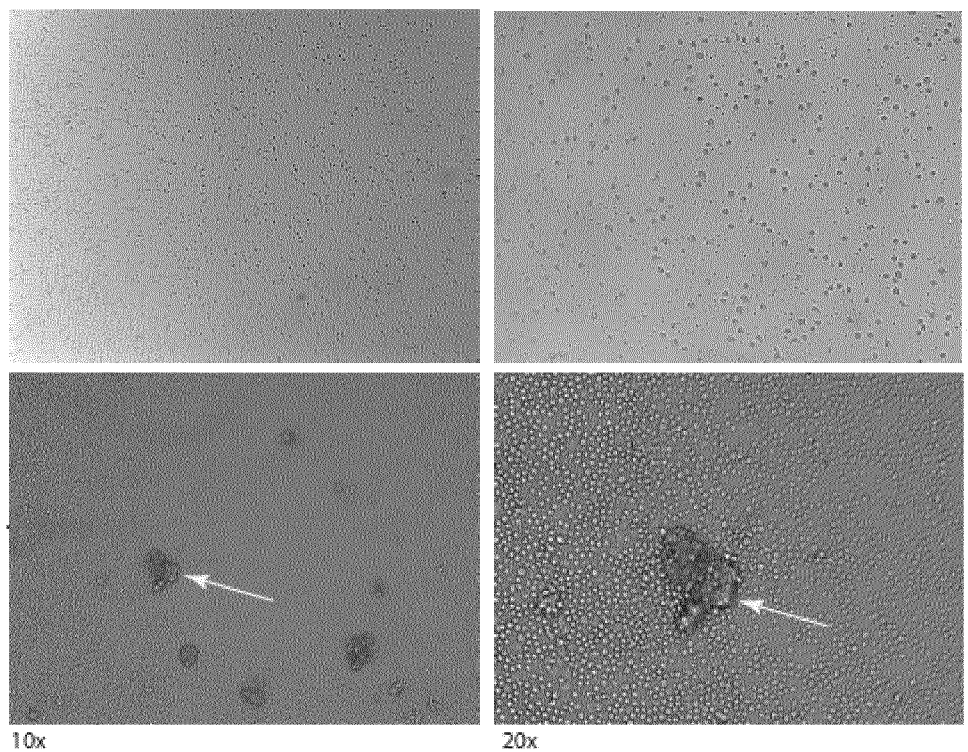

PBMCs from peripheral blood of a healthy human donor were purified over a ficol destiny gradient as described above following manufacture directions. The cells were plated as to the protocol in this application in 384-well black plastic imaging plates (corning) containing nothing The cells were plated at 20.000 cell/well in 50 ul of RPMI supplemented with 5% FCS 0.1% Pen/strep. The plates were imaged at 10× on an Operetta (PE) automated confocal microscope in using brightfield microscopy. The cells in FIG. 15A (right panel) are free to move and interact with their partner cells without physical interference, thus propagating pathways during physiologically relevant situations as in vivo. In FIG. 15B (lower part), PBMCs from peripheral blood of a healthy human donor were purified over a ficol destiny gradient as described above following manufacture directions. The cells were plated as to the protocol in this application in 384-well black plastic imaging plates (corning) containing nothing The cells were plated according to Douglas et al.: at 1w6 cell/well in 50 ul of RPMI supplemented with 5% FCS 0.1% Pen/strep. The plates were imaged at 10× on an Operetta (PE) automated confocal microscope in using brightfield microscopy. In the prior art such as Douglas et al. and Katrien Princen et al., the physical forces of either 1) too many cells, or 2) additional pressure by spinning causes a disproportional number of interactions that then are not relevant and do not occur in nature, or have no barring on drug effect. Arrow=example cell type 1, arrow head=example cell type 2. Where example cell type 1 and 2 on the left have the space to freely move, but in the image on the right will never be able to interact due to the physical interference of all other cells, or spinning. The overpacking of wells is also shown in FIG. 17. Overpacking well creates a non-physiolgically relevant monolayer. Cells plated as described in Douglas et al. (2e6/well) increases the number of adherent cells, thus blocking the placement of non-adherent cell (here: t-cells). Upon removal of the media, non-adherent cells are removed from the well and have not sit, thus leaving the well with a disproportional number of cells (top row, no present T-cells where usually T-cells make up >75% of the monolayer and also are present as 75% of the PBMC population within healthy adult peripheral blood.) On the bottom, the SLP method is used which retains proportional T-cell numbers.

EXAMPLE 14

Comparison of four different populations in PBMCs as measured by flow cytometry or the method provided herein (image analysis of pharmacoscopy well). PBMCs from peripheral blood of a healthy human donor were purified over a ficol destiny gradient as described above following manufacture directions. The cells for flow cytometry were plated at 1e6/well in a 96 well-Vbottom plate in 50 ul. Wells were stained with 1:1000 of antibody against CD11C, CD14, CD3 or CD19 (BD biosciences) for one hour on ice. The cells were washed with PBS with 2% FCS and spun at 2000 RPM for 5 minutes, repeated twice, and then fixed with PBS containing 2% formaldehyde and then washed once more. The resulting populations were measured on a flow cytometer (BD facsaria) and the results were analysed using FlowJo. The comparison populations for image analysis using pharmacoscopy were performed by putting PBCS in 384-well black plastic imaging plates (corning) containing nothing at 20.000 cell/well. The cells were plated in 50 ul of RPMI supplemented with 5% FCS 0.1% Pen/strep. After an overnight incubation the media was removed from all wells, and the cells were fixed and permeabilized in PBS containing 2% formaldehyde with 0.1% Tween-x114 for 10 minute at room temperature. The solution was then replaced with PBS containing antibody against CD11C, CD14, CD3 or CD19 (BD biosciences) for 1 hour. The solution was then replaced with PBS containing DAPI at manufacture recommended concentration. The plates were imaged at 10× on an Operetta (PE) automated confocal microscope in four channels using band-pass filter light separation (DAPI, GFP, PE, APC). The monolayers were quantified using an image analysis pipeline and the numbers compared using MATLAB giving a coloration value of 0.98. As can be seen, subpopulations comprised in the monolayer of the invention are comparable to subpopulations present in PBMC samples as determined by flow cytometry. Accordingly, the monolayer of the present invention resembles a physiologically-relevant state of hematopoietic cells such as PBMCs or bone-marrow cells.

The invention claimed is:

1. A method for determining whether a subject suffering from or predisposed to a disease will respond or is responsive to treatment with a therapeutic agent comprising
   (a) isolating viable PBMCs from a blood sample obtained from said subject;
   (b) incubating said viable PBMCs of step (a) at a density of about 100 cells per mm$^2$ to about 30000 cells per mm$^2$ to form a monolayer of viable cells under conditions that maintain naturally occurring cell-cell interactions and membrane integrity during formation of the monolayer of the viable cells;
   (c) contacting said viable PBMCs in said monolayer of step (b) with said therapeutic agent; and
   (d) assessing the response of PBMCs to the therapeutic agent by microscopic analysis of said monolayer of step (c),
   wherein the viable PBMCs comprise lymphocytes and monocytes, and
   wherein the viable PBMCs are not subjected to centrifugation and/or spinning during the formation of the monolayer.

2. The method of claim 1, further comprising (e) altering or initiating treatment of the subject with said therapeutic agent based on the assessment of step (d).

3. The method of claim 1, wherein the PBMCs are incubated at a density of about 2000 cells per mm$^2$ to form a PBMC monolayer.

4. The method of claim 1, wherein PBMCs are isolated from non-nucleated cells, wherein the PBMCs to be incubated contain less than about 100 non-nucleated cells per PBMC.

5. The method of claim 1, wherein the monolayer is obtained by a method further comprising or wherein the method further comprises a step of adding a viability dye.

6. The method of claim 1, wherein subsequent to isolation the PBMCs are maintained/processed/analyzed at about 1 g, i.e. 9.81 m/s$^2$.

7. The method of claim 1, wherein subsequent to isolation the PBMCs are not subjected to centrifugation or spinning.

8. The method of claim 1, wherein the disease is a hematologic malignancy or a malignancy of myeloid and/or lymphoid tissue.

9. The method of claim 1, wherein the disease is a myeloproliferative disorder, inflammatory disorder, latent virus infection, cellular growth disorder, cellular chemotaxis disorder, metabolic disorder, or autoimmune disorder.

10. The method of claim 9, wherein the disease is leukemia or lymphoma.

11. The method of claim 1, wherein microscopic analysis is confocal microscopic analysis.

12. The method of claim 1, wherein the monolayer is fixed after it is formed so as to maintain natural occurring naturally occurring cell-cell interactions and membrane integrity.

13. The method of claim 12, wherein a detectable label is added to the fixed PBMCs.

14. The method of claim 13, wherein the detectable label is an antibody.

* * * * *

UNITED STATES PATENT AND TRADEMARK OFFICE
CERTIFICATE OF CORRECTION

| | | |
|---|---|---|
| PATENT NO. | : 11,486,876 B2 | Page 1 of 1 |
| APPLICATION NO. | : 15/514045 | |
| DATED | : November 1, 2022 | |
| INVENTOR(S) | : Giulio Superti-Furga, Berend Snijder and Gregory Vladimer | |

It is certified that error appears in the above-identified patent and that said Letters Patent is hereby corrected as shown below:

On the Title Page

Add the following foreign priority information:
-- (30) Foreign Application Priority Data
Sep. 24, 2014 (EP) ............ 14186286 --

Signed and Sealed this
Twenty-fifth Day of June, 2024

Katherine Kelly Vidal
*Director of the United States Patent and Trademark Office*